(12) United States Patent
Yamaguchi et al.

(10) Patent No.: US 11,174,389 B2
(45) Date of Patent: Nov. 16, 2021

(54) PHOSPHOLE COMPOUND

(71) Applicant: NATIONAL UNIVERSITY CORPORATION NAGOYA UNIVERSITY, Nagoya (JP)

(72) Inventors: Shigehiro Yamaguchi, Nagoya (JP); Aiko Naka, Nagoya (JP); Masayasu Taki, Nagoya (JP); Chenguang Wang, Nagoya (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 408 days.

(21) Appl. No.: 16/329,151

(22) PCT Filed: Jul. 24, 2017

(86) PCT No.: PCT/JP2017/026732
§ 371 (c)(1),
(2) Date: May 10, 2019

(87) PCT Pub. No.: WO2018/042947
PCT Pub. Date: Mar. 8, 2018

(65) Prior Publication Data
US 2019/0264031 A1    Aug. 29, 2019

(30) Foreign Application Priority Data
Aug. 31, 2016   (JP) ............................. JP2016-168880

(51) Int. Cl.
C09B 57/00    (2006.01)
C09K 11/06    (2006.01)
(Continued)

(52) U.S. Cl.
CPC .............. *C09B 57/00* (2013.01); *A61K 49/00* (2013.01); *C07F 9/6568* (2013.01); *C09K 11/06* (2013.01);
(Continued)

(58) Field of Classification Search
None
See application file for complete search history.

(56) References Cited

U.S. PATENT DOCUMENTS

2016/0333037 A1   11/2016   Yamaguchi et al.

FOREIGN PATENT DOCUMENTS

| JP | 2008-56630 A | 3/2008 |
| JP | 2014-535054 A | 12/2014 |

(Continued)

OTHER PUBLICATIONS

International Search Report dated Aug. 22, 2017 from International Application No. PCT/JP2017/026732, 4 pages, Including English translation.

(Continued)

*Primary Examiner* — Xiaoyun R Xu
(74) *Attorney, Agent, or Firm* — MH2 Technology Law Group, LLP

(57) ABSTRACT

A phosphole compound represented by the formula (1)

(Continued)

(wherein $Ar^1$ and $Ar^2$ are the same or different, and represent an optionally substituted aromatic hydrocarbon ring or an optionally substituted heteroaromatic ring; $Ar^3$ represents a divalent π-conjugated unit; $R^1$ represents an optionally substituted alkyl group, an optionally substituted cycloalkyl group, an optionally substituted aryl group, or an optionally substituted heteroaryl group; $R^2$ and $R^3$ are the same or different, and represent a hydrogen atom, an optionally substituted alkyl group, an optionally substituted cycloalkyl group, an optionally substituted aryl group, or an optionally substituted heteroaryl group; and Z represents a reactive group) can provide a fluorescent dye capable of maintaining a high fluorescence quantum yield irrespective of solvent polarity, and providing an improved fluorescence quantum yield and light resistance even in environments containing large amounts of water.

16 Claims, 14 Drawing Sheets

(51) Int. Cl.
  *G01N 21/64* (2006.01)
  *G01N 33/58* (2006.01)
  *C07F 9/6568* (2006.01)
  *A61K 49/00* (2006.01)
(52) U.S. Cl.
  CPC ......... *G01N 21/64* (2013.01); *G01N 21/6428* (2013.01); *G01N 33/582* (2013.01); *G01N 2021/6439* (2013.01)

(56) References Cited

FOREIGN PATENT DOCUMENTS

| JP | 2015-516068 A | 6/2015 |
| WO | 2013/068372 A1 | 5/2013 |
| WO | 2013/164697 A1 | 11/2013 |
| WO | 2015/111647 A1 | 7/2015 |

OTHER PUBLICATIONS

He et al., "Synthesis of P-Triazole Dithienophospholes and a Cyclodextrin-Based Sensor via Click Chemistry", Organic Letters, 2013, vol. 15, No. 20, pp. 5322-5325.

Chen et al., "Benzofuran-fused Phosphole: Synthesis, Electronic, and Electroluminescence Properties", Organic Letters, 2013, vol. 15, No. 2, pp. 330-333.

Takahashi et al., "Synthesis and Properties of Benzophospholo[3,2-b]benzofuran Derivatives", The Journal of Organic Chemistry, 2015, vol. 80, pp. 3790-3797.

Fukazawa et al., "Ladder π-Conjugated Containing Main-Group Elements", Chemistry-An Asian Journal, 2009, vol. 4, pp. 1386-1400.

Fukazawa et al., "Bis-Phosphoryl-Bridge Stilbenes Synthesized by an Intramolecular Cascade Cyclization", Organic Letters, 2008, vol. 10, No. 5, pp. 913-916.

Fukazawa et al., "Benzo[b]phosphole-Containing π-Electron Systems: Synthesis Based on an Intramolecular tran-Halophosphanylation and Some Insights into Their Properties", Chemistry—An Asian Journal, 2009, vol. 4, pp. 1729-1740.

PHOSPHOLE COMPOUND

CROSS-REFERENCE TO RELATED APPLICATIONS

This application is a U.S. National Stage application of PCT/JP2017/026732 filed 24 Jul. 2017, which claims priority to Japanese Application No. 2016-168880 filed 31 Aug. 2016, the entire disclosures of which are incorporated herein by reference.

TECHNICAL FIELD

The present invention relates to a phosphole compound.

BACKGROUND ART

Fluorescent organic compounds that have high fluorescence quantum yields are important as luminescent materials for organic EL elements or as fluorescent dyes for in vivo fluorescence imaging. There have been numerous reports on both basic research and applied research of fluorescent organic compounds.

However, with continued irradiation with light, many of the conventionally known fluorescent organic compounds gradually decompose and suffer from photobleaching. For example, as fluorescent probes, Alexa Fluor dye, ATTO dye, etc. are well known as a group of dyes having improved light resistance. However, repeated super-resolution microscopy observation, such as stimulated emission depletion (STED) imaging, is difficult even with use of such dyes. Therefore, the object to be observed by the state-of-the-art fluorescence microscopy technique is limited at present, and improvement in light resistance of fluorescent dyes has been desired.

Among such prior art compounds, phosphole compounds having a specific structure are also known as fluorescent dyes (see, for example, Patent Literature (PTL) 1 and Non-patent Literature (NPL) 1). The phosphole compound disclosed in PTL 1 can maintain a high fluorescence quantum yield in any solvent ranging from low-polarity to high-polarity solvents, and some embodiments of the phosphole compound disclosed in PTL 1 are fluorescent dyes with excellent light resistance.

CITATION LIST

Patent Literature

PTL 1: WO2015/111647

Non-Patent Literature

NPL 1: Chem. Asian J. 2009, 4, 1729-1740.

SUMMARY OF INVENTION

Technical Problem

The fluorescent dyes disclosed in PTL 1 and NPL 1 have high fluorescence quantum yields and excellent light resistance. There is, however, still room for improvement in terms of fluorescence quantum yield in environments containing large amounts of water. For example, cells, tissues, living organisms, etc. are mainly composed of water. The object to be observed by fluorescence bioimaging is present in a trace amount and is very small. Therefore, water solubility and a high fluorescence quantum yield of the fluorescent dye in aqueous solutions are important for high-sensitivity observation with a high signal-to-noise ratio. Accordingly, the development of a molecule capable of efficiently emitting fluorescence even in water has been desired for use as a fluorophore for fluorescence bioimaging of cells, tissues, living organisms, etc. The fluorescent dyes disclosed in NPL 1 and PTL 1 do not dissolve in water. Furthermore, the fluorescence quantum yield of the fluorescent dye disclosed in PTL 1 is reduced when water is added to the organic solvent.

Further, among general-purpose lasers in confocal laser scanning microscopes for fluorescence imaging, those frequently used are short-wavelength lasers with a wavelength of, for example, 405 nm, 430 nm, or 488 nm. In particular, the fluorescent dye disclosed in NPL 1 has an absorption peak wavelength of 367 nm, and thus cannot be excited with such lasers of short wavelengths. Therefore, application of such light sources to the fluorescent dye disclosed in NPL 1 is difficult. Further, in consideration of phototoxicity against cells, using a longer wavelength laser is preferable.

The present invention aims to solve the above problem of the prior art. An object of the present invention is to provide a fluorescent dye that is capable of maintaining a high fluorescence quantum yield irrespective of solvent polarity, and providing an improved fluorescence quantum yield and light resistance even in environments containing large amounts of water, and that is also widely applicable for fluorescence bioimaging of cells, tissues, living organisms, etc.

Solution to Problem

In view of the above problem, the present inventors conducted extensive research and found that phosphole compounds having a specific structure have a high fluorescence quantum yield irrespective of solvent polarity, achieve an improved fluorescence quantum yield even in environments containing large amounts of water, and have significantly improved light resistance, as compared with conventional fluorescent dyes; and that therefore, such phosphole compounds are fluorescent dyes that can withstand repeated super-resolution microscopy observation, such as stimulated emission depletion (STED) imaging. The inventors conducted further research based on this finding, and accomplished the present invention. More specifically, the present invention includes the following.

Item 1. A phosphole compound represented by formula (1):

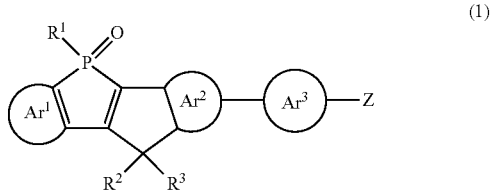

(wherein $Ar^1$ and $Ar^2$ are the same or different, and represent an optionally substituted aromatic hydrocarbon ring or an optionally substituted heteroaromatic ring;
$Ar^3$ represents a divalent π-conjugated unit;
$R^1$ represents an optionally substituted alkyl group, an optionally substituted cycloalkyl group, an optionally substituted aryl group, or an optionally substituted heteroaryl group;

$R^2$ and $R^3$ are the same or different, and represent a hydrogen atom, an optionally substituted alkyl group, an optionally substituted cycloalkyl group, an optionally substituted aryl group, or an optionally substituted heteroaryl group; and Z represents a reactive group).

Item 2. The phosphole compound according to Item 1, wherein $Ar^3$ represents an optionally substituted alkenylene group, an optionally substituted alkynylene group, an optionally substituted arylene group, or an optionally substituted heteroarylene group.

Item 3. The phosphole compound according to Item 1 or 2, which is represented by formula (1B):

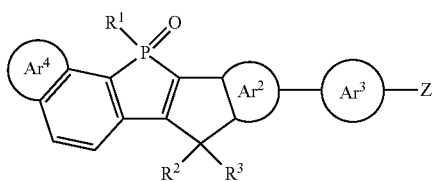

(1B)

(wherein $Ar^2$, $Ar^3$, $R^1$, $R^2$, $R^3$, and Z are as defined above, and $Ar^4$ represents an optionally substituted aromatic hydrocarbon ring).

Item 4. The phosphole compound according to any one of Items 1 to 3, wherein Z is carboxy or alkoxycarbonyl.

Item 5. The phosphole compound according to any one of Items 1 to 3, wherein the reactive group is an amine reactive group or a thiol reactive group.

Item 6. The phosphole compound according to Item 5, wherein the amine reactive group or the thiol reactive group is a group having a structure represented by one of formulas (2A) to (2E) at an end thereof:

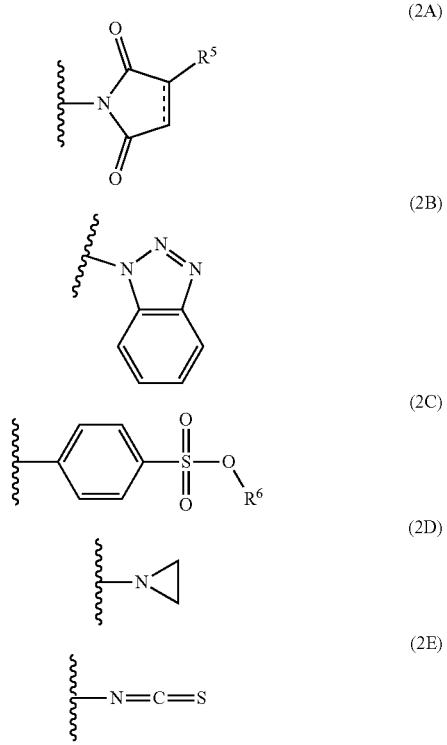

(wherein $R^5$ represents a hydrogen atom or a sulfo group, $R^6$ represents an alkyl group, and the bond indicated by a solid line and a dashed line represents a single bond or a double bond).

Item 7. A fluorescent dye comprising the phosphole compound according to any one of Items 1 to 6.

Item 8. The fluorescent dye according to Item 7, which is for stimulated emission depletion (STED) imaging.

Item 9. A protein labeling agent comprising the phosphole compound according to Item 5 or 6.

Item 10. A stimulated emission depletion (STED) imaging method using the phosphole compound according to any one of Items 1 to 6 or the fluorescent dye according to Item 7 or 8.

Item 11. A protein labeling kit comprising the phosphole compound according to Item 5 or 6, the fluorescent dye according to Item 7 or 8, or the protein labeling agent according to Item 9.

Item 12. A protein labeling method comprising reacting a protein with the phosphole compound according to Item 5 or 6, the fluorescent dye according to Item 7 or 8, or the protein labeling agent according to Item 9.

Advantageous Effects of Invention

The phosphole compound of the present invention has an absorption peak in the visible light wavelength range (in particular, about 400 to 500 nm) irrespective of solvent polarity, and has a high fluorescence quantum yield. Furthermore, the phosphole compound of the present invention can have enhanced fluorescence quantum yield even in environments containing large amounts of water, and is widely applicable to fluorescence bioimaging of cells, tissues, living organisms, etc.

Therefore, the phosphole compound of the present invention is a fluorescent dye suitable for repeated super-resolution microscopy observation, such as stimulated emission depletion (STED) imaging.

Furthermore, the phosphole compound of the present invention wherein the reactive group represented by Z is an amine reactive group or a thiol reactive group can function as a protein labeling agent that labels proteins.

BRIEF DESCRIPTION OF DRAWINGS

FIG. 8(*a*) is a confocal fluorescence microscopy image of tubulin immunolabeled with Phox-NHS Ester (Example 9), FIG. 8(*b*) is a STED microscopy image of tubulin immunolabeled with Phox-NHS Ester (Example 9), and FIG. 8(*c*) is a graph showing optical resolutions of the corresponding confocal (orange line) and STED (crimson line) microscopy images.

FIG. 9(*a*) is STED microscopy images of tubulin immunolabeled with Alexa Fluor 488 repeatedly captured 5 times (Comparative Example 4); FIG. 9(*b*) is STED microscopy images of tubulin immunolabeled with Phox-NHS Ester (Example 9) repeatedly captured 5 times; and FIG. 9(*c*) is normalized intracellular fluorescence intensity plotted as a function of the number of recorded STED microscopy images.

FIG. 10(*b*) is a Z-scan STED microscopy image of tubulin immunolabeled with Phox-NHS Ester (Example 9) at a depth of 2 µm. FIG. 10(*c*) shows a 3D structure of tubulin immunolabeled with Phox-NHS Ester (Example 9).

FIG. 11(*b*) is a Z-scan STED microscopy image of tubulin immunolabeled with Alexa Fluor 488 (Comparative Example 4) at a depth of 2 µm. FIG. 11(*c*) shows a 3D structure of tubulin immunolabeled with Alexa Fluor 488 (Comparative Example 4).

FIG. 12(*b*) shows a line profile taken along the arrow in FIG. 13(*a*) across the filaments.

FIG. 13(*a*) is a confocal microscopy image (left), a STED microscopy image (middle), and intensity profiles (right). The confocal and STED microscopy images each include an enlarged view of the portion surrounded by dotted lines. The intensity profiles show the confocal microscopy image with a black line, and the STED microscopy image with a green line. FIG. 13(*b*) shows the first five STED microscopy images stained with Phox-COOH. FIG. 13(*c*) shows the first five STED microscopy images stained with Alexa Fluor 488. FIG. 13(*d*) shows integrated fluorescence intensity plotted as a function of the number of recorded STED images. All images were recorded with excitation at 470 nm, and a STED laser of 592 nm (CW-STED, 30 mW) was used for STED. Scare bars indicate 2 µm.

FIG. 14(*a*) shows repeatedly captured STED microscopy images. Each numeral represents the number of flames. FIG. 14(*b*) shows typical intensity profiles of microtubules labeled with Phox-COOH in the images (number of flames: 1, 10, 20 and 30). The full width at half maximum (FWHM) was computed at a resolution of microtubules calculated from the Gaussian fit. FIG. 14(*c*) shows statistical analysis of FWHM at 10 fluorescence spots using the Gaussian fit.

FIG. 15(*b*) shows STED images along the corresponding xz and yz planes in FIG. 15(*a*).

FIG. 17(*f*) shows integration fluorescence intensities (I) relative to the initial value ($I_0$) plotted as a function of the number of recorded images. FIG. 17(*g*) shows first-order plots based on changes in fluorescence intensity. The photobleaching rate was calculated from the slope of the straight line and normalized to that of Alexa Fluor 430. The relative photostability refers to the reciprocal of the photobleaching rate normalized in Table 2.

FIG. 19(*c*) is an image obtained by subtracting (removing) the image of FIG. 19(*b*) from the image of FIG. 19(*a*). FIG. 19(*d*) is a two-color STED microscopy image obtained by combining the image of FIG. 19(*b*) with the image of FIG. 19(*c*).

FIG. 20(a) is a two-color STED microscopy image (deconvoluted data) of microtubules (green) and vimentin filaments (magenta) separately immunolabeled with Phox-COOH (PB430) and Alexa Fluor 430, respectively. The intensity profile plotted along the dotted lines was intersected with microtubules (b) and vimentin filaments (d) in the inset of the two-color STED image. The profile was fit to Gaussian distribution. FIG. 20(d) shows statistical analysis of the full width at half maximum (FWHM) resolution (n=10).

DESCRIPTION OF EMBODIMENTS

Figure 1:
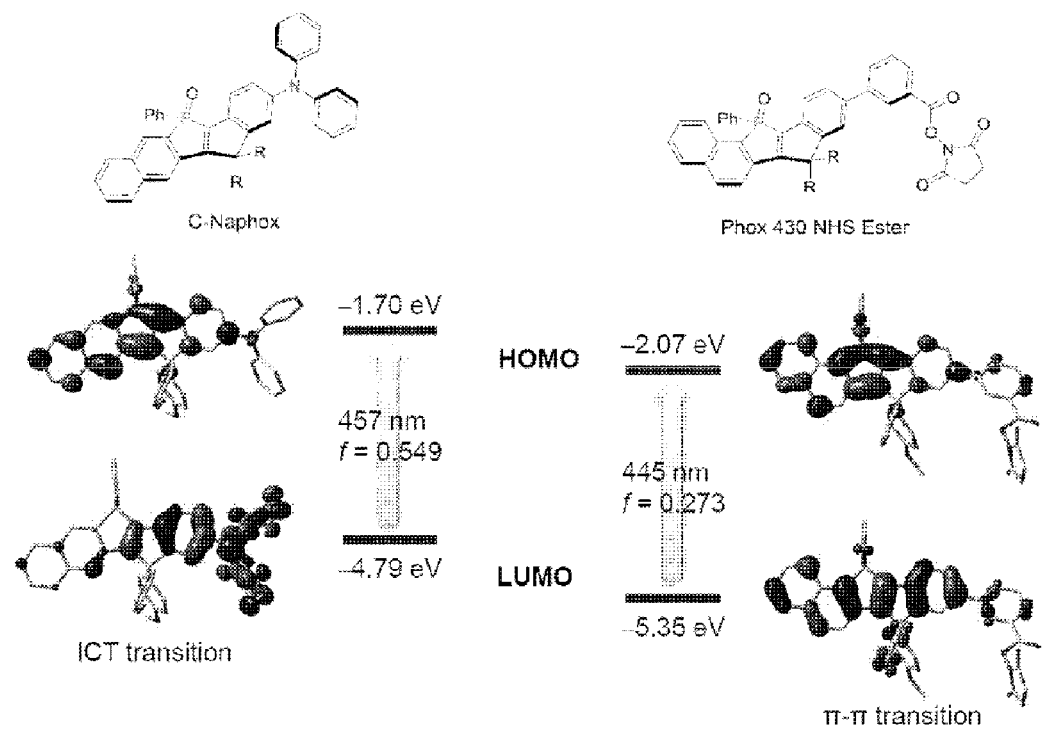
FIG. 1 shows Kohn-Sham plots and HOMO and LUMO energy levels of Phox 430 NHS Ester obtained in Example 6 and C-Naphox obtained in Comparative Example 3.

The term "comprise" used herein includes the concept of "consisting essentially of" and "consisting of." Further, the numerical range referred to by "A to B" means that the range is at least A but not more than B.

1. Phosphole Compound

The phosphole compound of the present invention is a compound represented by formula (1):

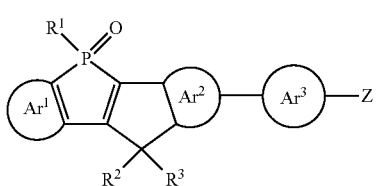

(1)

wherein $Ar^1$ and $Ar^2$ are the same or different, and represent an optionally substituted aromatic hydrocarbon ring or an optionally substituted heteroaromatic ring; $Ar^3$ represents a divalent π-conjugated unit; $R^1$ represents an optionally substituted alkyl group, an optionally substituted cycloalkyl group, an optionally substituted aryl group, or an optionally substituted heteroaryl group; $R^2$ and $R^3$ are the same or different, and represent a hydrogen atom, an optionally substituted alkyl group, an optionally substituted cycloalkyl group, an optionally substituted aryl group, or an optionally substituted heteroaryl group; and Z represents a reactive group.

The phosphole compound of the present invention, which has a fused phosphole skeleton, has excellent light resistance and can have various reactive groups introduced thereinto via $Ar^3$. Due to the presence of $Ar^3$ as a mediator in this manner, the phosphole compound can exhibit a high fluorescence quantum yield even in environments containing large amounts of water.

As the terminal reactive group, various substituents can be introduced. For example, when an amine reactive group, a thiol reactive group, or the like is introduced, the resulting phosphole compound can be used as a protein labeling agent (in particular, an antibody labeling agent) that labels a protein (in particular, an antibody). Thus, the phosphole compound of the present invention can inhibit a decrease in fluorescence brightness during repeated super-resolution microscopy observation, such as in vivo stimulated emission depletion (STED) imaging, the phosphole compound of the present invention is suitable for use in repeated super-resolution microscopy observation, such as in vivo stimulated emission depletion (STED) imaging.

Examples of the aromatic hydrocarbon ring represented by $Ar^1$ in formula (1) include monocyclic aromatic hydrocarbon rings and polycyclic aromatic hydrocarbon rings. Examples of the monocyclic aromatic hydrocarbon ring include a benzene ring. Examples of the polycyclic aromatic hydrocarbon ring include a naphthalene ring, an anthracene ring, a phenanthrene ring, a fluorene ring, a pyrene ring, a triphenylene ring, and the like.

The aromatic hydrocarbon ring represented by $Ar^1$ may optionally have one or more substituents. Examples of substituents include alkyl groups described below, cycloalkyl groups described below, aryl groups described below, heteroaryl groups described below, alkenyl groups (e.g., vinyl, propenyl), alkynyl groups (e.g., ethynyl, 1-propynyl group), carbonyl, cyano, nitro, and the like. When the aromatic hydrocarbon ring has one or more substituents, the number of substituents is, for example, preferably 1 to 6, and more preferably 1 to 3.

Examples of the heteroaromatic ring represented by $Ar^1$ in formula (1) include a pyrrolidine ring, a pyrrole ring, a tetrahydrothiophene ring, a thiophene ring, an oxorane ring, a furan ring, an imidazole ring, a pyrazole ring, a thiazole ring, an oxazole ring, a piperidine ring, a pyridine ring, a pyrazine ring, an indole ring, an isoindole ring, a benzimidazole ring, a quinoline ring, an isoquinoline ring, a quinoxaline ring, and the like.

The heteroaromatic ring represented by $Ar^1$ may optionally have one or more substituents. Examples of substituents include alkyl groups described below, cycloalkyl groups described below, aryl groups described below, heteroaryl groups described below, alkenyl groups (e.g., vinyl, propenyl), alkynyl groups (e.g., ethynyl, 1-propynyl), carbonyl, cyano, nitro, halogen atoms (e.g., fluorine, chlorine, bromine, iodine), and the like. When the heteroaromatic ring has one or more substituents, the number of substituents is, for example, preferably 1 to 6, and more preferably 1 to 3.

From the viewpoint of ease of synthesis, $Ar^1$ is preferably an optionally substituted aromatic hydrocarbon ring, and more preferably an optionally substituted polycyclic aromatic hydrocarbon ring.

When $Ar^1$ is an optionally substituted polycyclic aromatic hydrocarbon ring, the phosphole compound of the present invention can be either a phosphole compound represented by formula (1A):

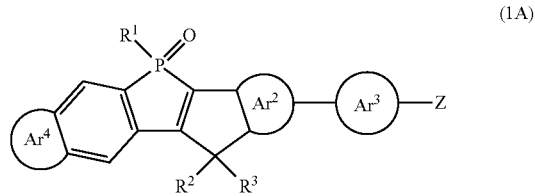

(1A)

(wherein $Ar^2$, $Ar^3$, $R^1$, $R^2$, $R^3$, and Z are as defined above, and $Ar^4$ represents an optionally substituted aromatic hydrocarbon ring), or a phosphole compound represented by formula (1B):

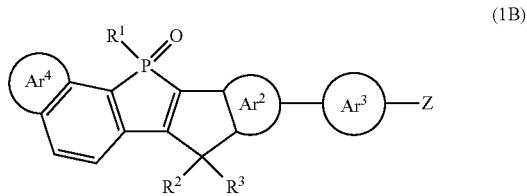

(1B)

(wherein $Ar^2$, $Ar^3$, $Ar^4$, $R^1$, $R^2$, $R^3$, and Z are as defined above).

Examples of the aromatic hydrocarbon ring represented by $Ar^4$ in formulas (1A) and (1B) include those described above. The kind and number of substituents can also be the same as described above.

Among phosphole compounds represented by formula (1A) and phosphole compounds represented by formula (1B), those represented by formula (1B) are preferable from the viewpoint of decreasing the energy difference between the HOMO level (highest unoccupied molecular orbital energy level) and the LUMO level (lowest unoccupied molecular orbital energy level) and increasing the absorption peak wavelength and the fluorescence peak wavelength.

Examples of the aromatic hydrocarbon ring represented by $Ar^2$ in formula (1) may be the same as described above. The same applies to the kind and number of substituents.

Examples of the heteroaromatic ring represented by $Ar^2$ in formula (1) may be the same as described above. The same applies to the kind and number of substituents.

Preferable examples of $Ar^2$ include optionally substituted aromatic hydrocarbon rings. Particularly preferable examples are unsubstituted aromatic hydrocarbon rings.

Examples of the divalent π-conjugated unit represented by $Ar^3$ in formula (1) include alkenylene, alkynylene, arylene, heteroarylene, and like groups.

Examples of the alkenylene group include vinylene, propenylene, butenylene, and like $C_{2-6}$ alkenylene groups, in particular, $C_{2-4}$ alkenylene groups.

The alkenylene group may optionally have one or more substituents. Examples of substituents include cycloalkyl groups described below, aryl groups described below, heteroaryl groups described below, alkenyl groups (e.g., vinyl, propenyl), alkynyl groups (e.g., ethynyl, 1-propynyl), alkoxy groups, carbonyl, cyano, nitro, halogen atoms (e.g., fluorine, chlorine, bromine, iodine), and the like. When the alkenylene group has one or more substituents, the number of substituents may be, for example, preferably 1 to 6, and more preferably 1 to 3.

The alkoxy group as a substituent means a group represented by —OR. In this specification, R in the alkoxy group includes not only alkyl groups described below, but also groups having alkyl chains linked to each other by an ether bond via an oxygen atom, groups having a carboxy group bonded to an alkyl chain, groups having alkyl chains linked to each other by an ether bond via —COO—, and the like. Specific examples include methoxy, ethoxy, n-propoxy, isopropoxy, n-butoxy, isobutoxy, sec-butoxy, tert-butoxy, —O((CH$_2$)$_p$O)$_q$CH$_3$ (wherein p is an integer of 1 to 5, in particular, an integer of 1 to 3; and q is an integer of 1 to 20, in particular, an integer of 2 to 10), —O—CH$_2$—COOH, —O—CH$_2$—COOC$_2$H$_5$, —O((CH$_2$)$_r$—COO)$_s$CH$_3$ (wherein r is an integer of 1 to 5, in particular, an integer of 1 to 3; and s is an integer of 1 to 20, in particular, an integer of 2 to 10), and the like.

Examples of the alkynylene group include ethynylene, propynylene, butynylene, and like $C_{2-6}$ alkynylene groups, in particular, $C_{2-4}$ alkynylene groups.

The alkynylene group may have one or more substituents. Examples of substituents include cycloalkyl groups described below, aryl groups described below, heteroaryl groups described below, alkenyl groups (e.g., vinyl, propenyl), alkynyl groups (e.g., ethynyl, 1-propynyl), alkoxy groups described above, carbonyl, cyano, nitro, and the like. When the alkynylene group has one or more substituents, the number of substituents is, for example, preferably 1 to 6, and more preferably 1 to 3.

Examples of the arylene group include phenylene, naphtylene, anthracenylene, phenanthrenylene, fluorenylene, pyrenylene, triphenylene, and the like.

The arylene group may have one or more substituents. Examples of substituents include alkyl groups described below, cycloalkyl groups described below, aryl groups described below, heteroaryl groups described below, alkenyl groups (e.g., vinyl, propenyl), alkynyl groups (e.g., ethynyl, 1-propynyl), alkoxy groups described above, carbonyl, cyano, nitro, halogen atoms (e.g., fluorine, chlorine, bromine, iodine), and the like. When the arylene group has one or more substituents, the number of substituents is, for example, preferably 1 to 6, and more preferably 1 to 3.

Examples of the heteroarylene group include pyrrolidylene, pyrolylene, tetrahydrothienylene, thienylene, oxolanylene, furanylene, imidazolene, pyrazolene, thiazolene, oxazolene, piperidinylene, pyridylene, pyrazylene, indolylene, cindolylene, benzimidazolylene, quinolylene, isoquinolylene, quinoxalylene, and the like.

The heteroarylene group may optionally have one or more substituents. Examples of substituents include alkyl groups described below, cycloalkyl groups described below, aryl groups described below, heteroaryl groups described below, alkenyl groups (e.g., vinyl, propenyl), alkynyl groups (e.g., ethynyl, 1-propynyl group), alkoxy groups described above, carbonyl, cyano, nitro, halogen atoms (e.g., fluorine, chlorine, bromine, iodine), and the like. When the aromatic hydrocarbon ring has one or more substituents, the number of substituents is, for example, preferably 1 to 6, and more preferably 1 to 3.

From the viewpoint of increasing the absorption peak wavelength and the fluorescence peak wavelength (in particular, the absorption peak wavelength), $Ar^3$ is preferably an optionally substituted arylene group. $Ar^3$ is more preferably an unsubstituted arylene group, and even more preferably phenylene. Among these, $Ar^3$ is most preferably m-phenylene from the viewpoint of introducing a protein-labeling site, while optical properties (e.g., absorption peak wavelength, fluorescence peak wavelength, fluorescence quantum yield) of the dye are less affected.

Examples of the alkyl group represented by $R^1$ in formula (1) include both straight-chain alkyl groups and branched-chain alkyl groups. Examples include methyl, ethyl, n-propyl, isopropyl, n-butyl, isobutyl, sec-butyl, tert-butyl, and like $C_{1-10}$ alkyl groups, in particular, $C_{1-6}$ alkyl groups.

The alkyl group represented by $R^1$ may have one or more substituents. Examples of substituents include cycloalkyl groups described below, aryl groups described below, heteroaryl groups described below, alkenyl groups (e.g., vinyl, propenyl), alkynyl groups (e.g., ethynyl, 1-propynyl), alkoxy groups described above, carbonyl, cyano, nitro, halogen atoms (e.g., fluorine, chlorine, bromine, iodine), and the like. When the aromatic hydrocarbon ring has one or more substituents, the number of substituents is, for example, preferably 1 to 6, and more preferably 1 to 3.

Examples of the cycloalkyl group represented by $R^1$ in formula (1) include cyclopropyl, cyclobutyl, cyclopentyl, cyclohexyl, cycloheptyl, and like $C_{3-10}$ cycloalkyl groups, and in particular, $C_{4-8}$ cycloalkyl groups.

The cycloalkyl group represented by $R^1$ may have one or more substituents. Examples of substituents include alkyl groups described above, cycloalkyl groups described above, aryl groups described below, heteroaryl groups described below, alkenyl groups (e.g., vinyl, propenyl), alkynyl groups (e.g., ethynyl, 1-propynyl), alkoxy groups described above, carbonyl, cyano, nitro, halogen atoms (e.g., fluorine, chlorine, bromine, iodine), and the like. When the aromatic hydrocarbon ring has one or more substituents, the number of substituents is, for example, preferably 1 to 6, and more preferably 1 to 3.

Examples of the aryl group represented by $R^1$ in formula (1) include both monocyclic aryl groups and polycyclic aryl groups. Examples include $C_{6-18}$ aryl groups, in particular, $C_{6-14}$ aryl groups. Examples of monocyclic aryl groups include phenyl. Examples of polycyclic aryl groups include naphthyl, anthracenyl, phenanthrenyl, biphenyl, terphenyl, fluorenyl, pyrenyl, triphenylenyl, and the like.

The aryl group represented by $R^1$ may have one or more substituents. Examples of substituents include alkyl groups described above, cycloalkyl groups described above, aryl groups described above, heteroaryl groups described below, alkenyl groups (e.g., vinyl, propenyl), alkynyl groups (e.g., ethynyl, 1-propynyl), alkoxy groups described above, carbonyl, cyano, nitro, halogen atoms (e.g., fluorine, chlorine, bromine, iodine), and the like. When the aromatic hydrocarbon ring has one or more substituents, the number of substituents is, for example, preferably 1 to 6, and more preferably 1 to 3.

Examples of the heteroaryl group represented by $R^1$ in formula (1) include pyrrolidinyl, pyrrolyl, tetrahydrothienyl, thienyl, oxolanyl, furanyl, imidazolyl, pyrazolyl, thiazolyl, oxazolyl, piperidyl, pyridyl, pyrazyl, indolyl, isoindolyl, benzimidazolyl, quinolyl, isoquinolyl, quinoxalyl, and the like.

The heteroaryl group represented by $R^1$ may optionally have one or more substituents. Examples of substituents include alkyl groups described above, cycloalkyl groups described above, aryl groups described above, heteroaryl groups described above, alkenyl groups (e.g., vinyl, propenyl), alkynyl groups (e.g., ethynyl, 1-propynyl), alkoxy groups described above, carbonyl, cyano, nitro, halogen atoms (e.g., fluorine, chlorine, bromine, iodine), and the like. When the aromatic hydrocarbon ring has one or more substituents, the number of substituents is, for example, preferably 1 to 6, and more preferably 1 to 3.

Among these, $R^1$ is preferably an optionally substituted aryl group, more preferably an optionally substituted phenyl group, and still more preferably phenyl from the viewpoint of the absorption peak wavelength and the fluorescence peak wavelength.

Examples of alkyl, cycloalkyl, aryl, and heteroaryl groups represented by $R^2$ and $R^3$ in formula (1) may be the same as described above. The same applies to the kind and number of substituents.

Among these, $R^2$ and $R^3$ are preferably optionally substituted aryl groups. From the viewpoint of water solubility, substituted aryl groups are more preferable, aryl groups substituted with alkoxy are even more preferable, aryl groups substituted with, for example, —O((CH$_2$)$_p$O)$_q$CH$_3$ (wherein p is an integer of 1 to 5, and in particular, an integer of 1 to 3; and q is an integer of 1 to 20, and in particular, an integer of 2 to 10) or —O(CH$_2$)$_r$SO$_3$H (wherein r is an integer of 1 to 5, and in particular, an integer of 1 to 3) are particularly preferable. Aryl groups substituted with —O(CH$_2$)$_r$SO$_3$H (wherein r represents an integer of 1 to 5, and in particular, an integer of 1 to 3) are the most preferable.

The reactive group represented by Z in formula (1) is not particularly limited. The phosphole compound wherein Z is carboxy; alkoxycarbonyl; hydroxy; amino; halogenated alkyl, such as chloromethyl; isocyano; isothiacyano; or the like (in particular, carboxy or alkoxycarbonyl) can be easily converted to have a protein labeling group (e.g., an amine reactive group, a thiol reactive group) at position Z by reacting the reactive group with a compound having a desired substituent. Therefore, a group of compounds wherein Z is carboxy or alkoxycarbonyl, or a protein labeling group (e.g., an amine reactive group, a thiol reactive group), falls within the scope of the phosphole compound of the present invention.

The amine reactive group refers to a group that is reactive with an optionally substituted amino group possessed by the compound to be labeled. When the amine reactive group is reacted with an optionally substituted amino group possessed by a protein (in particular, an antibody), the phosphole compound of the present invention can function as a protein labeling agent (in particular, an antibody labeling agent).

The thiol reactive group is a group that is reactive with an optionally substituted thiol group possessed by the compound to be labeled. The phosphole compound of the present invention can function as a protein labeling agent (particularly an antibody labeling agent) by reacting with an optionally substituted thiol group possessed by a protein (in particular, an antibody).

Preferable examples of such amine reactive groups or thiol reactive groups are groups terminally having one of the following structures represented by formulas (2A) to (2E) (i.e., an amine-reactive end or a thiol-reactive end):

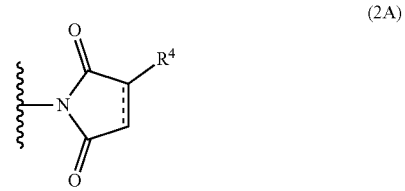

(2A)

(2B)

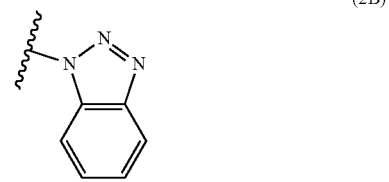

(2C)

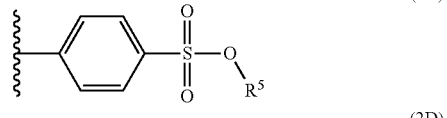

(2D)

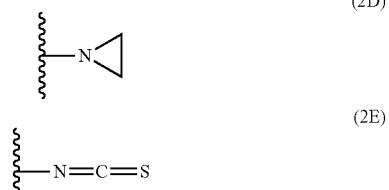

(2E)

(wherein $R^4$ represents a hydrogen atom or a sulfo group, $R^5$ represents an optionally substituted alkyl group, and the bond indicated by a solid line and a dashed line represents a single bond or a double bond).

Examples of the alkyl group represented by $R^5$ in formula (2C) may be the same as described above. The same applies to the kind and number of substituents.

The amine reactive group or thiol reactive group that satisfies such conditions preferably has an amine reactive end or a thiol reactive end via a linking group, such as a group represented by —O—, —COO—, or —CONR$^6$—(wherein R$^6$ represents a hydrogen atom or an alkyl group described above) (in particular, —COO—). This facilitates the phosphole compound of the present invention to function as a protein labeling agent (in particular, an antibody labeling agent) and have a higher fluorescence quantum yield even in environments containing large amounts of water. Specific examples of such amine reactive groups or thiol reactive groups include

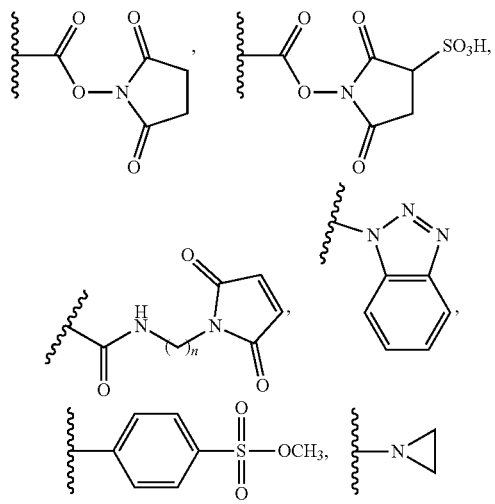

(wherein n is an integer of 1 to 6).

In the above formula, n is preferably an integer of 1 to 6, and more preferably an integer of 1 to 4.

Among these, from the viewpoint of ease of synthesis and ease of labeling a protein (in particular, an antibody), the amine reactive group is preferably

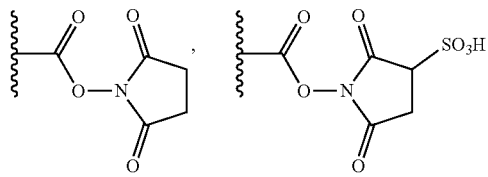

and the like, and the thiol reactive group is preferably

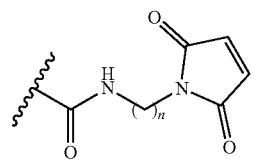

(wherein n is as defined above).

From the viewpoint of decreasing energy difference between the HOMO level (energy level of the highest unoccupied molecular orbital) and the LUMO level (energy level of the lowest unoccupied molecular orbital) and increasing the absorption peak wavelength and the fluorescence peak wavelength, as well as increasing the fluorescence quantum yield and achieving a high fluorescence quantum yield even in environments containing large amounts of water, phosphole compounds represented by formula (1B):

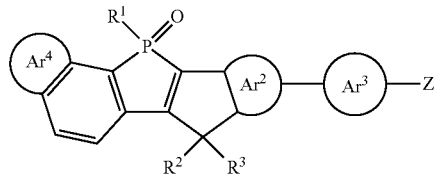

(1B)

(wherein Ar$^2$, Ar$^3$, Ar$^4$, R$^1$, R$^2$, R$^3$, and Z are as defined above) are preferable. Phosphole compounds represented by formula (1B1):

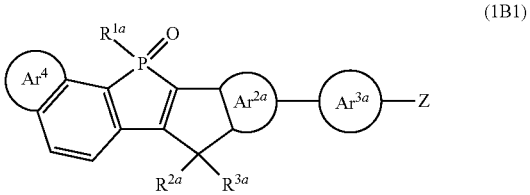

(1B1)

(wherein Ar$^{2a}$ represents an optionally substituted aromatic hydrocarbon ring, Ar$^{3a}$ represents an optionally substituted arylene group, R$^{1a}$ represents an optionally substituted aryl group, R$^{2a}$ and R$^{3a}$ are the same or different and each represent aryl substituted with alkoxy, and Ar$^4$ is as defined above) are more preferable, and phosphole compounds described in the Examples below are even more preferable.

The phosphole compound of the present invention may be a hydrate or a solvate of the phosphole compound represented by formula (1). The hydrate and solvate are both included within the scope of the present invention.

2. Method for Producing Phosphole Compound

The method for producing the phosphole compound of the present invention is not particularly limited. For example, the phosphole compound represented by formula (1C) wherein Z is an amine reactive group or a thiol reactive group:

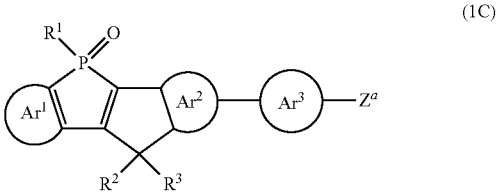

(1C)

(wherein Ar$^1$, Ar$^2$, Ar$^3$, R$^1$, R$^2$, and R$^3$ are as defined above and Z$^a$ represents an amine reactive group or a thiol reactive group) is preferably synthesized in accordance with the following Reaction Scheme 1:

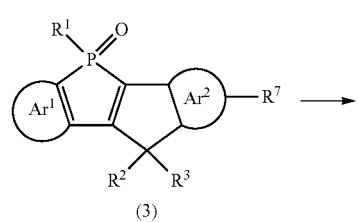

(3)

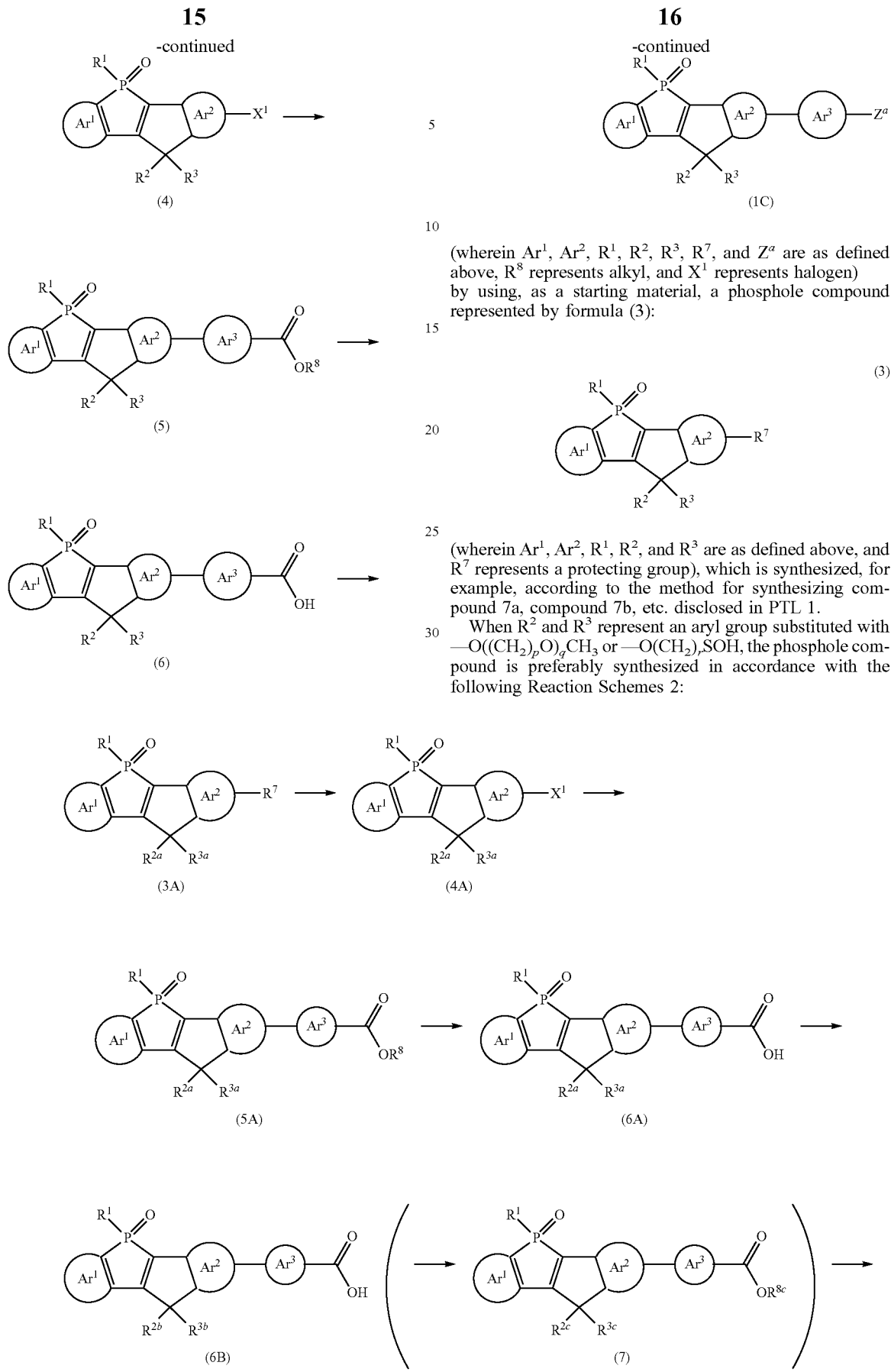

(wherein $Ar^1$, $Ar^2$, $R^1$, $R^2$, $R^3$, $R^7$, and $Z^a$ are as defined above, $R^8$ represents alkyl, and $X^1$ represents halogen) by using, as a starting material, a phosphole compound represented by formula (3):

(wherein $Ar^1$, $Ar^2$, $R^1$, $R^2$, and $R^3$ are as defined above, and $R^7$ represents a protecting group), which is synthesized, for example, according to the method for synthesizing compound 7a, compound 7b, etc. disclosed in PTL 1.

When $R^2$ and $R^3$ represent an aryl group substituted with —O((CH$_2$)$_p$O)$_q$CH$_3$ or —O(CH$_2$)$_r$SOH, the phosphole compound is preferably synthesized in accordance with the following Reaction Schemes 2:

-continued

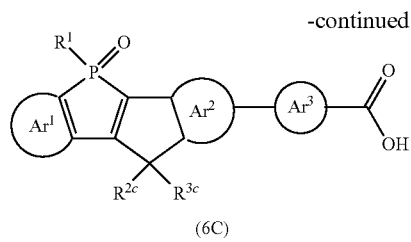

(6C)

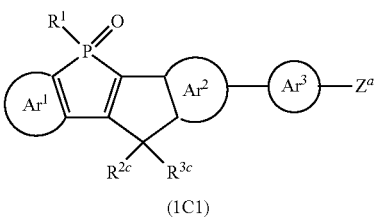

(1C1)

(wherein $Ar^1$, $Ar^2$, $R^1$, $R^7$, $R^8$, $X^1$, and $Z^a$ are as defined above; $R^{2a}$ and $R^{3a}$ are the same or different and each represent an aryl group substituted with a group represented by $-OR^9$ (wherein $R^9$ represents an alkyl group described above, in particular, methyl in consideration of ease of performing subsequent steps); $R^2$ and $R^{3b}$ are the same or different and each represent a hydroxy-substituted aryl group; $R^{2c}$, $R^{3c}$ and $R^{8c}$ are the same or different and each represent an aryl group substituted with $-O((CH_2)_pO)_qCH_3$ or $-O(CH)_rSO_3H$ (wherein p, q, and r are as defined above).

Examples of alkyl groups represented by $R^8$ and $R^9$ in Reaction Schemes 1 and 2 may be the same as described above. The same applies to the kind and number of substituents.

Examples of halogen atoms represented by $X^1$ in Reaction Schemes 1 and 2 include chlorine, bromine, iodine, and the like.

Examples of aryl groups in Reaction Scheme 2 may be the same as above.

(2-1) Compound (3)→Compound (4), or Compound (3A)→Compound (4A)

In this step, the protective group at the end of compound (3) or compound (3A) is preferably haloganated with a halogenating agent.

Examples of the halogenating agent include iodine ($I_2$), iodine monochloride (ICl), iodine trichloride ($ICl_3$), N-iodosuccinimide (NIS), bromine ($Br_2$), N-bromosuccinimide (NBS), chlorine ($Cl_2$), and the like. The amount of halogenating agent to be used is preferably 1 to 5 moles (in particular, 1.5 to 3 moles) per mole of the compound (3) or compound (3A).

The reaction can be usually performed in the presence of a reaction solvent. Examples of the reaction solvents include aliphatic halogenated hydrocarbons such as dichloromethane, dichloroethane, chloroform, and carbon tetrachloride; amide solvents such as dimethylformamide; and the like. From the viewpoint of ease of synthesis, yield, etc., halogenated hydrocarbons are preferable, and dichloromethane is more preferable. These reaction solvents can be used singly or in a combination of two or more.

In general, the reaction atmosphere can be an inert gas atmosphere (argon gas atmosphere, nitrogen gas atmosphere, etc.). The reaction can be performed with heating, at ordinary temperature, or with cooling. In general, the reaction temperature is preferably −50 to 100° C., and more preferably 0 to 50° C. The reaction time is not particularly limited and is preferably a period during which the reaction sufficiently proceeds.

After completion of the reaction, a purification process can also be performed by a usual method, if necessary. Alternatively, the subsequent step can be performed without performing a purification process.

(2-2) Compound (4)→Compound (5), or Compound (4A)→Compound (5A)

In this step, compound (4) or compound (4A) obtained in step (2-1) and a compound represented by formula (8):

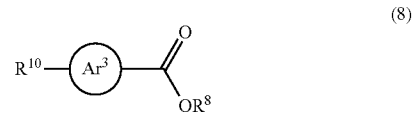

(wherein $Ar^3$ and $R^8$ are as defined above, and $R^{10}$ represents a boronic acid or a boronic acid ester group) are subjected to a Suzuki-Miyaura coupling reaction to obtain compound (5) or compound (5A).

Examples of the boronic acid or the boronic acid ester group represented by $R^{10}$ in formula (8) include groups represented by formula (9):

(wherein the two $R^{11}$ are the same or different and represent a hydrogen atom or an optionally substituted alkyl group, and the two $R^{11}$ may link together and form a ring with $-O-N-O-$ adjacent thereto).

Examples of the alkyl group represented by $R^{11}$ in formula (9) may be the same as described above. The same applies to the kind and number of substituents.

Examples of the boronic acid or the boronic acid ester group represented by $R^{10}$ include, for example,

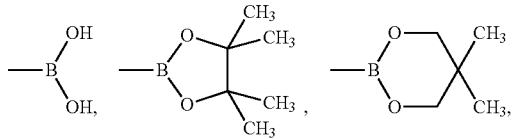

and the like.

In general, the amount of compound (8) to be used is preferably 1 to 5 moles (in particular, 1.5 to 3 moles) per mole of compound (4) or compound (4A).

In this step, a palladium catalyst that is usually used in Suzuki-Miyaura coupling is used. Specific examples include palladium acetate ($Pd(OAc)_2$), tetrakis(triphenylphosphine) palladium (0) ($Pd(PPh_3)_4$), palladium trifluoroacetate, palladium chloride, palladium bromide, palladium iodide, tris (dibenzylieneacetone)dipalladium (0) ($Pd_2(dba)_3$), and the like. In this step, from the viewpoint of synthesis, yield, etc., tetrakis(triphenylphosphine)palladium (0) (Pd(PPh$_3$)$_4$) is preferable. In general, the amount of palladium catalyst to be used is preferably 0.01 to 0.3 moles, and more preferably 0.02 to 0.1 moles, per mole of compound (4) or compound (4A).

In this step, a ligand compound can also be used, if necessary. As the ligand compound, a ligand compound usually used in Suzuki-Miyaura coupling can be used in an amount usually used.

In this step, a base can be used, if necessary. Examples of the base include potassium fluoride, cesium fluoride, sodium hydroxide, potassium hydroxide, sodium carbonate, potassium carbonate, cesium carbonate, potassium phosphate, sodium acetate, potassium acetate, calcium acetate, and the like. In this step, potassium phosphate is preferable from the viewpoint of yield and ease of synthesis. From the viewpoint of ease of synthesis, yield, etc., the amount of base to be used is preferably 1 to 20 moles, and more preferably 3 to 10 moles, per mole of compound (4) or compound (4A).

The reaction can usually be performed in the presence of a reaction solvent. Examples of usable reaction solvents include ethers, such as diethyl ether, diisopropyl ether, tetrahydrofuran (THF), 1,4-dioxane, dimethoxyethane (DME), diglyme, cyclopentylmethyl ether (CPME), tert-butyl methyl ether (TBME), and anisole; aromatic hydrocarbons, such as benzene, toluene, and xylene; aliphatic halogenated hydrocarbons, such as dichloromethane, dichloroethane, chloroform, and carbon tetrachloride; nitrile solvents, such as acetonitrile; amide solvents, such as dimethylformamide; and the like. From the viewpoint of ease of synthesis, yield, etc., aromatic hydrocarbons are preferable, and toluene is more preferable. These reaction solvents can be used singly or in a combination of two or more. A mixed solvent of such an organic solvent and water can also be used.

In general, the reaction atmosphere can be an inert gas atmosphere (argon gas atmosphere, nitrogen gas atmosphere, etc.). The reaction can be performed with heating, at ordinary temperature, or with cooling. In general, the reaction temperature is preferably 0 to 150° C., and more preferably 50 to 100° C. The reaction time is not particularly limited and is preferably a period during which the reaction sufficiently proceeds.

After completion of the reaction, a purification process can also be performed by a usual method, if necessary. Alternatively, the subsequent step can be performed without performing a purification process.

(2-3) Compound (5)→Compound (6), or Compound (5A) →Compound (6A)

In this step, compound (5) or compound (5A) is hydrolyzed with an acid catalyst to obtain compound (6) or compound (6A).

The acid catalyst to be used for hydrolysis may be, for example, an acid commonly used for hydrolysis of ester. When R$^8$ is a less reactive group, such as t-butyl, a strong acid, such as trifluoroacetic acid or hydrochloric acid, is preferably used. Since the acid catalyst is usually a liquid, the acid catalyst is preferably used in an excess amount.

The reaction can be usually used in the presence of a reaction solvent. Examples of usable reaction solvents include ethers, such as diethyl ether, diisopropyl ether, tetrahydrofuran (THF), 1,4-dioxane, dimethoxyethane (DME), diglyme, cyclopentylmethyl ether (CPME), tert-butyl methyl ether (TBME), and anisole; aromatic hydrocarbons, such as benzene, toluene, and xylene; aliphatic halogenated hydrocarbons, such as dichloromethane, dichloroethane, chloroform, and carbon tetrachloride; nitrile solvents, such as acetonitrile; amide solvents, such as dimethylformamide; and the like. From the viewpoint of, for example, ease of synthesis and yield, ether and aliphatic halogenated hydrocarbon are preferable, and anisole and dichloromethane are more preferable. These reaction solvents can be used singly or in a combination of two or more.

In general, the reaction atmosphere can be an inert gas atmosphere (argon gas atmosphere, nitrogen gas atmosphere, etc.). The reaction can be performed with heating, at ordinary temperature, or with cooling. In general, the reaction temperature is preferably –50 to 100° C., and more preferably 0 to 50° C. The reaction time is not particularly limited and is preferably a period during which the reaction sufficiently proceeds.

After completion of the reaction, a purification process can also be performed by a usual method, if necessary. Alternatively, the subsequent step can be performed without performing a purification process.

(2-4) Compound (6A)→Compound (6B)

In this step, compound (6B) can be obtained by dealkylating compound (6A) with a Lewis acid.

Examples of Lewis acids include boron tribromide, aluminum tribromide, boron trichloride, aluminum trichloride, titanium tetrachloride, tin tetrachloride, boron trifluoride, iodotrimethyl silane, silicon tetrachloride, and the like. These Lewis acids can be used singly or in a combination of two or more. Since Lewis acid is usually a liquid, Lewis acid is preferably used in an excess amount relative to the amount of compound (6A).

The reaction can be usually performed in the presence of a reaction solvent. Examples of usable reaction solvents include aromatic hydrocarbons, such as benzene, toluene, and xylene; aliphatic halogenated hydrocarbons, such as dichloromethane, dichloroethane, chloroform, and carbon tetrachloride; nitrile solvents, such as acetonitrile; amide solvents, such as dimethylformamide; and the like. From the viewpoint of, for example, ease of synthesis and yield, aliphatic halogenated hydrocarbons are preferable, and dichloromethane is more preferable. These reaction solvents can be used singly or in a combination of two or more.

In general, the reaction atmosphere can be an inert gas atmosphere (e.g., argon gas atmosphere, nitrogen gas atmosphere). The reaction can be performed with heating, at ordinary temperature, or with cooling. In general, the reaction temperature is preferably –50 to 100° C., and more preferably 0 to 50° C. The reaction time is not particularly limited and is preferably a period during which the reaction sufficiently proceeds.

After completion of the reaction, a purification process can also be performed by a usual method, if necessary. Alternatively, the subsequent step can be performed without performing a purification process.

(2-5) Compound (6B)→Compound (7) or Compound (6C)

In this step, compound (6B) is reacted with a compound represented by formula (10A):

(wherein p and q are as defined above, and R$^{12}$ represents tosyl), or a compound represented by formula (10B):

(wherein $R^{13}$ represents an optionally substituted alkylene group) to esterify the carboxy group and, if necessary, further etherify phenolic hydroxyl groups to obtain compound (7) or compound (6C). When compound (10A) is used, compound (7) is obtained. When compound (10B) is used, compound (6C) is obtained. Accordingly, when compound (10B) is used, step (2-6) described below can be skipped.

Examples of the alkylene group represented by $R^{13}$ in formula (10B) include $C_{1-6}$ (in particular, $C_{2-4}$) alkylene groups. Examples include methylene, ethylene, trimethylene, tetramethylene, and the like. The alkylene group may have one or more substituents. Examples of substituents include, but are not limited to, alkyl groups described above, cycloalkyl groups described above, aryl groups described above, heteroaryl groups described above, alkenyl groups (e.g., vinyl, propenyl), alkynyl groups (e.g., ethynyl, 1-propynyl), alkoxy groups described above, carbonyl, cyano, nitro, halogen atoms (e.g., fluorine, chlorine, bromine, iodine), and the like. When the alkylene group has one or more substituents, the number of substituents is preferably, but not limited to, 1 to 6, and more preferably 1 to 3.

In general, the amount of compound (10A) or compound (10B) is preferably 2 to 20 moles, and more preferably 3 to 10 moles, per mole of compound (6B).

In this step, a base can also be used, if necessary. Examples of usable bases include ammonium chloride, potassium fluoride, cesium fluoride, sodium hydroxide, potassium hydroxide, sodium methoxide, sodium hydrogen carbonate, potassium hydrogen carbonate, sodium carbonate, potassium carbonate, cesium carbonate, potassium phosphate, sodium acetate, potassium acetate, calcium acetate, and the like. These bases can be used singly or in a combination of two or more. In this step, potassium carbonate is preferable from the viewpoint of yield and ease of synthesis. When a base is used, the amount of base to be used is preferably 3 to 50 moles, and more preferably 5 to 20 moles, per mole of compound (6B), from the viewpoint of ease of synthesis, yield, etc.

The reaction can be usually performed in the presence of a reaction solvent. Examples of the reaction solvent include ethers, such as diethyl ether, diisopropyl ether, tetrahydrofuran (THF), 1,4-dioxane, dimethoxyethane (DME), diglyme, cyclopentylmethyl ether (CPME), tert-butyl methyl ether (TBME), and anisole; aromatic hydrocarbons, such as benzene, toluene, and xylene; aliphatic halogenated hydrocarbons, such as dichloromethane, dichloroethane, chloroform, and carbon tetrachloride; nitrile solvents such as acetonitrile; amide solvents, such as dimethylformamide; and the like. From the viewpoint of ease of synthesis, yield, etc., nitrile solvents are preferable, and acetonitrile is more preferable. These reaction solvents can be used singly or in a combination of two or more.

In general, the reaction atmosphere can be an inert gas atmosphere (argon gas atmosphere, nitrogen gas atmosphere, etc.). The reaction can be performed with heating, at ordinary temperature, or with cooling. It is usually more preferable that the reaction is performed under reflux. The reaction time is not particularly limited and is preferably a period during which the reaction sufficiently proceeds.

After completion of the reaction, a purification process can also be performed by a usual method, if necessary. Alternatively, the subsequent step can be performed without performing a purification process.

(2-6) Compound (7)→Compound (6C)

In this step, compound (7) is hydrolyzed using a base catalyst to obtain compound (6C).

The base catalyst to be used for the hydrolysis may be a base catalyst commonly used in hydrolysis of ester. Lithium hydroxide is preferable. Since the base catalyst is usually a liquid, the base catalyst is preferably used in an excess amount.

The reaction can usually be performed in the presence of a reaction solvent. Examples of usable reaction solvents include ethers, such as diethyl ether, diisopropyl ether, tetrahydrofuran (THF), 1,4-dioxane, dimethoxyethane (DME), diglyme, cyclopentyl methyl ether (CPME), tert-butyl methyl ether (TBME), and anisole; aromatic hydrocarbons, such as benzene, toluene, and xylene; aliphatic halogenated hydrocarbons, such as dichloromethane, dichloroethane, chloroform, and carbon tetrachloride; nitrile solvents, such as acetonitrile; amide solvents, such as dimethylformamide; and the like. From the viewpoint of ease of synthesis, yield, etc., ether is preferable, and tetrahydrofuran is more preferable. These reaction solvents can be used singly or in a combination of two or more.

In general, the reaction atmosphere can be an inert gas atmosphere (argon gas atmosphere, nitrogen gas atmosphere, etc.). The reaction can be performed with heating, at ordinary temperature, or with cooling. In general, the reaction temperature is preferably −50 to 100° C., and more preferably 0 to 50° C. The reaction time is not particularly limited and is preferably a period during which the reaction sufficiently proceeds.

After completion of the reaction, a purification process can also be performed by a usual method, if necessary. Alternatively, the subsequent step can be performed without performing a purification process.

(2-7) Compound (6)→Compound (1C), or Compound (6C) →Compound (1C1)

In this step, the carboxy group of compound (6) or compound (6C) can be replaced with a desired reactive group by a usual method. In this replacement, a condensing agent can be used. Examples of usable condensing agents include carbodiimide condensing agents (N,N'-dicyclohexylcarbodiimide, 1-(3-dimethylaminopropyl)-3-ethylcarbodiimide hydrochloride, and diisopropylcarbodiimide), imidazole condensing agents (carbonyldiimidazole and 2-chloro-1,3-dimethylimidazolinium chloride), triazine condensing agents (4-(4,6-dimethoxy-1,3,5-triazin-2-yl)-4-methylmorpholinium chloride), phosphonium condensing agents (benzotriazol-1-yloxy-trisdimethylaminophosphonium salts, (benzotriazol-1-yloxy)tripyrrolidinophosphonium hexafluorophosphorate), uronium condensing agents ({{[(1-cyano-2-ethoxy-2-oxoethylidene)amino]oxy}-4-morpholinomethylene}dimethyl ammonium hexafluorophosphate, O-benzotriazol-1-yl)-N,N,N',N'-tetramethyluronium hexafluorophosphate, 0-(7-azabenzotriazol-1-yl)-N,N,N',N'-tetramethyluronium hexafluorophosphate, succinimide condensing agents (N-hydroxysuccinimide, N,N,N',N'-tetramethyl-O—(N-succinimidyl)uronium tetrafluoroborate (TSTU)), and the like. For example, a phosphole compound of the present invention having a succinimide skeleton (compound (1C) or compound (1C1)) at the end can be obtained by reacting N-hydroxysuccinimide, TSTU, etc. The thus obtained phosphole compound of the present invention having a succinimide skeleton at the end can function as a protein labeling agent (in particular, an antibody labeling agent).

In general, the amount of condensing agent to be used is preferably 1 to 5 moles, and more preferably 1.5 to 3 moles, per mole of compound (6) or compound (6C).

In this step, a carbodiimide reagent is preferably used as a coupling reagent. Examples of carbodiimide reagents include dicyclohexylcarbodiimide (DCC), 1-(3-dimethylaminopropyl)-3-ethylcarbodiimide (EDC), and the like. These carbodiimide reagents can be used singly or in a combination of two or more. These usable carbodiimide reagents may be, for example, in the form of hydrochloride or like salts (e.g., 1-(3-dimethylaminopropyl)-3-ethylcarbodiimide hydrochloride (EDCI)). In general, the amount of coupling reagent to be used is preferably 1 to 5 moles, and more preferably 1.5 to 3 moles, per mole of compound (6) or compound (6C).

Since a hydrochloride (an acid salt) may be used as the coupling agent in this step, a base is preferably used. Examples of such bases include pyridine, dialkylaminopyridine (e.g., 4-dimethylaminopyridine (DMAP)), and the like. Such bases can be used singly or in a combination of two or more. In general, the amount of base to be used is preferably 1 to 5 moles, and more preferably 1.5 to 3 moles, per mole of compound (6) or compound (6C).

The reaction can be performed in the presence of a reaction solvent. Examples of usable reaction solvents include ethers, such as diethyl ether, diisopropyl ether, tetrahydrofuran (THF), 1,4-dioxane, dimethoxyethane (DME), diglyme, cyclopentylmethyl ether (CPME), tert-butyl methyl ether (TBME), and anisole; aromatic hydrocarbons, such as benzene, toluene, and xylene; aliphatic halogenated hydrocarbons, such as dichloromethane, dichloroethane, chloroform, and carbon tetrachloride; nitrile solvents, such as acetonitrile; amide solvents, such as dimethylformamide; and the like. From the viewpoint of ease of synthesis, yield, etc., amide solvents are preferable, and dimethylformamide is more preferable. These reaction solvents can be used singly or in a combination of two or more.

In general, the reaction atmosphere can be an inert gas atmosphere (argon gas atmosphere, nitrogen gas atmosphere, etc.). The reaction can be performed with heating, at ordinary temperature, or with cooling. In general, the reaction temperature is preferably −50 to 100° C., and more preferably 0 to 50° C. The reaction time is not particularly limited and is preferably a period during which the reaction sufficiently proceeds.

After completion of the reaction, a purification process can be performed by a usual method, if necessary, to thereby obtain the phosphole compound of the present invention.

When the phosphole compound of the present invention thus obtained has a succinimide skeleton at the end, this phosphole compound can be reacted with a maleimide compound, such as N-(2-aminoethyl) maleimide, to thereby obtain a phosphole compound of the present invention having a maleimide skeleton at the end. The maleimide compound to be used may be in the form of a salt, such as trifluoroacetate.

In general, the amount of maleimide compound to be used is preferably 0.2 to 5 moles, and more preferably 0.5 to 2 moles, per mole of compound (1C) or compound (1C1).

Since trifluoroacetate (an acid salt) may be used as the maleimide compound in this step, a base is preferably used. Examples of usable bases include pyridine, dialkylaminopyridines (e.g., 4-dimethylaminopyridine (DMAP)), amines (e.g., triethylamine), and the like. These bases can be used singly or in a combination of two or more. The base is preferably used in an excess amount per mole of compound (1C) or compound (1C1).

The reaction can be usually performed in the presence of a reaction solvent. Examples of usable reaction solvents include ethers, such as diethyl ether, diisopropyl ether, tetrahydrofuran (THF), 1,4-dioxane, dimethoxyethane (DME), diglyme, cyclopentylmethyl ether (CPME), tert-butyl methyl ether (TBME), and anisole; aromatic hydrocarbons, such as benzene, toluene, and xylene; aliphatic halogenated hydrocarbons, such as dichloromethane, dichloroethane, chloroform, and carbon tetrachloride; nitrile solvents, such as acetonitrile; amide solvents, such as dimethylformamide; dimethyl sulfoxide (DMSO); and the like. From the viewpoint of ease of synthesis, yield, etc., dimethyl sulfoxide is preferable. These solvents can be used singly or in a combination of two or more.

In general, the reaction atmosphere can be an inert gas atmosphere (argon gas atmosphere, nitrogen gas atmosphere, etc.). The reaction can be performed with heating, at ordinary temperature, or with cooling. In general, the reaction temperature is preferably −50 to 100° C., and more preferably 0 to 50° C. The reaction time is not particularly limited and is preferably a period during which the reaction sufficiently proceeds.

After completion of the reaction, a purification process can be performed by a usual method, if necessary, to thereby obtain the phosphole compound of the present invention.

An example of the method for synthesizing the phosphole compound of the present invention according to one embodiment is described above. However, the synthesis method is not limited to the above production method. Various synthesis methods can be used to synthesize the phosphole compound.

3. Fluorescent Dye and Protein Labeling Agent

The fluorescent dye of the present invention comprises the phosphole compound of the present invention described above.

The fluorescent dye of the present invention, which has a fused phosphole skeleton, has excellent light resistance (photostablity) and can have various reactive groups (Z) introduced via $Ar^3$. Further, due to $Ar^3$ functioning as a mediator in this manner, the fluorescent dye of the present invention can have a high fluorescence quantum yield even in environments containing large amounts of water.

Various substituents can be introduced as the reactive group (Z) at the end. For example, when an amine reactive group, a thiol reactive group, or the like is introduced, the resulting compound can be used as a protein labeling agent (in particular, an antibody labeling agent) that labels a protein (in particular, an antibody), and a decrease in fluorescence brightness is inhibited even during repeated imaging. Therefore, the fluorescent dye of the present invention is suitable for repeated super-resolution microscopy (in particular, stimulated emission depletion (STED) microscopy) observation, such as in vivo stimulated emission depletion (STED) imaging.

When the phosphole compound of the present invention is used as a protein labeling agent (in particular, an antibody labeling agent), examples of target proteins (in particular, antibodies) include avidin, streptavidin, annexin V, anti-IgG antibody, anti-IgM antibody, anti-CD3 antibody, anti-CD4 antibody, anti-CD20 antibody, anti-CD25 antibody, anti-CD43 antibody, anti-CD44 antibody, anti-CD68 antibody, anti-IFN-γ antibody, anti-TNF-α antibody, anti-Ly-6G antibody, anti-Ku70 antibody, anti-IL-4 antibody, anti-IL-17 antibody, anti-IL-31 antibody, anti-Notch1 antibody, anti-Notch3 antibody, anti-FOXBP3 antibody, anti-Ki-67 antibody, anti-HLA-A2 antibody, anti-α-tubulin antibody, anti-cathepsin D antibody, anti-angiotensin antibody, anti-COX1 antibody, anti-GLUT1 antibody, anti-AKT1/2/3 antibody, anti-Apg3 antibody, anti-3 catenin antibody, anti-CDK5 antibody, anti-CEA antibody, anti-HER2 antibody, and the like.

When the phosphole compound wherein the reactive group represented by Z is an amine reactive group or a thiol reactive group among the phosphole compounds of the present invention is used as a protein labeling agent (in particular, an antibody labeling agent), the protein labeling agent (in particular, the antibody labeling agent) of the present invention comprises the phosphole compound of the present invention and is preferably in the form of a solution obtained by dissolving the phosphole compound in an organic solvent. From the viewpoint of exhibiting an enhanced fluorescence quantum yield even in environments containing large amounts of water while enhancing light resistance, the content of the phosphole compound of the present invention is preferably $1 \times 10^{-8}$ to $1 \times 10^{-4}$ mol/L, and more preferably $1 \times 10^{-7}$ to $1 \times 10^{-5}$ mol/L.

When the fluorescent dye (phosphole compound) of the present invention is used as a protein labeling agent (in particular, an antibody labeling agent) in the form of a solution, examples of usable organic solvents include, but are not limited to, both polar solvents and nonpolar solvents.

Examples of polar solvents include ether compounds (tetrahydrofuran, anisole, 1,4-dioxane, cyclopentyl methyl ether, etc.), alcohols (methanol, ethanol, allyl alcohol, etc.), ester compounds (ethyl acetate etc.), ketones (acetone etc.), halogenated hydrocarbons (dichloromethane, chloroform, etc.), dimethyl sulfoxide, amide solvents (N,N-dimethylformamide, dimethylacetamide, 1,3-dimethyl-2-imidazolidinone, N-methylpyrrolidone, etc.), nitrile solvents (acetonitrile etc.), and the like.

Examples of nonpolar solvents include aliphatic organic solvents, such as pentane, hexane, cyclohexane, and heptane; aromatic solvents, such as benzene, toluene, xylene, and mesitylene; and the like.

Since the phosphole compound of the present invention can fluoresce in various solvents in this way, a fluorescent dye comprising the phosphole compound of the present invention is a highly versatile dye.

The protein labeling agent (in particular, antibody labeling agent) of the present invention is preferably in the form of a solution, as described above. In in vivo observation, a pH of about 5 to 11 is preferable, and a pH of about 6.5 to 7.5 is more preferable. To adjust the pH, a buffer (such as HEPES buffer, tris buffer, tricine-sodium hydroxide buffer, phosphate buffer, or phosphate-buffered physiological saline) or the like can also be used together.

EXAMPLES

The present invention is specifically described with reference to Examples. However, the present invention is not limited to these examples.

In the Examples, the melting point (mp) or decomposition temperature was measured with a Yanaco MP-S3 apparatus. $^1$H NMR spectrum, $^{13}$C {$^1$H}NMR spectrum, and $^{31}$P {$^1$H}NMR were determined in CDCl$_3$ or DMSO-d$_6$ used as a solvent with a JEOL AL-400 ($^1$H: 400 MHz, $^{13}$C: 100 MHz, $^{31}$P: 162 MHz) or JEOL A-600 spectrometer ($^1$H: 600 MHz, $^{13}$C: 150 MHz, $^{13}$P: 243 MHz). Chemical shifts are expressed in δ ppm. $^1$H NMR spectra were measured using signals of CHCl$_3$ (7.26 ppm), CH$_2$Cl$_2$ (5.30 ppm), acetone (2.05 ppm), and DMSO (2.50 ppm) as internal standards. $^{13}$C NMR spectra were determined using signals of CDCl$_3$ (77.16 ppm), CD$_2$Cl$_2$ (53.84 ppm), and DMSO-d$_6$ (39.52 ppm) as internal standards. For $^{31}$P NMR, H$_3$PO$_4$ (0.00 ppm) was used as an external standard. Mass spectra were determined with a Bruker micrOTOF Focus spectrometry system by the atmospheric pressure chemical ionization method (APCI). Thin layer chromatography (TLC) was performed on a glass plate to which silica gel 60F$_{254}$ (Merck) had been applied to a thickness of 0.25 mm. Column chromatography was performed using a PSQ100B neutral silica gel (produced by Fuji Silysia Chemical Ltd.). Recycling preparative high-performance liquid chromatography (HPLC) was performed using an LC-918 (produced by Japan Analytical Industry Co., Ltd.) equipped with a reverse-phase column (Wakosil-II 5C18 HG Prep), or a YMC LC-forte/R equipped with a reverse-phase column (YMC-DispoPackAT ODS). All reactions were performed in a nitrogen atmosphere unless otherwise specified. Commercially available products were used as solvents and reagents without purification unless otherwise specified. Anhydrous tetrahydrofuran (THF), toluene, diethyl ether (Et$_2$d) and CH$_2$Cl$_2$ were purchased from Kanto Chemical Co., Inc., and purified using Glass Contour Solvent Systems. 2-Bromo-3-iodonaphthalene (Cottet, F. et al., Synthesis, 5, 798-803 (2005)), 1-bromonaphthalen-2-yl triflate (Weimar, M. et al. Org. Lett., 15, 1706-1709 (2013)), and (4-trimethylsilylphenyl)acetylene (Wu, J. et al. J. Org. Chem., 69, 8194-8204 (2004)) were synthesized according to the method previously described.

Synthesis Example 1: Synthesis of Compound 1 (1-bromo-2-(4-trimethylsilylphenylethynyl)naphthalene)

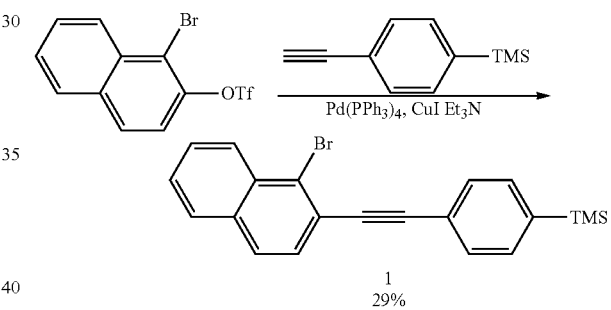

(wherein Tf represents trifluoromethane sulfonyl, TMS represents trimethylsilyl, Pd(PPh$_3$)$_4$ represents tetrakis(triphenylphosphine) palladium (0), and Et$_3$N represents triethylamine; the same applies below). A solution of 1-bromonaphthalen-2-yl triflate (99.44 g, 280 mmol) and 4-trimethylsilylphenylacetylene (48.80 g, 280 mmol) in triethylamine (Et$_3$N; 500 mL) was degassed by bubbling dry nitrogen gas for 20 minutes. After tetrakis(triphenylphosphine)palladium (0) (Pd(PPh$_3$)$_4$; 3.24 g, 2.80 mmol) and CuI (0.533 g, 2.80 mmol) were added, the mixture was stirred at 60° C. for 20 hours. After the mixture was cooled to room temperature, the resulting inorganic salt was removed by filtration, and the filtrate was washed with toluene (200 mL). After all volatile substances were distilled off under reduced pressure, the residue was separated by silica gel column chromatography (hexane, Rf=0.24), and the obtained crude product was recrystallized with methanol (MeOH; 100 mL) to obtain 30.50 g of the desired compound 1 as a white powder (80.4 mmol, yield: 29%).

Mp: 95.0-95.5° C. $^1$H NMR (400 MHz, CDCl$_3$): δ 8.33 (d, J=8.8 Hz, 1H), 7.82 (d, J=8.0 Hz, 1H), 7.77 (d, J=8.4 Hz, 1H), 7.64-7.59 (m, 4H), 7.56-7.52 (m, 3H), 0.31 (s, 9H); $^{13}$C{$^1$H} NMR (100 MHz, CDCl$_3$): δ 141.78 (C), 133.77 (C), 133.41 (CH), 132.39 (C), 130.91 (CH), 129.11 (CH), 128.33 (CH), 128.02 (CH), 127.93 (CH), 127.61 (CH), 127.28 (CH), 126.65 (C), 123.62 (C), 123.42 (C), 95.04 (C), 89.91 (C), −1.09 (CH). HRMS (APCI): m/z calcd. for $C_{21}H_{20}BrSi$: 379.0512 ([M+H]$^+$); found. 379.0513.

Synthesis Example 2: Synthesis of Compound 2 (3-bromo-1-phenyl-2-(4-trimethylsilylphenyl)naphtho[1,2-b]phosphole-P-oxide)

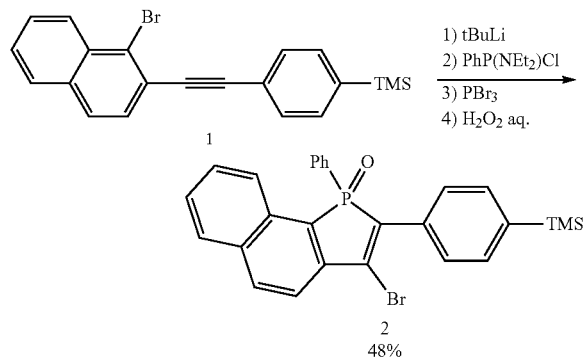

(In the formula, tBuLi represents tert-butyl lithium, PhP(NEt$_2$)Cl represents chloro(phenyl)(diethylamino)phosphine, PBr$_3$ represents phosphorus tribromide, and Ph represents phenyl; the same applies below.)

A 1.60M pentane solution (100.5 mL) of tert-butyl lithium (tBuLi) (160.8 mmol) was added dropwise to a solution of compound 1 of Synthesis Example 1 (30.50 g, 80.4 mmol) in anhydrous tetrahydrofuran (THF; 400 mL) at −78° C. After the mixture was stirred at −78° C. for 1 hour, the resulting suspension was slowly warmed up to −40° C. over 2 hours. After the mixture was cooled to −78° C., chloro(phenyl)(diethylamino)phosphine (PhP(NEt$_2$)Cl; 15.5 mL, 80.5 enol) was added thereto over 0.5 hours. The obtained mixture was slowly warmed up to 0° C. over 0.5 hours. After the mixture was cooled again to −78° C., phosphorus tribromide (PBr$_3$; 7.64 mL, 80.4 enol) was added over 0.5 hours. The obtained mixture was warmed up to room temperature. After substantially all pentane (about 100 mL) was distilled off, the resulting mixture was refluxed at 80° C. for 48 hours. After cooling, substantially all volatile substances were distilled off under reduced pressure. The residue was diluted with ethyl acetate (EtOAc; 100 mL). A hydrogen peroxide solution (10 mL, 30%) was added, and the resulting mixture was stirred at 0° C. for 1 hour. The reaction was quenched with an aqueous Na$_2$SO$_3$ solution (100 mL, 10%) at 0° C., and the mixture was extracted twice with ethyl acetate (EtOAc; 300 mL). The combined organic layers were washed with saturated saline (100 mL), then dried over anhydrous Na$_2$SO$_4$ and filtered. The filtrate was concentrated under reduced pressure. The obtained solid was purified by silica gel column chromatography (CH$_2$Cl$_2$→10:1 CH$_2$Cl$_2$/ethyl acetate) and recrystallization with methanol (MeOH; 100 mL) to obtain 19.48 g of the desired compound 2 as a yellow solid (38.7 mmol, yield: 48%).

Mp: 119.5-120.5° C. $^1$H NMR (400 MHz, CDCl$_3$): δ 8.12 (d, J=8.4 Hz, 1H), 8.06-8.04 (m, 1H), 7.91-7.87 (m, 2H), 7.82-7.71 (m, 4H), 7.54-7.43 (m, 5H), 7.38 (td, J=7.6 Hz, J=3.2 Hz, 2H), 0.26 (s, 9H); $^{13}$C{$^1$H} NMR (100 MHz, CDCl$_3$): δ 141.81 (s, C), 140.76 (d, J=21.4 Hz, C), 136.94 (d, J=87.4 Hz, C), 134.33 (d, J=1.6 Hz, CH), 134.11 (d, J=8.2 Hz, C), 133.59 (s, CH), 132.60 (d, J=3.3 Hz, CH), 132.37 (d, J=8.3 Hz, C), 132.08 (d, J=37.2 Hz, C), 131.12 (d, J=9.0 Hz, C), 130.94 (d, J=10.7 Hz, CH), 129.19 (d, J=12.3 Hz, CH), 129.06 (d, J=99.8 Hz, C), 128.92 (s, CH), 128.87 (s, CH), 127.71 (d, J=5.0 Hz, CH), 127.41 (s, CH), 127.03 (d, J=103.1 Hz, C), 125.77 (d, J=5.0 Hz, CH), 121.80 (d, J=11.6 Hz, CH), −1.13 (s, CH); $^{31}$P{$^1$H} NMR (162 MHz, CDCl$_3$): δ 35.57. HRMS (APCI): m/z calcd. for $C_{27}H_{25}BrOPSi$: 503.0590 ([M+H]$^+$); found. 503.0609.

Synthesis Example 3: Synthesis of Compound 3

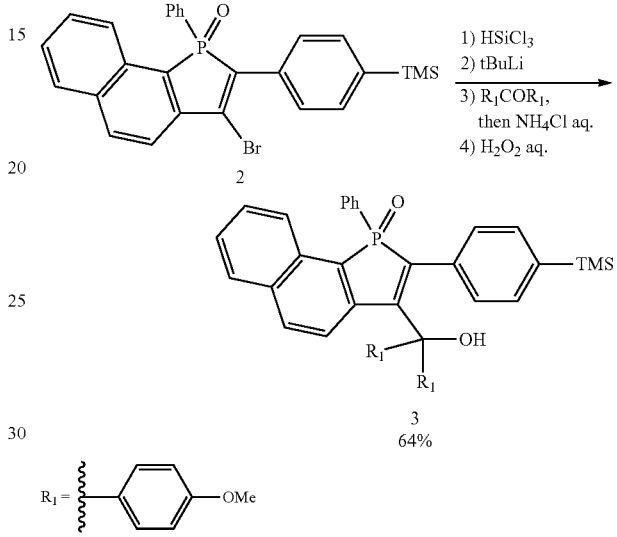

(wherein Me represents methyl; the same applies below).

HSiCl$_3$ (8.07 mL, 80.0 mmol) was added at once to a suspension of compound 2 obtained in Synthesis Example 2 (10.07 g, 20.0 mmol) in anhydrous toluene (30 mL). After the resulting mixture was stirred at 50° C. for 1 hour, all volatiles were distilled off under reduced pressure. Toluene (20 mL) was then added to the resulting mixture, and the obtained suspension was filtered through Celite (registered trademark). The filtrate was washed with toluene (10 mL). After the filtrate was concentrated under reduced pressure, the obtained white solid was suspended in anhydrous diethyl ether (Et$_2$O; 100 mL). A 1.60M pentane solution (25.0 mL) of tert-butyl lithium (tBuLi) (40.0 mmol) was added to this suspension at −78° C. over 30 minutes. After the resulting mixture was stirred at the same temperature for 2 hours, 4,4'-dimethoxybenzophenone (4.85 g, 20.0 mmol) was added, and the obtained mixture was slowly warmed to room temperature overnight. The reaction was then quenched with a saturated aqueous NH$_4$Cl solution (50 mL), and a hydrogen peroxide solution (10 mL, 30%) was added. The resulting mixture was stirred at room temperature for 0.5 hours. After the reaction was quenched with a 10% aqueous Na$_2$SO$_3$ solution (100 mL) at 0° C., the mixture was extracted with CHCl$_3$ (2000 mL). The organic layer was washed with saturated saline (200 mL), then dried over anhydrous Na$_2$SO$_4$ and filtered. The filtrate was concentrated under reduced pressure, and the obtained crude product was purified by recrystallization from toluene (200 mL) twice to obtain 8.50 g of the desired compound 3 as a white solid (12.7 mmol, yield: 64%).

Mp: 269.0-270.0° C. $^1$H NMR (600 MHz, DMSO-d$_6$, 100° C.): δ 7.90-7.83 (m, 4H), 7.66-7.62 (m, 2H), 7.52 (t,

J=7.2 Hz, 1H), 7.48-7.43 (m, 4H), 7.24 (d, J=8.4 Hz, 2H), 7.19 (d, J=8.4 Hz, 2H), 6.97 (d, J=7.8 Hz, 2H), 6.67-6.62 (m, 6H), 6.51 (s, 1H), 3.68 (s, 6H), 0.17 (s, 9H); $^{31}P\{^{1}H\}$ NMR (162 MHz, DMSO-d$_6$, 100° C.): δ 39.16. HRMS (APCI): m/z calcd. for $C_{42}H_{40}O_4PSi$: 667.2428 ([M+H]$^+$); found. 667.2395.

Synthesis Example 4: Synthesis of Compound 4

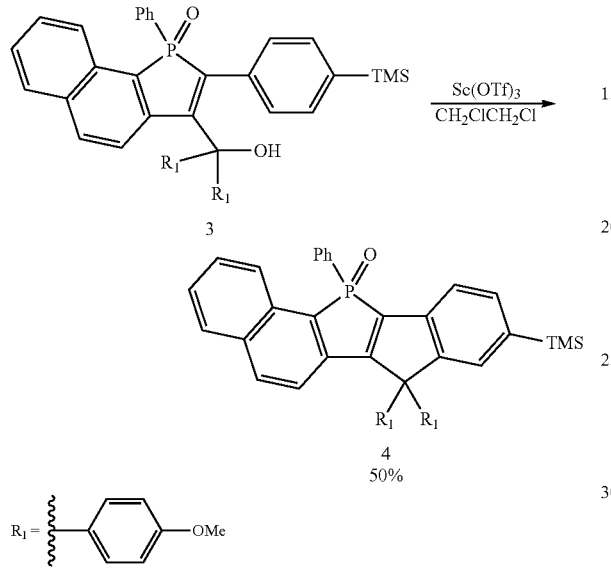

(wherein Sc(OTf)$_3$ represents scandium trifluoromethanesulfonate (III); the same applies below).

A solution of a mixture of compound 3 obtained in Synthesis Example 3 (8.180 g, 12.27 mmol) and scandium trifluoromethanesulfonate (III)(Sc(OTf)$_3$; 6.039 g, 12.27 mmol) was stirred at room temperature. After 48 hours of stirring, H$_2$O (200 mL) was added to quench the reaction. The organic phase was separated, and the aqueous phase was extracted with CHCl$_3$ (500 mL). The combined organic layer was washed with H$_2$O (200 mL), then dried over anhydrous Na$_2$SO$_4$, and filtered. The filtrate was concentrated under reduced pressure. The obtained solid was purified by silica gel column chromatography (CH$_2$Cl$_2$→10:1 CH$_2$Cl$_2$/ethyl acetate, Rf=0.31 in 10:1 CH$_2$Cl$_2$/ethyl acetate) and subsequent recrystallization from ethanol (20 mL) to obtain 3.99 g of the desired compound 4 as a yellow solid (6.15 mmol, yield: 50%).

Mp: 239.0-240.5° C. $^1$H NMR (400 MHz, CDCl$_3$): δ 8.12 (d, J=7.6 Hz, 1H), 7.86-7.80 (m, 3H), 7.75 (d, J=8.0 Hz, 1H), 7.53-7.38 (m, 11H), 7.24 (d, J=8.8 Hz, 2H), 6.86 (d, J=8.8 Hz, 2H), 6.81 (d, J=8.8 Hz, 2H), 3.78 (s, 3H), 3.77 (s, 3H), 0.20 (s, 9H); $^{13}C\{^{1}H\}$ NMR (100 MHz, CDCl$_3$): δ 168.09 (d, J=22.2 Hz, C), 159.01 (s, C), 158.95 (s, C), 156.44 (d, J=9.9 Hz, C), 139.77 (s, C), 138.78 (d, J=103.9 Hz, C), 137.71 (d, J=12.4 Hz, C), 133.43 (d, J=8.3 Hz, C), 133.31 (d, J=2.5 Hz, CH), 133.01 (s, C), 132.76 (s, CH), 132.72 (d, J=106.4 Hz, C), 132.58 (d, J=9.0 Hz, C), 132.48 (s, C), 130.86 (d, J=11.6 Hz, CH), 130.05 (d, J=102.3 Hz, C), 129.91 (s, CH), 129.85 (s, CH), 129.19 (d, J=12.4 Hz, CH), 129.07 (s, CH), 128.75 (s, CH), 128.33 (s, CH), 126.82 (s, CH), 125.30 (d, J=5.0 Hz, CH), 121.32 (s, CH), 114.13 (s, CH), 113.99 (s, CH), 65.23 (d, J=11.5 Hz, C), 55.33 (s, CH), 55.31 (s, CH), −0.89 (s, CH). One of the doublet signals of a quaternary carbon paired with the signal at 138.07 ppm, one of the doublet signals of a CH carbon paired with the signal at 132.45 ppm, and one of the doublet signals of a CH carbon paired with the signal at 121.23 ppm may be overlapped with other signals; $^{31}P\{^{1}H\}$ NMR (162 MHz, CDCl$_3$): δ 23.73. HRMS (APCI): m/z calcd. for $C_{42}H_{38}O_3PSi$: 649.2322 ([M+H]$^+$); found. 649.2325.

Synthesis Example 5: Synthesis of Compound 5

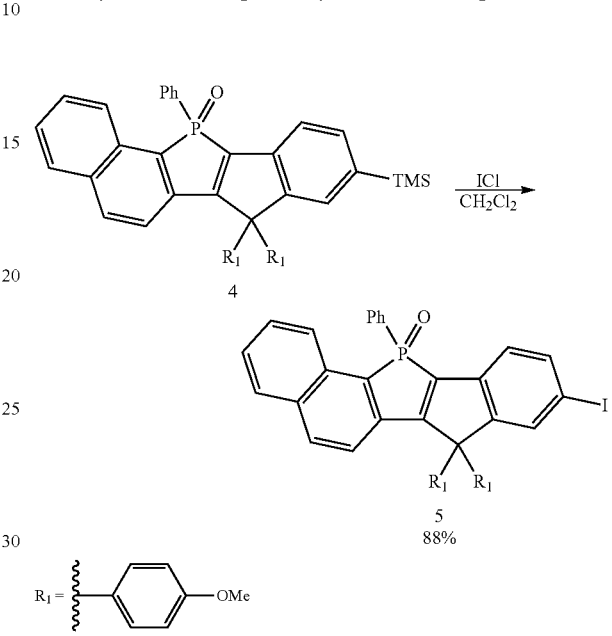

A 1.00 M CH$_2$Cl$_2$ solution (12.16 mL) of iodine monochloride (ICl) (12.16 mmol) was added at 0° C. to an anhydrous CH$_2$Cl$_2$ (50 mL) solution of compound 4 (3.945 g, 6.08 mmol) obtained in Synthesis Example 4, and the resulting mixture was stirred at room temperature for 2 hours. After the reaction was quenched with a 5% aqueous Na$_2$S$_2$O$_3$ solution (100 mL), the organic phase was separated, and the aqueous phase was extracted with CHCl$_3$ (200 mL). The combined organic layer was washed with H$_2$O (50 mL), then dried over anhydrous Na$_2$SO$_4$ and filtered. After the filtrate was concentrated under reduced pressure, the obtained solid was purified by silica gel column chromatography (CH$_2$Cl$_2$→10:1 CH$_2$Cl$_2$/ethyl acetate, Rf=0.29 in 10:1 CH$_2$Cl$_2$/ethyl acetate) and subsequent recrystallization from ethanol (20 mL) to obtain 3.782 g of the desired compound 5 as a yellow solid (5.38 mmol, yield: 88%).

Mp: >300° C. $^1$H NMR (400 MHz, CDCl$_3$): δ 8.11 (d, J=8.4 Hz, 1H), 7.83-7.78 (m, 3H), 7.74 (d, J=8.0 Hz, 1H), 7.69 (s, 1H), 7.57 (dd, J=8.0 Hz, J=1.6 Hz, 1H), 7.52-7.34 (m, 8H), 7.25-7.20 (m, 3H), 6.86 (d, J=8.8 Hz, 2H), 6.82 (d, J=8.8 Hz, 2H), 3.78 (s, 3H), 3.77 (s, 3H); $^{13}C\{^{1}H\}$ NMR (100 MHz, CDCl$_3$): δ 168.19 (d, J=21.4 Hz, C), 159.23 (s, C), 159.21 (d, J=9.1 Hz, C), 159.14 (s, C), 137.89 (d, J=103.9 Hz, C), 137.58 (d, J=18.2 Hz, C), 136.81 (s, CH), 136.64 (d, J=11.5 Hz, C), 133.75 (s, CH), 133.48 (s, CH), 132.79 (d, J=107.2 Hz, C), 132.63 (d, J=2.5 Hz, CH), 132.53 (d, J=9.9 Hz, C), 131.90 (s, C), 131.37 (s, C), 130.76 (d, J=11.6 Hz, CH), 129.80 (s, CH), 129.74 (s, CH), 129.65 (d, J=102.3 Hz, C), 129.25 (d, J=12.4 Hz, CH), 128.77 (s, CH), 128.43 (s, CH), 127.00 (s, CH), 125.24 (d, J=5.8 Hz, CH), 123.44 (s, CH), 121.19 (d, J=10.7 Hz, CH), 114.35 (s, CH), 114.18 (s, CH), 92.79 (s, C), 65.28 (d, J=10.7 Hz, C), 55.36

(s, CH), 55.33 (s, CH). One of the doublet signals of a quaternary carbon paired with the signal at 133.57 ppm may be overlapped; $^{31}P\{^1H\}$ NMR (162 MHz, CDCl$_3$): δ 23.43. HRMS (APCI): m/z calcd. for C$_{39}$H$_{29}$IO$_3$P: 703.0894 ([M+H]$^+$); found. 703.0890.

Example 1: Synthesis of Compound 6

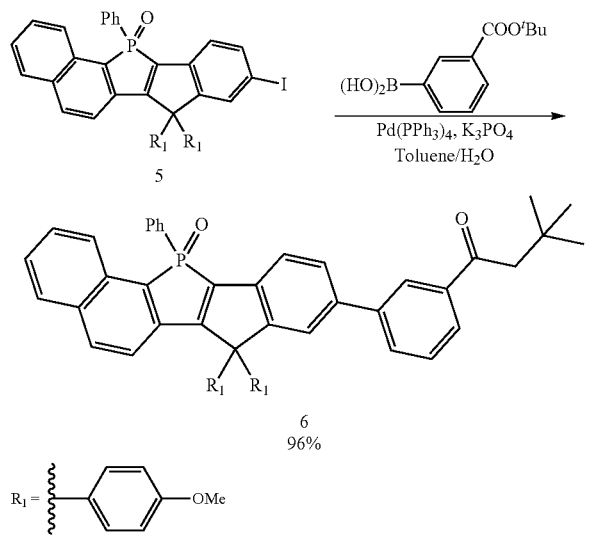

(In the reaction scheme, tBu represents tert-butyl; the same applies below.)

A solid of compound 5 obtained in Synthesis Example 5 (1.405 g, 2.00 mmol), 3-(tert-butoxycarbonyl)phenylboronic acid (0.888 g, 4.00 mmol), tetrakis(triphenylphosphine)palladium (0) (Pd(PPh$_3$)$_4$; 0.116 g, 0.100 mmol) and K$_3$PO$_4$ (2.547 g, 12.0 mmol) were added to a mixed solvent of degassed toluene (24 mL) and H$_2$O (6 mL). The resulting mixture was stirred at 80° C. for 12 hours. After the mixture was cooled to room temperature, the organic phase was separated, and the water phase was extracted with ethyl acetate (EtOAc; 50 mL). The combined organic layer was washed with H$_2$O (20 mL) and saturated saline (20 mL), then dried over anhydrous Na$_2$SO$_4$ and filtered. After the filtrate was concentrated under reduced pressure, the obtained solid was purified by silica gel column chromatography (2:1→1:1 hexane/ethyl acetate, Rf=0.29 in 1:1 hexane/ethyl acetate) to obtain 1.444 g of the desired compound 6 as a yellow solid (1.92 mmol, yield: 96%).

Mp: 177.0-179.0° C. $^1$H NMR (400 MHz, CDCl$_3$): δ 8.16-8.13 (m, 2H), 7.94-7.83 (m, 4H), 7.76 (d, J=8.4 Hz, 1H), 7.66-7.64 (m, 2H), 7.60 (d, J=7.6 Hz, 1H), 7.54-7.38 (m, 10H), 7.31 (d, J=8.8 Hz, 2H), 6.87 (d, J=8.8 Hz, 2H), 6.84 (d, J=8.4 Hz, 2H), 3.77 (s, 3H), 3.76 (s, 3H), 1.61 (s, 9H); $^{13}$C$\{^1$H$\}$ NMR (100 MHz, CDCl$_3$): δ 168.43 (d, J=21.4 Hz, C), 165.69 (s, C), 159.11 (s, C), 159.04 (s, C), 158.26 (d, J=9.1 Hz, C), 141.18 (s, C), 139.49 (s, C), 138.28 (d, J=103.9 Hz, C), 138.04 (d, J=18.2 Hz, C), 136.66 (d, J=11.6 Hz, C), 133.44 (d, J=9.0 Hz, C), 133.43 (d, J=1.7 Hz, CH), 132.83 (s, C), 132.55 (d, J=3.3 Hz, CH), 132.50 (s, C), 132.15 (s, C), 131.19 (s, CH), 130.84 (d, J=10.7 Hz, CH), 129.90 (d, J=101.4 Hz, C), 129.87 (s, CH), 129.83 (s, CH), 129.24 (d, J=12.4 Hz, CH), 128.76 (s, CH), 128.70 (s, CH), 128.37 (s, CH), 128.28 (s, CH), 128.17 (s, CH), 126.87 (s, CH), 125.25 (d, J=5.0 Hz, CH), 123.51 (s, CH), 122.26 (s, CH), 121.22 (d, J=10.7 Hz, CH), 114.26 (s, CH), 114.12 (s, CH), 81.23 (s, C), 65.38 (d, J=10.7 Hz, C), 55.32 (s, CH), 55.30 (s, CH), 28.24 (s, CH). One of the doublet signals of a quaternary carbon paired with the signal at 133.20 ppm, one of the doublet signals of a quaternary carbon paired with the signal at 132.61 ppm, and one singlet signal of a CH carbon may be overlapped; $^{31}$P$\{^1$H$\}$ NMR (162 MHz, CDCl$_3$): δ 23.73. HRMS (APCI): m/z calcd. for C$_{50}$H$_{42}$O$_5$P: 753.2764 ([M+H]$^+$); found. 753.2749.

Example 2: Synthesis of Compound 7

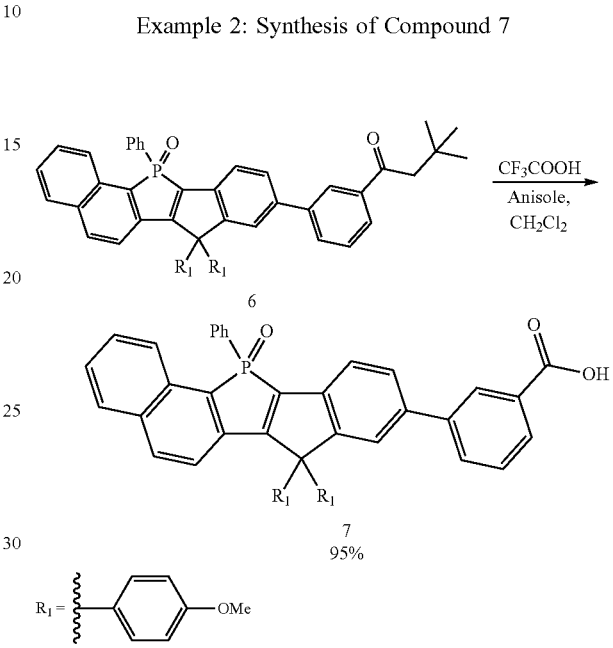

Anisole (2 mL) and trifluoroacetic acid (TFA; 5 mL) were added in this order to a CH$_2$Cl$_2$ (20 mL) solution of compound 6 (1.400 g, 1.86 mmol) obtained in Example 1. The resulting mixture was stirred at room temperature for 4 hours. After all volatiles were distilled off under reduced pressure, the obtained solid was purified by silica gel column chromatography (CHCl$_3$→5:1 CHCl$_3$/ethyl acetate, Rf=0.04 in 5:1 CHCl$_3$/ethyl acetate) and recrystallization from ethyl acetate (10 mL) to obtain 1.230 g of the desired compound 7 as a yellow solid (1.77 mmol, yield: 95%).

Mp: 231.0-233.0° C. $^1$H NMR (400 MHz, CDCl$_3$): δ 8.25 (s, 1H), 8.16 (d, J=8.0 Hz, 1H), 8.05 (d, J=7.6 Hz, 1H), 7.94-7.84 (m, 3H), 7.76 (d, J=8.4 Hz, 1H), 7.68-7.63 (m, 3H), 7.54-7.38 (m, 10H), 7.31 (d, J=9.2 Hz, 2H), 6.87-6.83 (m, 4H), 3.77 (s, 3H), 3.74 (s, 3H); $^{13}$C$\{^1$H$\}$ NMR (100 MHz, CDCl$_3$): δ 170.19 (s, C), 168.80 (d, J=21.5 Hz, C), 159.15 (s, C), 159.09 (s, C), 158.28 (d, J=9.9 Hz, C), 141.35 (s, C), 139.39 (s, C), 138.15 (d, J=18.9 Hz, C), 137.90 (d, J=104.8 Hz, C), 136.66 (d, J=11.5 Hz, C), 133.64 (s, CH), 133.50 (d, J=9.1 Hz, C), 132.75 (d, J=1.6 Hz, CH), 132.59 (d, J=9.1 Hz, C), 132.59 (s, C), 132.27 (d, J=107.3 Hz, C), 132.07 (s, C), 132.04 (s, CH), 130.98 (d, J=10.7 Hz, CH), 130.69 (s, C), 129.91 (s, CH), 129.87 (s, CH), 129.36 (d, J=12.3 Hz, CH), 129.02 (s, CH), 128.92 (s, CH), 128.81 (s, CH), 128.69 (s, CH), 128.51 (s, CH), 127.02 (s, CH), 126.98 (s, CH), 125.32 (d, J=5.8 Hz, CH), 123.46 (s, CH), 122.43 (s, CH), 121.28 (d, J=10.7 Hz, CH), 114.36 (s, CH), 114.20 (s, CH), 65.50 (d, J=10.7 Hz, C), 55.36 (s, CH), 55.34 (s, CH). One doublet signals of a quaternary carbon may be overlapped; $^{31}$P$\{^1$H$\}$ NMR (162 MHz, CDCl$_3$): δ 25.01. HRMS (APCI): m/z calcd. for C$_{46}$H$_{34}$O$_5$P: 697.2138 ([M+H]$^+$); found. 697.2140.

Example 3: Synthesis of Compound 8

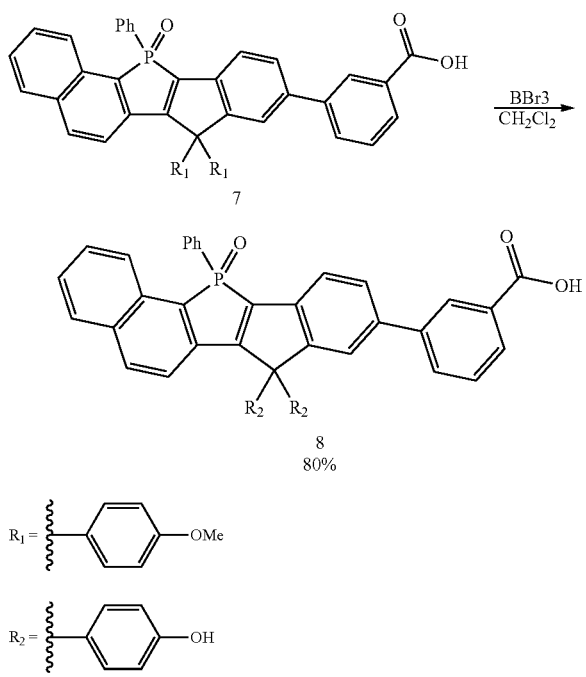

Boron tribromide (BBr$_3$; 1.38 mL, 14.3 mmol) was added dropwise at −78° C. to an anhydrous CH$_2$Cl$_2$ (30 mL) solution of compound 7 obtained in Example 2 (500 mg, 0.718 mmol). The resulting mixture was slowly warmed to room temperature overnight. The reaction was quenched with H$_2$O (20 mL) at 0° C., and the mixture was extracted with ethyl acetate (300 mL). The resulting organic layer was washed with saturated saline (50 mL) 3 times, then dried over anhydrous Na$_2$SO$_4$, and filtered. After the filtrate was concentrated under reduced pressure, the obtained solid was purified by silica gel column chromatography (ethyl acetate→10:3 ethyl acetate/methanol) and HPLC (2:1 ethyl acetate/methanol) to obtain 382 mg of the desired compound 8 as a yellow solid (0.571 mmol, yield: 80%).

$^1$H NMR (400 MHz, DMSO): δ 9.68 (br, 1H), 8.11 (s, 1H), 8.06 (d, J=8.0 Hz, 1H), 7.99 (d, J=8.4 Hz, 1H), 7.93 (d, J=8.0 Hz, 2H), 7.83-7.78 (m, 4H), 7.66-7.43 (m, 9H), 7.28 (d, J=8.4 Hz, 2H), 7.20 (d, J=8.4 Hz, 2H), 6.8246.78 (m, 4H), 3.53 (br, 2H); $^{13}$C{$^1$H} NMR (100 MHz, DMSO): δ 168.68 (d, J=21.4 Hz, C), 167.29 (s, C), 158.75 (d, J=9.1 Hz, C), 156.94 (s, C), 156.92 (s, C), 140.24 (s, C), 138.65 (s, C), 137.56 (d, J=182 Hz, C), 137.22 (d, J=103.1 Hz, C), 136.13 (d, J=12.4 Hz, C), 133.79 (s, CH), 133.00 (d, J=8.2 Hz, C), 132.92 (s, CH), 132.31 (d, J=104.8 Hz, C), 131.76 (s, C), 131.61 (d, J=9.0 Hz, C), 131.24 (s, CH), 130.29 (d, J=10.7 Hz, CH), 130.12 (s, C), 130.04 (s, C), 129.74 (d, J=100.7 Hz, C), 129.63 (d, J=12.4 Hz, CH), 129.51 (s, CH), 129.37 (s, CH), 129.18 (s, CH), 128.71 (s, CH), 128.41 (s, CH), 127.47 (s, CH), 127.11 (s, CH), 126.80 (s, CH), 124.28 (d, J=5.8 Hz, CH), 123.12 (s, CH), 121.65 (s, CH), 121.29 (d, J=11.6 Hz, CH), 115.76 (s, CH), 115.74 (s, CH), 65.86 (d, J=9.9 Hz, C). One singlet signal of a CH carbon may be overlapped; $^{31}$P{$^1$H} NMR (162 MHz, DMSO): δ 21.65.

Example 4: Synthesis of Compound 9

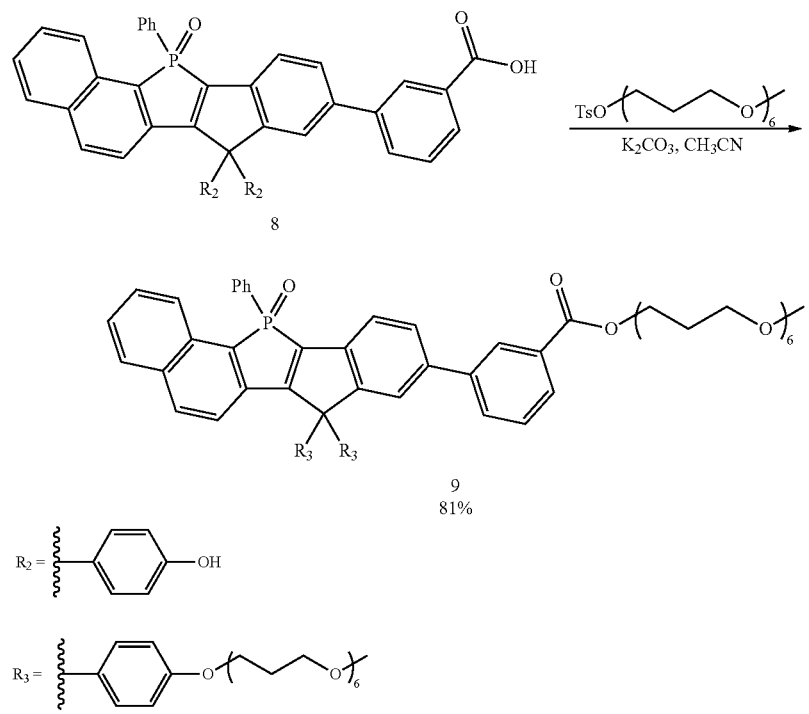

(In the reaction scheme, Ts represents tosyl; the same applies below.)

An anhydrous CH$_3$CN (3 mL) solution of compound 8 obtained in Example 3 (200 mg, 0.299 mmol), hexa(ethylene glycol)monomethyl ether tosilate (676 mg, 1.50 mmol), and K$_2$CO$_3$ (415 mg, 3.00 mmol) was refluxed for 48 hours. After cooling to room temperature, the mixture was diluted with ethyl acetate (EtOAc; 50 mL), washed with saturated saline (15 mL) 3 times, then dried over anhydrous Na$_2$SO$_4$, and filtered. After the filtrate was concentrated under reduced pressure, the obtained oily substance was purified by silica gel column chromatography (CHCl$_3$→50:1 CHCl$_3$/methanol) to obtain 366 mg of the desired compound 9 as a highly viscous oily substance (0.243 mmol, yield: 81%).

$^1$H NMR (600 MHz, CDCl$_3$): δ 8.11 (s, 1H), 8.04 (d, J=7.8 Hz, 1H), 7.90 (d, J=7.2 Hz, 1H), 7.78-7.75 (m, 3H), 7.68 (d, J=8.4 Hz, 1H), 7.59 (d, J=7.8 Hz, 1H), 7.54 (s, 1H), 7.50 (d, J=7.8 Hz, 1H), 7.44-7.41 (m, 2H), 7.38-7.30 (m, 8H), 7.19 (d, J=7.8 Hz, 2H), 6.81 (d, J=7.2 Hz, 2H), 6.77 (d, J=7.2 Hz, 2H), 4.42-4.38 (m, 2H), 4.04-3.98 (m, 4H), 3.77-3.72 (m, 6H), 3.61-3.54 (m, 54H), 3.46-3.41 (m, 6H), 3.27-3.25 (m, 9H); $^{13}$C{$^1$H} NMR (150 MHz, CDCl$_3$): δ 168.16 (d, J=21.6 Hz, C), 166.10 (s, C), 158.06 (s, C), 158.00 (s, C), 141.03 (s, C), 138.95 (s, C), 137.93 (d, J 104.3 Hz, C), 136.48 (d, J=11.9 Hz, C), 133.15 (s, CH), 133.14 (d, J=7.8 Hz, C), 132.37 (d, J=106.8 Hz, C), 132.37 (s, C), 132.26 (s, CH), 132.22 (d, J=11.1 Hz, C), 131.90 (s, C), 131.46 (s, CH), 130.46 (d, J=11.1 Hz, CH), 130.37 (s, C), 129.61 (d, J=101.4 Hz, C), 129.52 (s, CH), 129.45 (s, CH), 128.94 (d, J=12.3 Hz, CH), 128.59 (s, CH), 128.50 (s, CH), 128.18 (s, CH), 128.04 (s, CH), 128.01 (s, CH), 126.64 (s, CH), 126.56 (s, CH), 124.88 (d, J=5.0 Hz, CH), 123.12 (s, CH), 121.93 (s, CH), 120.90 (d, J=11.1 Hz, CH), 114.63 (a, CH), 114.47 (s, CH), 71.65 (s, CH), 70.52 (s, CH), 70.44 (s, CH), 70.38 (s, CH), 70.35 (s, CH), 70.33 (s, CH), 70.30 (s, CH), 70.22 (s, CH), 69.37 (s, CH), 69.35 (s, CH), 68.90 (s, CH), 67.16 (s, CH), 67.14 (s, CH), 65.80 (d, J=11.1 Hz, C), 63.99 (s, CH), 58.73 (s, CH). One of the doublet signals of a quaternary carbon paired with the signal at 157.92 ppm, one of the doublet signals of a quaternary carbon paired with the signal at 137.71 ppm, and twenty four singlet signal of an alkyl CH carbon may be overlapped; $^{31}$P{$^1$H} NMR (243 MHz, CDCl$_3$): δ 23.39.

Example 5: Synthesis of Compound 10

(In the reaction scheme, THF represents tetrahydrofuran; the same applies below.)

Lithium hydroxide monohydrate (LiOH.H$_2$O; 1.00 g, 23.8 mmol) was added to a solution of compound 9 (350 mg, 0.233 mmol) obtained in Example 4 in tetrahydrofuran (THF; 10 mL) and H$_2$O (10 mL). After stirring at room temperature for 16 hours, the mixture was acidified with hydrochloric acid (1M, 30 mL). The mixture was extracted with ethyl acetate (EtOAc; 200 mL) twice. The combined organic layer was washed with saturated saline (50 mL) 3 times, then dried over anhydrous Na$_2$SO$_4$, and filtered. After the filtrate was concentrated under reduced pressure, the obtained oily substance was purified by silica gel column chromatography (CHCl$_3$→20:1 CHCl$_3$/methanol) to obtain 267 mg of the desired compound 10 as a highly viscous oily substance (0.218 mmol, yield: 94%).

$^1$H NMR (400 MHz, CDCl$_3$): δ 8.23 (s, 1H), 8.13 (d, J=8.4 Hz, 1H), 8.00 (d, J=7.6 Hz, 1H), 7.90-7.83 (m, 3H), 7.75 (d, J=8.0 Hz, 1H), 7.65-7.60 (m, 3H), 7.50 (t, J=7.2 Hz, 2H), 7.45-7.36 (m, 8H), 7.27 (d, J=8.4 Hz, 2H), 6.88-6.83 (m, 4H), 4.10-4.06 (m, 4H), 3.83-3.79 (m, 4H), 3.70-3.60 (m, 36H), 3.53-3.49 (m, 4H), 3.34 (s, 3H), 3.33 (s, 3H); $^{13}$C{$^1$H} NMR (100 MHz, CDCl$_3$): δ 168.45 (d, J=22.3 Hz, C), 168.42 (s, C), 158.12 (s, C), 158.07 (s, C), 157.98 (d, J=9.1 Hz, C), 140.96 (s, C), 139.20 (s, C), 137.84 (d, J=19.0 Hz, C), 137.66 (d, J=104.7 Hz, C), 136.35 (d, J=12.4 Hz, C), 133.40 (d, J=2.5 Hz, CH), 133.23 (d, J=9.1 Hz, C), 132.52 (s, CH), 132.43 (s C), 132.29 (d, J=9.1 Hz, C), 131.95 (s. C), 131.44 (s, CH), 130.84 (s, C), 130.65 (d, J=11.5 Hz, CH), 129.61 (s, CH), 129.54 (s, CH), 129.09 (d, J=12.3 Hz, CH), 128.62 (s, CH), 128.30 (s, CH), 128.23 (s, CH), 126.76 (s, CH), 126.72 (s, CH), 124.99 (d, J=4.9 Hz, CH), 123.18 (s, CH), 122.10 (s, CH), 121.00 (d, J=9.1 Hz, CH), 114.75 (s, CH), 114.58 (s, CH), 71.71 (s, CH), 70.58 (s, CH), 70.41 (s, CH), 70.37 (s, CH), 70.35 (s, CH), 70.27 (s, CH), 69.45 (s, CH), 67.22 (s, CH), 65.22 (d, J=10.8 Hz, C), 58.81 (s, CH). Two doublet signals of an aromatic quaternary carbon, two singlet signal of an aromatic CH carbon, and seventeen singlet signal of an alkyl CH carbon may be overlapped; $^{31}$P{$^1$H} NMR (162 MHz, CDCl$_3$): δ 24.69.

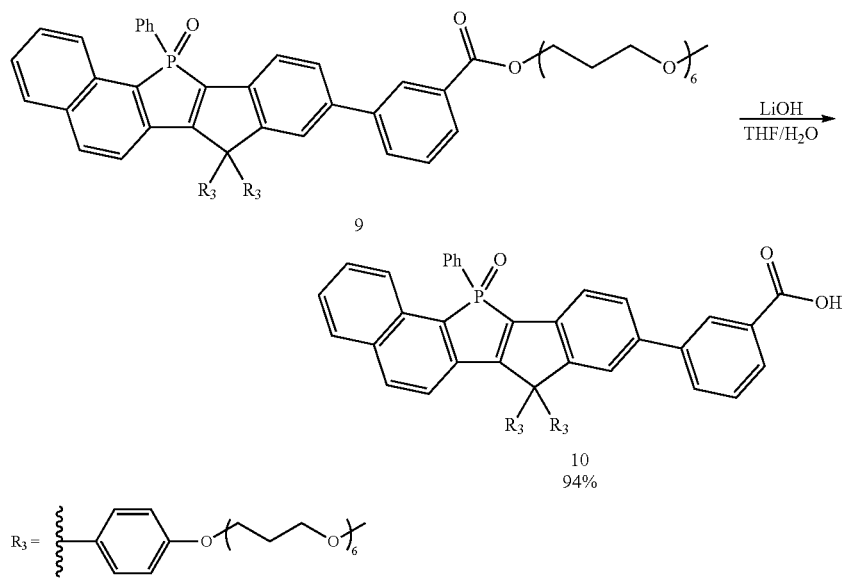

Example 6: Synthesis of Compound 11 (Phox 430 NHS Ester)

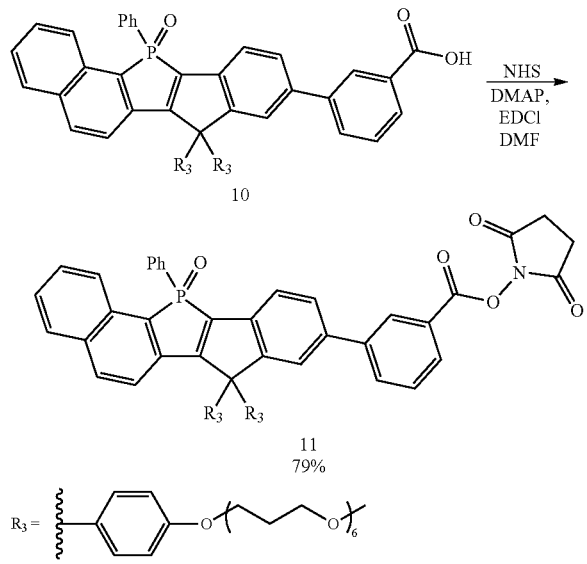

(in the formula, NHS represents N-hydroxysuccinimide, DMAP represents N,N-dimethyl-4-aminopyridine, EDCI represents 1-ethyl-3-(3-dimethylaminopropyl) carbodiimide hydrochloride, and DMF represents dimethylformamide; the same applies below).

1-Ethyl-3-(3-dimethylaminopropyl)carbodiimide hydrochloride (EDCI; 56.4 mg, 0.294 mmol) was added to a solution of compound 10 (180 mg, 0.147 mmol) obtained in Example 5, N-hydroxysuccinimide (NHS; 33.8 mg, 0.294 mmol), and N,N-dimethyl-4-aminopyridine (DMAP; 35.9 mg, 0.294 mmol) in anhydrous dimethylformamide (DMF; 5 mL). After stirring at room temperature for 4 hours, the resulting mixture was diluted with ethyl acetate (EtOAc; 50 mL), washed with saturated saline (15 mL) 3 times, then dried over anhydrous $Na_2SO_4$, and filtered. After the filtrate was concentrated under reduced pressure, the obtained oily substance was purified by silica gel column chromatography ($CHCl_3 \rightarrow$ 50:1 $CHCl_3$/methanol) to obtain 153 mg of the desired compound 11 as a highly viscous oily substance (0.116 mmol, yield: 79%).

$^1$H NMR (600 MHz, $CDCl_3$): δ 8.18 (s, 1H), 8.07 (d, J=7.8 Hz, 1H), 7.98 (d, J=6.0 Hz, 1H), 7.82-7.78 (m, 3H), 7.71 (d, J=6.6 Hz, 2H), 7.55-7.53 (m, 2H), 7.46-7.34 (m, 10H), 7.22 (d, J=7.8 Hz, 2H), 6.84 (d, J=7.8 Hz, 2H), 6.80 (d, J=8.4 Hz, 2H), 4.06-4.02 (m, 4H), 3.79-3.75 (m, 4H), 3.66-3.57 (m, 36H), 3.49-3.45 (m, 4H), 3.31-3.27 (m, 6H), 2.83 (s, 4H); $^{13}C\{^1H\}$) NMR (150 MHz, $CDCl_3$): δ 169.13 (s, C), 168.50 (d, J=22.2 Hz, C), 161.66 (s, C), 158.15 (s, C), 158.10 (s, C), 141.80 (s. C), 138.40 (s, C), 137.93 (d, J=104.9 Hz, C), 137.68 (d, J=18.6 Hz, C), 136.88 (d, J=11.1 Hz, C), 133.49 (s, CH), 133.26 (s CH), 132.51 (d, J=106.1 Hz, C), 132.38 (s, CH), 132.30 (d, J=9.9 Hz, C), 131.90 (s, C), 130.56 (d, J=11.1 Hz, CH), 129.63 (d, J=101.1 Hz, C), 129.61 (s, CH), 129.56 (s, CH), 129.29 (s, CH), 129.14 (d, J=13.5 Hz, CH), 128.90 (s, CH), 128.60 (s, CH), 128.17 (s, CH), 126.80 (s, CH), 126.70 (s, CH), 125.47 (s, C), 125.00 (s, CH), 123.25 (s, CH), 122.12 (s, CH), 121.01 (d, J=8.7 Hz, CH), 114.75 (s, CH), 114.59 (s, CH), 71.74 (s, CH), 70.60 (s, CH), 70.42 (s, CH), 70.40 (s, CH), 70.32 (s, CH), 69.46 (s, CH), 67.25 (s, CH), 65.20 (d, J=11.1 Hz, C), 58.84 (s, CH), 25.51 (s, CH). One singlet signal of an aromatic quaternary carbon, two doublet signals of an aromatic quaternary carbon, one singlet signal of an aromatic CH carbon, and eighteen singlet signal of an alkyl CH carbon may be overlapped; $^{31}P\{^1H\}$ NMR (243 MHz, $CDCl_3$): δ 23.46.

Example 7: Synthesis of Compound 12

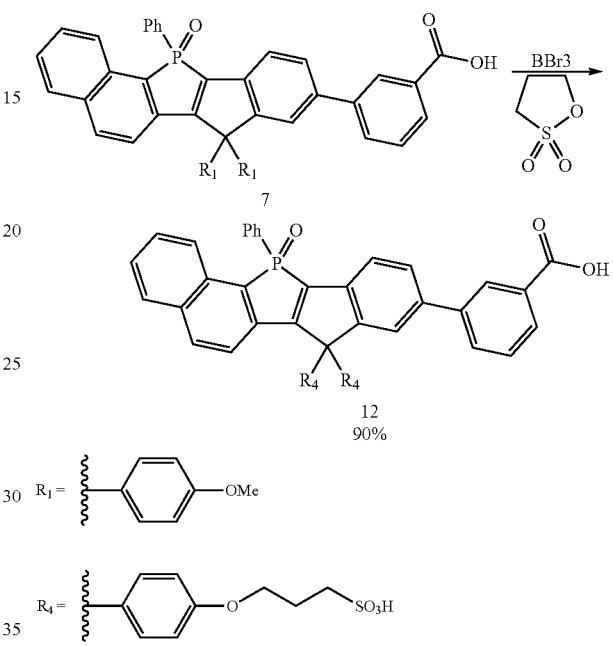

Boron tribromide ($BBr_3$; 0.55 mL, 5.7 mmol) was added dropwise to a solution of compound 7 obtained in Example 2 (200 mg, 0.287 mmol) in anhydrous $CH_2Cl_2$ (10 mL) at −78° C. The resulting mixture was slowly warmed to room temperature overnight. The reaction was quenched with $H_2O$ (5 mL) at 0° C., and the mixture was extracted with ethyl acetate (200 mL). The obtained organic layer was washed with saturated saline (30 mL) 3 times, then dried over anhydrous $Na_2SO_4$, and filtered. After the filtrate was concentrated under reduced pressure, the obtained solid was dissolved in dry dimethylformamide (DMF; 5 mL). Subsequently, $Cs_2CO_3$ (2.22 g, 6.81 mmol) and 1,3-propanesultone (0.500 mL, 5.69 mmol) were added to this solution, and the obtained mixture was stirred at room temperature for 2 hours. After all volatiles were distilled off under reduced pressure, the obtained solid was dissolved in water (10 mL). Subsequently, LiOH*$H_2O$ (1.00 g, 23.8 mmol) was added to this aqueous solution, and the obtained solution was stirred at room temperature for 2 hours. After the solution was acidified with concentrated hydrochloric acid, the mixture was purified by reverse-phase HPLC ($H_2O \rightarrow$ 1:1 $H_2O$/$CH_3CN$, +0.1% trifluoroacetic acid (TFA)) to obtain 235 mg of the desired compound 12 as an orange solid (0.257 mmol, yield: 90%).

Mp: >300° C. $^1$H NMR (400 MHz, DMSO-$d_6$): δ 8.11-8.06 (m, 2H), 7.98-7.77 (m, 7H), 7.65-7.28 (m, 12H), 7.15 (d, J=51.2 Hz, 1H), 6.97-8.95 (m, 4H), 4.05 (br, 4H), 2.74 (br, 4H), 2.05 (br, 4H). $^{13}C\{^1H\}$) NMR (100 MHz, DMSO-$d_6$): δ 168.4 (d, J=20.7 Hz, C), 167.4 (s, C), 158.6 (d, J=9.1 Hz, C), 158.2 (s, C), 140.3 (s, C), 138.9 (s, C), 137.7 (d,

J=103.1 Hz, C), 137.5 (d, J=18.2 Hz, C), 136.3 (d, J=11.6 Hz, C), 134.1 (s, CH), 133.2 (s, CH), 131.9 (s, C), 131.8 (s, C), 131.7 (s, C). 131.5 (s, CH), 130.4 (d, J=10.8 Hz, CH), 129.9 (d, J=12.4 Hz, CH), 129.7 (d, J=100.6 Hz, C), 129.70 (s, CH), 129.66 (s, CH), 129.56 (s, CH), 129.4 (s, CH), 128.9 (s, CH), 128.6 (s, CH), 127.6 (s, CH), 127.3 (s, CH), 127.1 (s, CH), 124.4 (s, CH), 123.3 (s, CH), 121.9 (s, CH), 121.3 (d, J=11.6 Hz, CH), 115.1 (s, CH), 115.0 (s, CH), 66.6 (s, CH), 65.2 (d, J=9.9 Hz, C), 48.2 (s, CH), 25.2 (s, CH). One singlet signal of a quaternary carbon, one of the doublet signals of a quaternary carbon paired with the signal at 133.23 ppm, one of the doublet signals of a quaternary carbon paired with the signal at 132.90 ppm, one of the doublet signals of a quaternary carbon paired with the signal at 131.73 ppm, and three singlet signals of alkyl carbons may be overlapped. $^{31}P\{^{1}H\}$ NMR (162 MHz, DMSO-$d_6$): δ 21.8. HRMS (APCI): m/z calcd. for $C_{50}H_{41}NaO_{11}PS_2$: 935.1720 ([M+Na]$^+$); found. 935.1737.

Example 8: Synthesis of Compound 13 (Phox-COOH PB430)

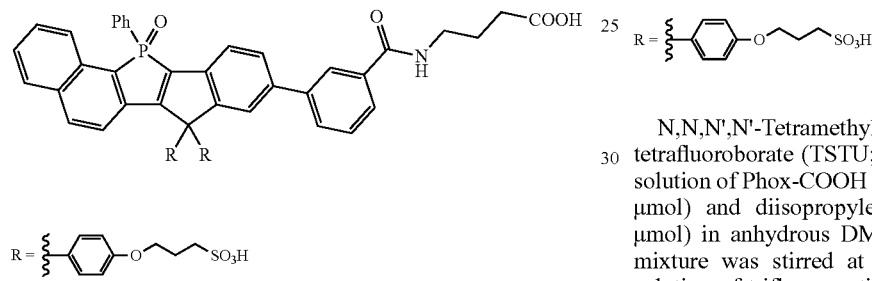

N,N,N',N'-tetramethyl-O—(N-succinimidyl)uronium tetrafluoroborate (TSTU; 9.2 mg, 0.031 enol) was added to a solution of compound 12 obtained in Example 7 (14.0 mg, 0.0153 mmol) and diisopropylethylamine (DIPEA; 0.10 mL, 0.61 mmol) in anhydrous DMSO (1 mL). After stirring at room temperature for 1 hour, 4-aminobutyric acid (10.3 mg, 0.100 mmol) was added to the reaction mixture. After this mixture was stirred at room temperature for 12 hours, the mixture was purified by reverse-phase HPLC (6:4 H$_2$O/CH$_3$CN, +0.1% TFA) to obtain 9.3 mg of the desired compound 13 (Phox-COOH) as a yellow solid (0.0093 mmol, yield: 61%).

Mp: 197.0-199.5° C. $^1$H NMR (400 MHz, DMSO-$d_6$): δ 8.60 (t, J=6.0 Hz, 1H), 8.08 (d, J=8.4 Hz, 1H), 7.97-7.95 (m, 3H), 7.84 (s, 1H), 7.79-7.48 (m, 12H), 7.42 (dd, J=8.4 Hz, 2.8 Hz, 1H), 7.37 (d, J=8.8 Hz, 2H), 7.25 (d, J=8.8 Hz, 2H), 6.95-6.90 (m, 4H), 4.03-3.98 (m, 4H), 3.31-3.26 (m, 2H), 2.60-2.54 (m, 4H), 2.29 (t, J=7.2 Hz, 2H), 2.00-1.94 (m, 4H), 1.79-1.74 (m, 2H). Satisfying $^{13}C\{^{1}H\}$NMR was not obtained duo to the small amount of product and the splitting of carbon signal. $^{31}P\{^{1}H\}$ NMR (162 MHz, DMSO-$d_6$): δ 21.5. HRMS (APCI): m/z calcd. for $CH_9NO_{12}PS_2$: 998.2428 ([M+H]$^+$); found. 998.2427.

Example 9: Synthesis of Compound 14 (Phox-NHS Ester)

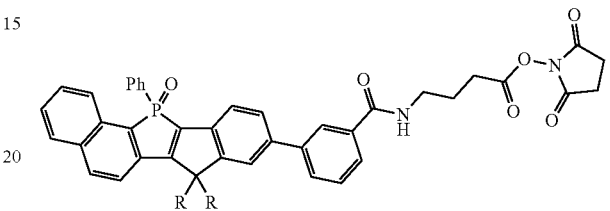

N,N,N',N'-Tetramethyl-O—(N-succinimidyl)uronium tetrafluoroborate (TSTU; 4.5 mg, 15 μmol) was added to a solution of Phox-COOH obtained in Example 8 (5.0 mg, 5.0 μmol) and diisopropylethylamine (DIPEA; 17 μL, 100 μmol) in anhydrous DMSO (0.5 mL). After the resulting mixture was stirred at room temperature for 1 hour, a solution of trifluoroacetic acid (TFA; 17 μL, 220 μmol) in water (2 mL) was added to quench the reaction. The resulting mixture was purified by reverse-phase HPLC (55:45 H$_2$O/CH$_3$CN, +0.1% TFA) to obtain 4.3 mg of the desired compound 14 as a yellow solid (3.9 μmol, yield: 79%).

Mp: 195.5-197.5° C. $^1$H NMR (400 MHz, DMSO-$d_6$): δ 8.65 (s, 1H), 8.08 (d, J=8.8 Hz, 1H), 7.98-7.95 (m, 3H), 7.84-7.35 (m, 16H), 7.25 (d, J=8.0 Hz, 2H), 6.94-6.89 (m, 4H), 4.03-3.98 (m, 4H), 3.36-3.31 (m, 2H), 2.82 (s, 4H), 2.78 (t, J=7.6 Hz, 2H), 1.98-1.87 (m, 6H). One set of alkyl multiple signals was overlapped in DMSO residual peak. $^{31}P\{^{1}H\}$ NMR (162 MHz, DMSO-d): δ 25.0. HRMS (APCI): m/z calcd. for $C_{58}H_{52}N_2O_{14}PS_2$: 1095.2592 ([M+H]$^+$); found. 1095.2600.

Example 10: Synthesis of Compound 14 (Phox-maleimide)

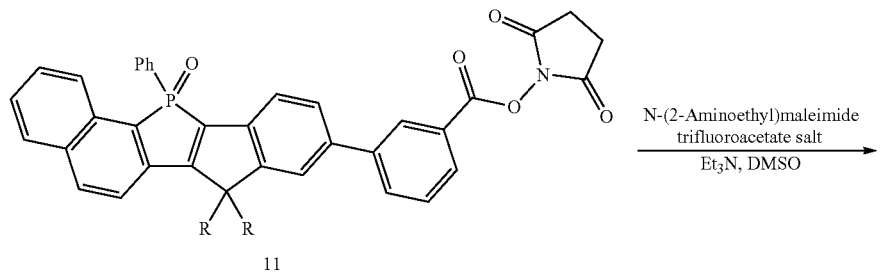

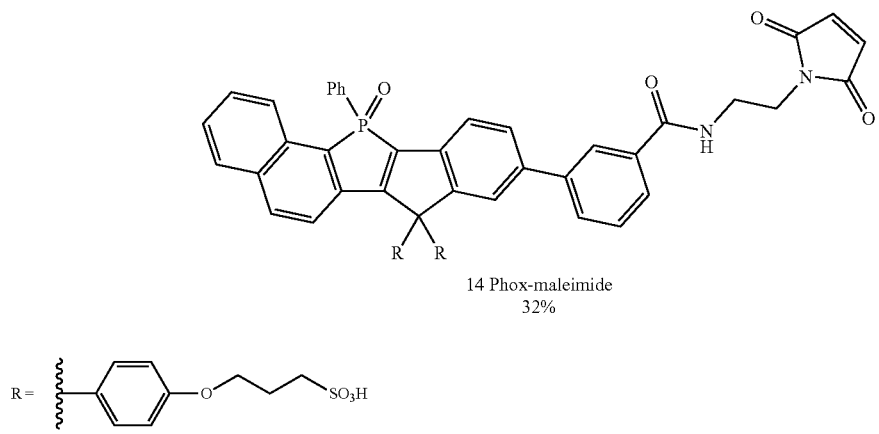

14 Phox-maleimide
32%

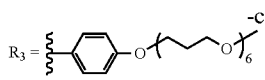

Triethylamine (Et3N; 28 μL, 200 μmol) was added to a solution of Compound 11 obtained in Example 6 (10.0 mg, 9.9 μmol) and N-(2-aminoethyl)maleimide trifluoroacetate (2.5 mg, 9.8 μmol) in anhydrous dimethyl sulfoxide (DMSO; 1 mL). After the resulting mixture was stirred at room temperature for 2 hours, the mixture was purified by reverse-phase HPLC (55:45 H$_2$O/CH$_3$CN, +0.1% trifluoroacetic acid (TFA)) to obtain 3.2 mg of the desired compound 12 (Phox-maleimide) as a yellow solid (3.1 mmol, yield: 32%).

$^1$H NMR (600 MHz, DMSO-d$_6$): δ 8.66 (t, J=6.0 Hz, 1H), 8.08 (d, J=8.4 Hz, 1H), 7.96 (d, J=8.4 Hz, 2H), 7.90-7.35 (m, 16H), 7.26 (d, J=8.4 Hz, 2H), 7.15 (d, J=51.0 Hz, 1H), 7.05 (d, J=31.8 Hz, 1H), 6.94-6.91 (m, 5H), 4.04-3.98 (m, 4H), 3.60-3.55 (m, 2H), 3.43-3.39 (m, 2H), 2.58-3.54 (m, 4H), 1.98-1.94 (m, 4H). $^{31}$P{$^1$H} NMR (162 MHz, DMSO-d$_6$): δ 25.1. MS (MALDI-TOF): m/z calcd. for C$_{56}$H$_{47}$N$_2$NaO$_{12}$PS$_2$: 1057.2 ([M+Na]+); found. 1057.0.

Comparative Example 1: Alexa Fluor 430

A commercially available fluorescent dye, Alexa Fluor 430, was used as the fluorescent dye of Comparative Example 1.

Comparative Example 2: Atto 425

A commercially available fluorescent dye, Atto 425, was used as the fluorescent dye of Comparative Example 2.

Comparative Example 3: C-Naphox

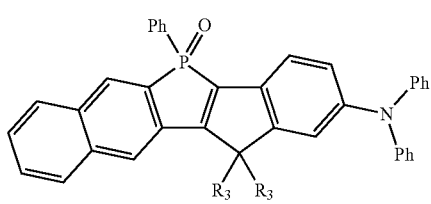

-continued

The above compound was synthesized in the same manner as compound 7b disclosed in WO2015/111647.

Comparative Example 4: Alexa Fluor 488

Alexa Fluor 488, commercially available, was used as the fluorescent dye of Comparative Example 4.

Test Example 1: Molecular Orbital Calculation

To examine the difference in UV-visible absorption and fluorescence spectra between Phox 430 NHS Ester obtained in Example 6 and C-Naphox obtained in Comparative Example 3, TD-DFT calculation and structural optimization by molecular orbital calculation were performed. FIG. 1 shows the results.

The results show that as found that the HOMO and LUMO energy levels can be reduced by adjusting the positions at which benzene rings are fused as in Phos 430 NHS Ester of Example 6. The results thus suggest that since the phosphole compound represented by formula (1B), among the phosphole compounds of the present invention, can particularly decrease the HOMO and LUMO energy levels, this phosphole compound can more increase the fluorescence peak wavelength, as well as the fluorescence quantum yield.

Test Example 2: Photophysical Properties

Figure 2:
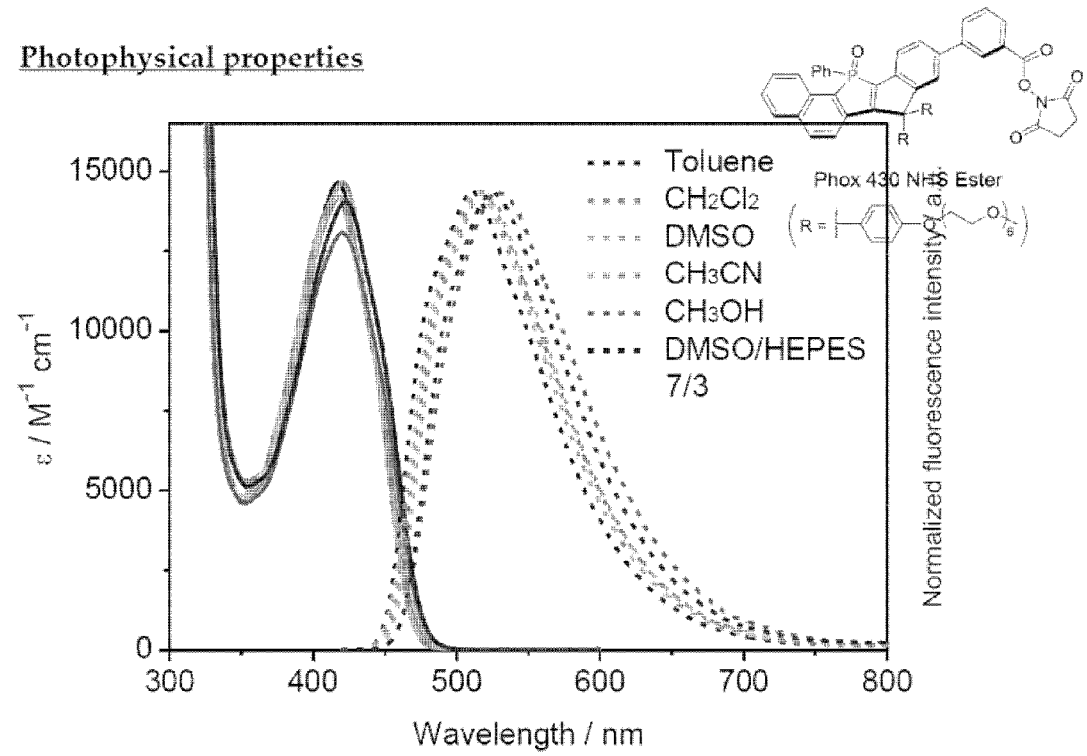
FIG. 2 shows UV-visible absorption and fluorescence spectra of Phox 430 NHS Ester in various solvents.

Phox 430 NHS Ester obtained in Example 6 was dissolved in various solvents at a concentration of about 10$^{-5}$ M. UV-visible absorption and fluorescence spectra, absolute fluorescence quantum yield, fluorescence lifetime, etc. of these solutions were measured. Alexa Fluor 430 obtained in Comparative Example 1 and Atto 425 obtained in Comparative Example 2 were also dissolved in HEPES at a concentration of about 10$^{-5}$ M. UV-visible absorption and fluorescence spectra, absolute fluorescence quantum yield, fluorescence lifetime, etc. of these solutions were also measured. Table 1 and FIG. 2 show the results.

TABLE 1

| Dye | Solvent | Absorption | | Fluorescence | | | | |
|---|---|---|---|---|---|---|---|---|
| | | $\lambda_{abs}$ (nm) | $\varepsilon$ ($10^4$ M$^{-1}$cm$^{-1}$) | $\lambda_{em}$ (nm) | $\varphi_F$ | $\tau$ (ns) | $k_r$ ($10^8$ s$^{-1}$) | $K_{nr}$ ($10^8$ s$^{-1}$) |
| Phox 430 | Toluene | 417 | 1.47 | 512 | 0.84 | 6.3 | 1.3 | 0.25 |
| | CH$_2$Cl$_2$ | 418 | 1.42 | 517 | 0.87 | 7.7 | 1.1 | 0.17 |
| | DMSO | 421 | 1.47 | 520 | 0.89 | 7.7 | 1.2 | 0.14 |
| | CH$_3$CN | 416 | 1.42 | 514 | 0.84 | 7.6 | 1.1 | 0.21 |
| | CH$_3$OH | 420 | 1.31 | 527 | 0.86 | 9.7 | 0.89 | 0.14 |
| | DMSO/HEPES 7/3 | 423 | 1.41 | 525 | 0.90 | 9.0 | 1.0 | 0.11 |
| Alexa 430 | HEPES | 430 | 1.50 | 545 | | | | |
| Atto 425 | | 436 | 4.5 | 484 | 0.90 | 3.6 | 2.5 | 0.28 |

The above results show that the phoshole compound of the present invention in any of various solvents can fluoresce under light in the visible light region (in particular, at about 400 to 500 nm; the absorption spectral behavior and the fluorescence spectral behavior are almost the same). It can also be understood that the phosphole compound exhibits high brightness even in aqueous solvents. The phosphole compound of the present invention further has a feature that it has a large Stokes shift (5020 cm$^{-1}$). Further, the phosphole compound of the present invention has a feature that it has a maximum absolute fluorescence quantum yield of 0.90, which indicates brightness comparable to that of conventional fluorescent dyes, and also has a fluorescence lifetime of 6 ns or more, which is much longer than a conventional lifetime of about 1 to 4 ns.

Next, photophysical properties of the phosphole compound of the present invention and conventional fluorescent dyes in PBS buffer (pH=7.4) were measured in the same manner. Table 2 shows the results.

TABLE 2

| Dye | PB430 | PB430-antibody | Alexa 430 | Alexa 488 | Atto 425 |
|---|---|---|---|---|---|
| $\lambda_{abs}$ (nm) | 426 | 427 | 431 | 495 | 436 |
| $\lambda_{em}$ (nm) | 542 | 539 | 541 | 519 | 484 |
| Stokes shift (cm$^{-1}$) | 5020 | 4870 | 4720 | 935 | 2270 |
| $\varepsilon$ ($10^4$M$^{-1}$CM$^{-1}$) | 10400 | — | 16000 | 73000 | 45000 |
| $\varphi_F$ | 0.66 | 0.67 | 0.55 | 0.92 | 0.65 |
| Brightness ($\varepsilon \cdot \varphi_F$) (M$^{-1}$cm$^{-1}$) | 6900 | — | 8800 | 67000 | 29000 |
| $\tau$ (ns) | 10.6 | 10.1 | 3.3 | 4.1 | 4.0 |
| Relative photostability[a] | 37 | — | 1 | 2.3 | 5.3 |

Notes:
The relative photostability[a] is defined as a fluorescence signal retention rate under irradiation with a 470-nm confocal laser. Relative evaluation was performed based on the value of Alexa Fluor 430 defined as 1.

Test Example 3: Fluorescence Quantum Yield in DISO/HEPES Buffer

Figure 3:
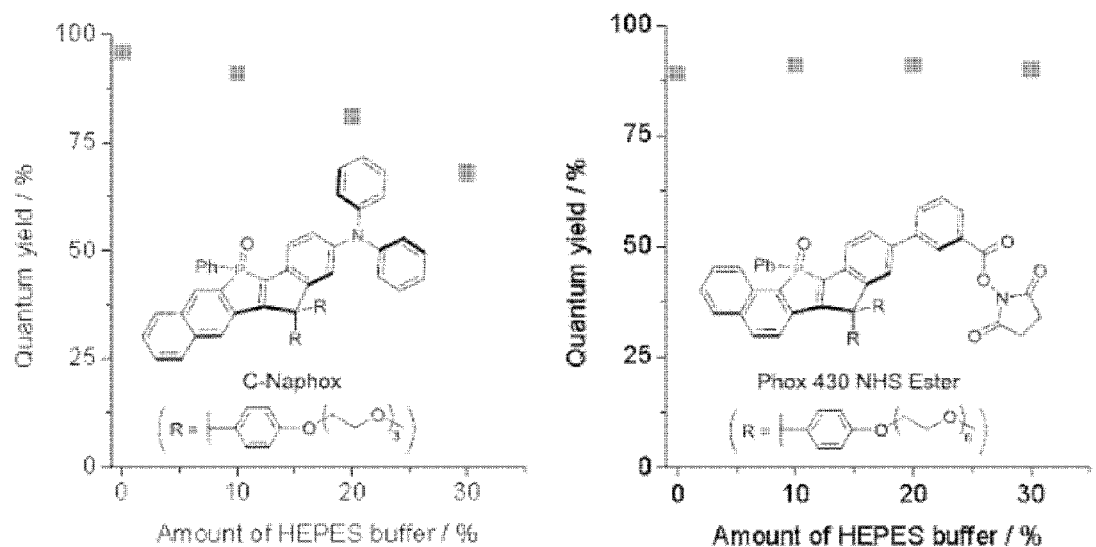
FIG. 3 is graphs showing fluorescence quantum yields of Phox 430 NHS Ester of Example 6 and C-Naphox of Comparative Example 3 in mixed solvents of DMSO and HEPES that are mixed at various ratios.

Phox 430 NHS Ester obtained in Example 6 and C-Naphox obtained in Comparative Example 3 were dissolved at a concentration of about 10$^{-6}$M in mixed solvents of DMSO and HEPES. Absolute fluorescence quantum yields of these solutions were measured. The measurement was performed in the mixed solvents containing HEPES at various ratios, and fluorescence quantum yield variation relative to water content was evaluated. FIG. 3 show the results. The fluorescence quantum yield is plotted on the ordinate of FIG. 3; 100% shows the theoretical upper limit of fluorescence quantum yield. The results clearly show that as compared with C-Naphox of Comparative Example 3, whose fluorescence quantum yield decreased with an increase of water content, the phosphole compound of the present invention can maintain a high fluorescence quantum yield even in solvents containing water.

Test Example 4: Light Resistance

Figure 4:
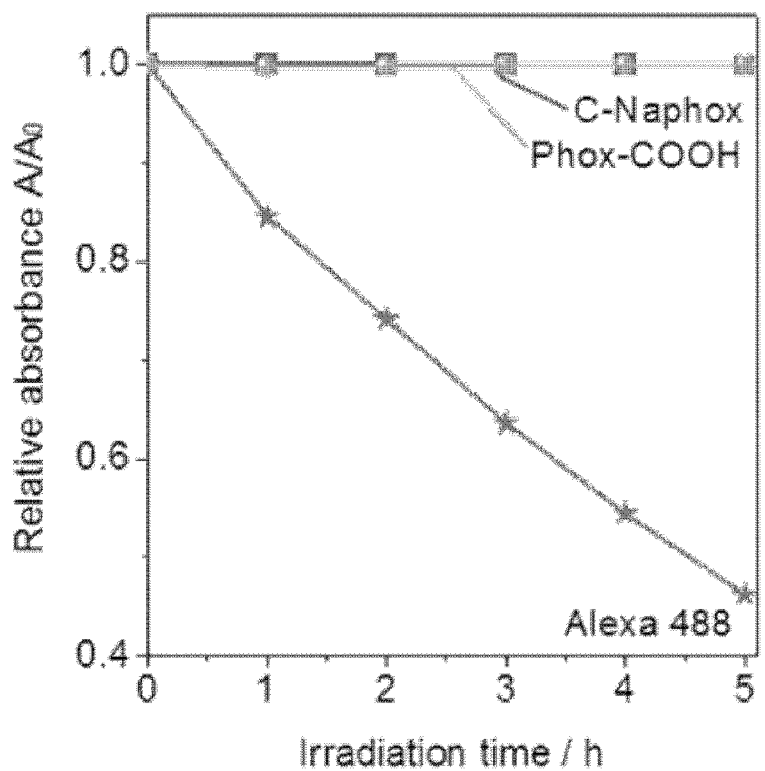
FIG. 4 is a graph showing the fluorescence quantum yield retention rate of Phox-COOH of Example 8, C-Naphox of Comparative Example 3, and C-Bphox of Comparative Example 4 in a DMSO/HEPES buffer (pH=7.3, v/v=7/3) mixed solvent after various times from laser irradiation.
Figure 5:
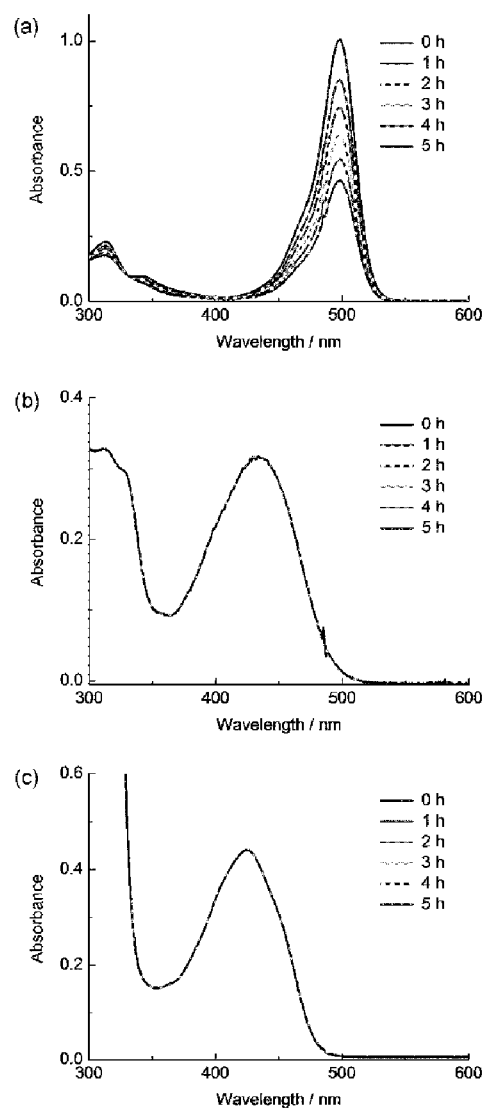
FIG. 5 shows absorption spectra of various fluorescent dyes (a: Alexa Fluor 488, b: C-Naphox, c: PB430) in a DMSO/HEPES buffer mixed solvent (pH=7.3, v/v=7/3) after various times from laser irradiation. The solution concentrations were adjusted to the optical density (Alexa Fluor 488: 0.22, C-Naphox: 0.22, PB430: 0.21) at an excitation wavelength of 460 nm.

Phox-COOH of Example 8, C-Naphox of Comparative Example 3, and Alexa Fluor 488 of Comparative Example 4 were dissolved in a DMSO/HEPES buffer (pH=7.3, v/v=7/3) mixed solvent. The concentrations of these compounds were adjusted to be comparable to each other in terms of absorbance at 460 nm. Each solution was irradiated with light using a xenon lamp (300 W) equipped with a band-pass filter that transmits light of 460 nm±11 nm, and UV-visible absorption spectra were measured after various times. The absorbance ($A_0$) of each sample immediately after irradiation (after 0 seconds) was defined as 1.00. The absorbance (A) retention rate (A/A$_0$) after elapse of a predetermined time was evaluated. FIGS. 4 and 5 show the results. The results show that photoirradiation of Phox-COOH and C-Naphox for 5 hours caused almost no reduction in fluorescence intensity (99% of the dyes remained intact), whereas only 46.2% of the fluorescence intensity of Alexa Fluor 488 persisted under the photoirradiation for 5 hours, and the photoirradiation reduces the fluorescence intensity of Alexa Fluor 488. It can be understood that the phosphole compound of the present invention has high light resistance comparable to that of C-Naphox, and that its properties are far superior to those of Alexa Fluor 488.

Test Example 5: Evaluation of pH Dependency of Fluorescence

Figure 6:
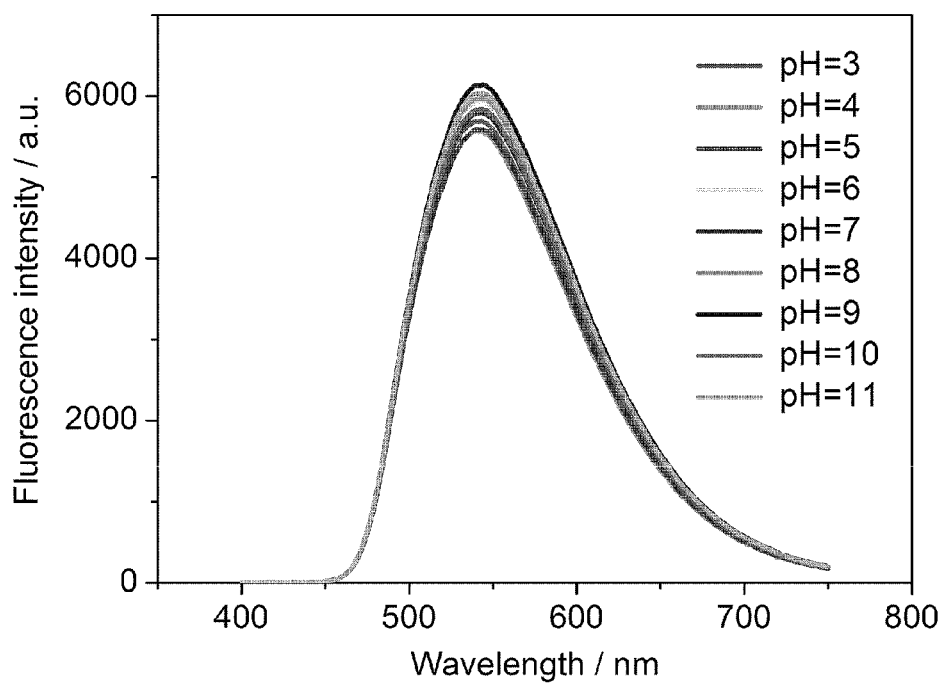
FIG. 6 is a graph showing pH-dependence of fluorescence of Phox-COOH (10 µM) obtained in Example 8.

The fluorescence spectra of Phox-COOH (10 μM) obtained in Example 8 were measured in aqueous solutions of various pH values. For adjustment in the range of pH 3 to pH 6, citric acid/Na$_2$HPO$_4$ buffer was used. For adjustment in the range of pH 7 to pH 8, Na$_2$HPO$_4$/NaH$_2$PO$_4$ buffer was used. For adjustment in the range of pH 9 to pH 11, Na$_2$CO$_3$/NaHCO$_3$ buffer was used. The method for measuring the fluorescence spectra was otherwise the same as in Test Example 2. FIG. 6 shows the results. The results show that fluorescence wavelength did not change with pH and that fluorescence intensity was also substantially maintained with minor changes according to the pH (the highest fluorescence intensity being at a pH of 9).

Test Example 6: Conjugate of Phosphole Compound to Antibody

Figure 7:
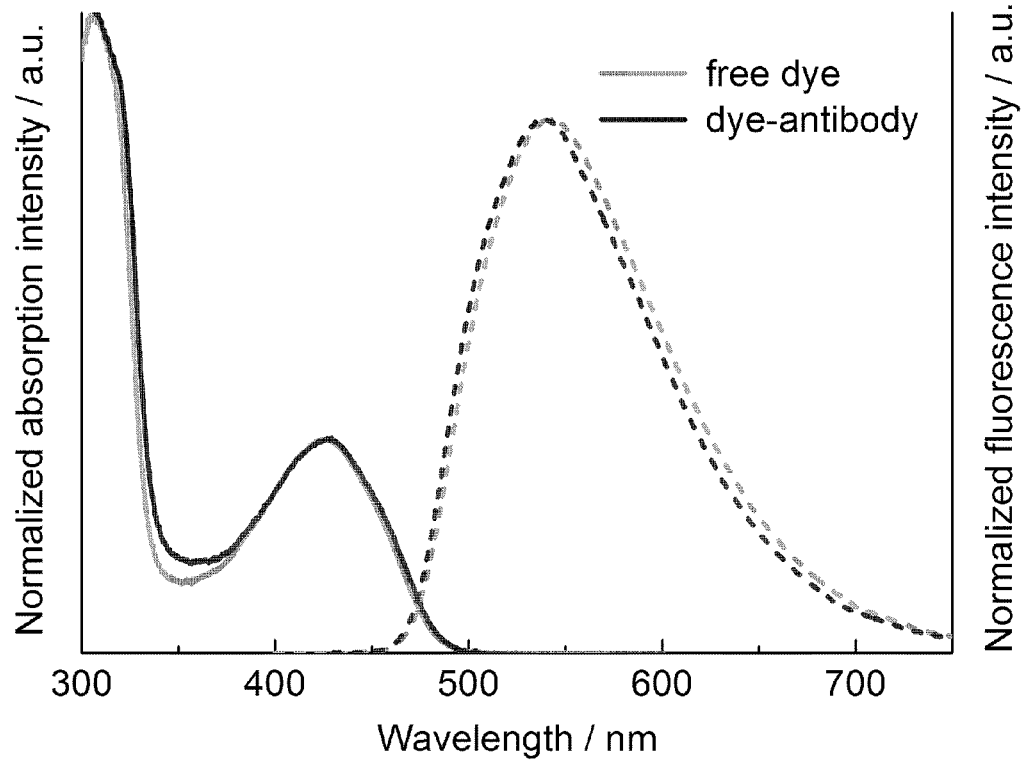
FIG. 7 shows UV-visible absorption (solid line) and fluorescence (dashed line) spectra of Phox-COOH-conjugated antibody and Phox-conjugated antibody in PBS buffer solution (pH=7.4).

In order to conduct STED imaging, Phox-NHS Ester obtained in Example 9 was conjugated to a goat anti-mouse IgG antibody to form a Phox-antibody conjugate. The degree of labeling (DOL) of the sample prepared from 20 μg of Phox-NHS Ester and 0.50 mg of IgG antibody in 0.25 mL of a labeling buffer (pH of 8.3) was determined to be 2.8. As shown in FIG. 7, the photophysical properties of Phox-antibody conjugate were almost identical to those of antibody-free Phox-COOH in PBS (pH 7.4), which indicates that there was almost no interaction between the fluorophores or with the amino acid residues of the antibody.

The labeling buffer at a pH of 8.3 was prepared by mixing PBS buffer (pH of 7.4) with 0.2M $NaHCO_3$ at a ratio of 20:1 (v/v). A DMSO (10 μL) solution of Phox-NHS Ester (Example 9; 0.020 mg) was added to a labeling buffer (pH of 8.3, 0.25 mL) of goat anti-mouse antibody IgG (0.50 mg), and the resulting mixture was cultured at room temperature for 1 hour. After free Phox-NHS Ester was removed by Sephadex G-25 column chromatography, the degree of labeling (DOL) (the number of fluorophores bound per antibody) was measured. The DOL was calculated in accordance with the calculation method described in the "Determination of Degree of Labeling (DOL)" section in the manual of ThermoFisher Scientific's Alexa Fluor (registered trademark) 488 Microscale Protein labeling Kit (https://tools.thermofisher.com/content/sfs/manuals/mp30006.pdf), except that $A_{280}$ and $A_{426}$ were used in place of $A_{280}$ and $A_{494}$ for calculation.

The DOL calculation method is as follows.

First, the correction coefficient $CF_{280}$ of Phox-COOH was calculated according to the following formula. In the formula, $\varepsilon_{280}$ and $\varepsilon_{max}$ represent absorption coefficients of a fluorescent dye at 280 nm and at the absorption maximum (426 nm).

$$CF_{280} = \frac{\varepsilon_{280}}{\varepsilon_{max}} = \frac{19900 \ M^{-1} \ cm^{-1}}{10400 \ M^{-1} \ cm^{-1}} = 1.91$$

Next, the degree of labeling (DOL, dye:protein ratio) of the Phox-antibody conjugate was calculated according to the following formula. In the formula, $A_{max}$ and $A_{280}$ represent absorbance of the Phox-antibody conjugate at the absorption maximum of each dye (426 nm) and 280 nm. The difference between $A_{280}$ and $A_{max} \times CF_{280}$ refers to the absorbance of the antibody itself ($A_{protein}$). $\varepsilon_{protein}$ represents the absorption coefficient of the antibody at 280 nm.

$$DOL = \frac{A_{max}/\varepsilon_{max}}{A_{protein}/\varepsilon_{protein}} = \frac{A_{max}/\varepsilon_{max}}{(A_{280} - A_{max} \times CF_{280})/\varepsilon_{protein}}$$
$$= \frac{0.0362/(10400 \ M^{-1} \ cm^{-1})}{(0.333 - 0.0362 \times 1.91)/(210000 \ M^{-1} \ cm^{-1})} = 2.8$$

Binding of the Phox-NHS Ester to the antibody was performed 3 times under the same conditions. Table 3 shows the results. All the obtained DOL values were equivalent.

TABLE 3

| Entry | $A_{280}$ | $A_{max}$ | DOL |
|---|---|---|---|
| 1 | 0.333 | 0.0362 | 2.77 |
| 2 | 0.803 | 0.0793 | 2.46 |
| 3 | 0.815 | 0.0827 | 2.54 |

Test Example 7: Preparation of Cells

HeLa cells (RIKEN Cell Bank, Japan) were cultured in Dulbecco's modified Eagle's medium (DMEM, Sigma) containing 10% fetal bovine serum (FBS, Gibco) and 1% antibiotic-antimycotic (AA, Sigma) at 37° C. in a 5% $CO_2$/95% air incubator. Three days before imaging, the cells ($5\times10^4$) were seeded on a glass-bottom 8-well plate. Immunofluorescently labeled tubulin and vimentin of fixed HeLa cells were prepared in the following manner. 1) HeLa cells were fixed with 4% formaldehyde and cultured at room temperature for 20 minutes. After washing with PBS buffer (pH of 7.4) once, the resulting cells were treated with 0.5% Triton-X100 for 10 minutes and washed again with PBS buffer (pH of 7.4) 3 times. 2) The cells were blocked with 1% bovine serum albumin (BSA) at room temperature for 30 minutes and washed with PBS buffer (pH of 7.4) 3 times. 3) The cells were incubated with 0.5 μg/mL anti-α-tubulin mouse monoclonal antibody (017-25031, Wako) and/or 0.5 μg/mL anti-vimentin rabbit monoclonal antibody (ab92547, abcam) at room temperature for 1 hour and then washed with PBS buffer (pH of 7.4) 3 times. 4) The obtained samples were further incubated with the corresponding fluorescent dye-labeled secondary antibodies as follows: 10 μg/mL Phox-NHS Ester (Example 9)-conjugated anti-mouse IgG (DOL=2.5), 10 μ/mL Alexa Fluor 430 (Comparative Example 1)-conjugated anti-rabbit IgG (A-11064, Invitrogen), 10 μg/mL Alexa Fluor 430 (Comparative Example 1)-conjugated anti-mouse IgG (DOL=1.9), 10 μg/mL Atto 425 (Comparative Example 2)-conjugated anti-mouse IgG (DOL=1.7), and 4 μg/mL Alexa Fluor 488 (Comparative Example 4)-conjugated anti-mouse IgG (ab150113, abcam) at room temperature for 4 hours and then washed with PBS buffer (pH of 7.4) 3 times. Finally, the resulting cells were mounted in PBS and glycerol (volume ratio: 1:1).

Test Example 8: Fluorescent Imaging No. 1

Confocal imaging and STED imaging were performed using the immunofluorescence-labeled vimentin prepared in Test Example 7.

A super-resolution TCS SP8 STED microscope equipped with an HCXPL APO 100×/1.40 oil immersion lens was used for confocal imaging and STED imaging. In confocal imaging, cells were irradiated with a 470-nm laser (wavelength-tunable white excitation laser, 80 MHz, output power: 30%, AOTF: 90%), and fluorescent signals within the range of 480 to 585 nm were detected. For repeated STED imaging and Z-scan STED imaging, a wavelength-tunable white excitation laser (470 nm, 80 MHz, output power: 40%, AOTF: 90%) and a CW-STED laser (592 nm, CW laser, output power: 20%, AOTF: 80%) were used with the emission detection window being set at 480 to 585 nm, and the time gating method (time range: 0.5 to 12 ns) was used. For two-color STED imaging, a wavelength-tunable white excitation laser (470 nm, 80 MHz, output power: 80%, AOTF: 90%) and a CW-STED laser (a 592-nm CW laser, output power: 20%, AOTF: 80%) were used with the luminescence detection window being set at 480 to 585 nm, and the time gating method (time range: 0.5 to 12 ns) was used. Z-scan STED images were subjected to Huygens deconvolution to construct a 3D structure of tubulin. For two-color STED image analysis, Huygens deconvolution was performed. These images were analyzed with the ImageJ software (http://imagej.nih.gov/ij/).

Figure 8:
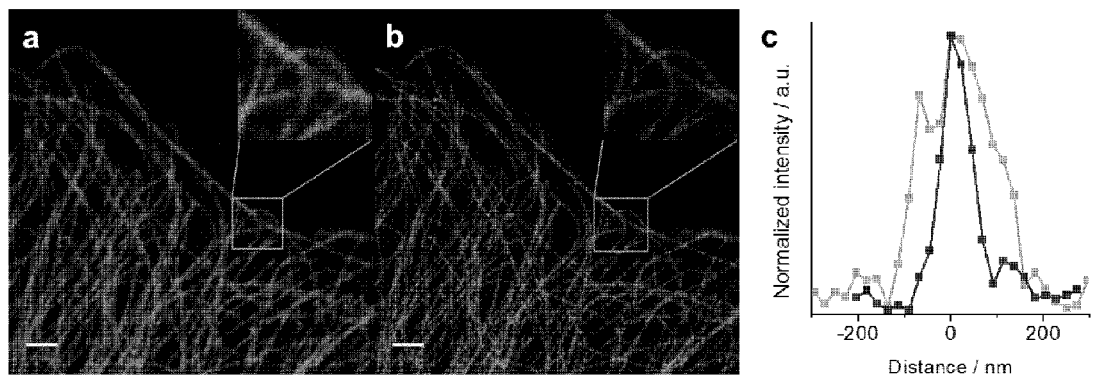
FIG. 8 shows the results of confocal imaging and STED imaging of immunofluorescently labeled vimentin.

FIG. 8 shows the results of confocal imaging and STED imaging of vimentin immunofluorescently labeled with Phox-NHS Ester (Example 9). FIG. 8 shows a confocal microscopy image (a) and a STED microscopy image (b) of tubulin filaments immunolabeled with Phox-NHS Ester (Example 9) in a fixed HeLa cell, and the corresponding optical resolutions (c) of the confocal (orange line) and STED (crimson line) microscopy images. FIG. 8(a) and FIG. 8(b) include inserts of enlarged images of the selected portions. A wavelength-tunable white excitation laser (470 nm, 80 MHz, output power: 40%, AOTF: 90%) and a CW-STED laser (592-nm CW laser, output power: 20%, AOTF: 80%) were used. Scale bars in FIG. 8 (a) and FIG. 8 (b) indicate 2 μm. This result clearly shows that the phosphole compound of the present invention can be used to label a protein (in particular, an antibody) and fluoresce; STED imaging using this phosphole compound can achieve a spatial resolution of more than 200 nm.

Figure 9:
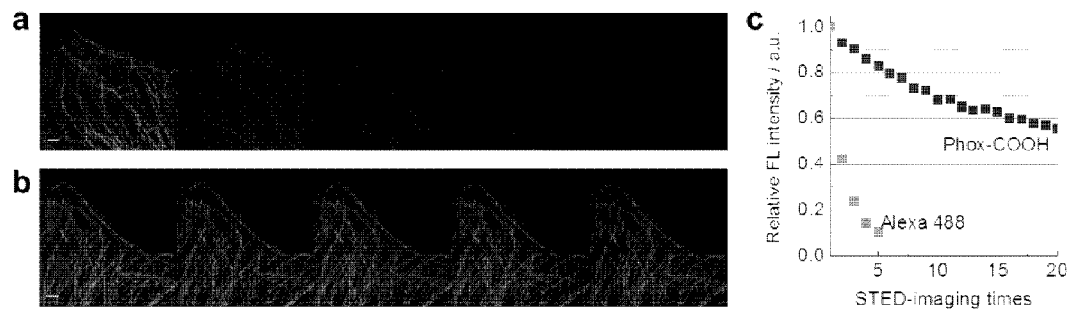
FIG. 9 shows the photostability of Alexa Fluor 488 (Comparative Example 4) and Phox-NHS Ester (Example 9) under STED conditions.

Next, FIG. 9 shows a comparison of photostability between Alexa Fluor 488 (Comparative Example 4) and Phox-NHS Ester (Example 9) under STED conditions. In this test, STED microscopy images of tubulin filaments immunolabeled with Alexa Fluor 488 (Comparative Example 4; a) and Phox-NHS Ester (Example 9; b) were repeatedly captured 5 times consecutively. Next, changes in fluorescence intensity versus the number of repetition of STED imaging were plotted in FIG. 9(c). FIG. 9(c) shows to what degrees the fluorescence intensity can be maintained from the initial value. Imaging of tublin filaments labeled with Alexa Fluor 488 (Comparative Example 4) and that with Phox-NHS Ester (Example 9) were both performed under the same conditions. A wavelength-tunable white excitation laser (470 nm, 80 MHz, output power: 40%, AOTF: 90%) and a CW-STED laser (592-nm CW laser, output power: 20%, AOTF: 80%) were used. Scale bars in FIG. 9(a) and FIG. 9 (b) indicate 2 μm. This result clearly shows that even in repeated STED imaging, the phosphole compound of the present invention can maintain fluorescence intensity and has excellent photostability.

Figure 10:
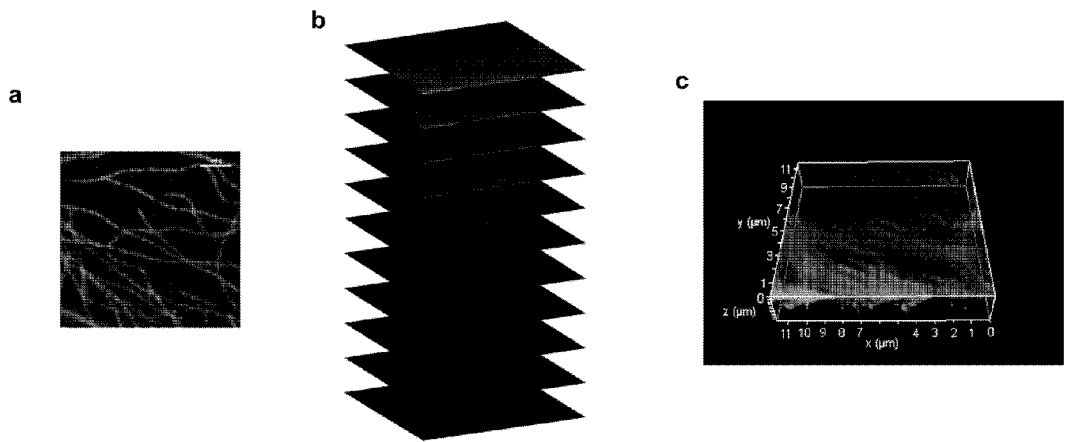
FIG. 10(*a*) is a confocal fluorescence microscopy image of tubulin immunolabeled with Phox-NHS Ester (Example 9).
Figure 11:
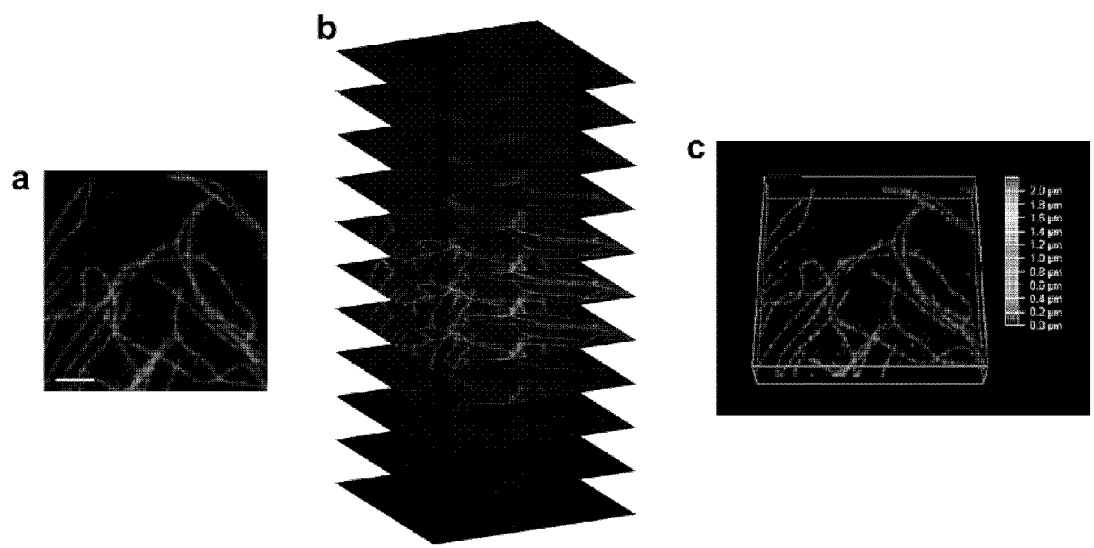
FIG. 11(*a*) is a confocal fluorescence microscopy image of tubulin immunolabeled with Alexa Fluor 488 (Comparative Example 4).

Next, FIG. 10 and FIG. 11 (FIG. 10: Example 9, FIG. 11: Comparative Example 4) show a comparison between Alexa Fluor 488 (Comparative Example 4) and Phox-NHS Ester (Example 9) in photostability during Z-scan STED imaging.

In this test, STED imaging of tubulin filaments immunolabeled with Alexa Fluor 488 (Comparative Example 4) and those immunolabeled with Phox-NHS Ester (Example 9) was consecutively performed in the depth (z-axis) direction.

FIG. 10(a) and FIG. 11(a) show confocal fluorescence microscopy images with Alexa Fluor 488 (Comparative Example 4) and those with Phox-NHS Ester (Example 9). FIG. 10(b) and FIG. 11(b) show Z-scan STED microscopy images in a depth of 2 μm. The Z-scanning step was set to intervals of 200 nm, and 11 slides were recorded. After analysis of the 11 slides and image reconstruction, the three-dimensional structure of tubulin filaments was obtained with a dimension of 11.62×11.62×2.00 μm³, as shown in FIG. 10(c) and FIG. 11(c). For STED imaging, a wavelength-tunable white excitation laser (470 nm, 80 MHz, output power: 40%, AOTF: 90%) and a CW-STED laser (592-nm CW laser) output power: 20%, AOTF: 80%) were used. Tubulin filaments immunolabeled with Phox-NHS Ester (Example 9) and those with Alexa Fluor 488 (Comparative Example 4) were both imaged under the same conditions. Scale bars in FIG. 10 (a) and FIG. 11 (a) indicate 2 μm. The results show that Alexa Fluor 488 (Comparative Example 4) faded during repeated scanning in the Z direction and that almost no fluorescence was observed in the 6th slide, in which a fluorescent image should have been confirmed most clearly. In contrast, the phosphole compound of the present invention did not fade during the Z-scanning process; and an appropriate structure was observed even after images were reconstructed into a three-dimensional structure, which clearly indicates that the phosphole compound of the present invention has excellent photostability. This suggests that the phosphole compound of the present invention is applicable to Z-scan STED imaging that requires long-term light irradiation, such as Z-scan STED imaging and 3D STED imaging.

Test Example 9: Fluorescent Imaging No. 2

Imaging experiments were performed using a Leica TCS SP8 STED 3X system (Leica Microsystems), including an inverted DMI6000 CS microscope equipped with a tunable (470 to 670 nm) pulsed white-light laser (WLL; pulse repetition rate of 78 MHz) for excitation and a STED laser (continuous wave at 592 nm) for depletion. For confocal imaging and STED imaging, a HyD detector and a 100× oil immersion objective lens (NA: 1.4) were used. The dyes were excited with the WLL at 470 nm, and fluorescent signals were collected between 480 nm and 585 nm with a time gating interval of 0.5 to 12 ns. Z-stack images were obtained with increments of 50 nm. For two-color imaging, the images were first deconvoluted using the Huygens Deconvolution software (Scientific Volume Imaging), and the deconverted images were further processed with the ImageJ image analysis software (http://imagej.nih.gov/ij/). For the evaluation of photostability under confocal conditions, dye-stained cells prepared as described above were irradiated with the WLL at 470 nm (12 μW) and images were acquired at the following setting: 1024×1024 pixels; line average: 3; frame average: 1; and irradiation time: 5 seconds/image. The total signal strength of each image was normalized to the value of the first image and plotted as a function of the number of recorded confocal images. The decay curve was analyzed as a pseudo first-order reaction (Dyes Pigm. 1998, 37, 213-222), and the photobleaching rate constant was calculated from the slope of the straight line. Relative photostability to Alexa Fluor 430 was determined by using the inverse of the photobleaching rate constant.

Figure 12:
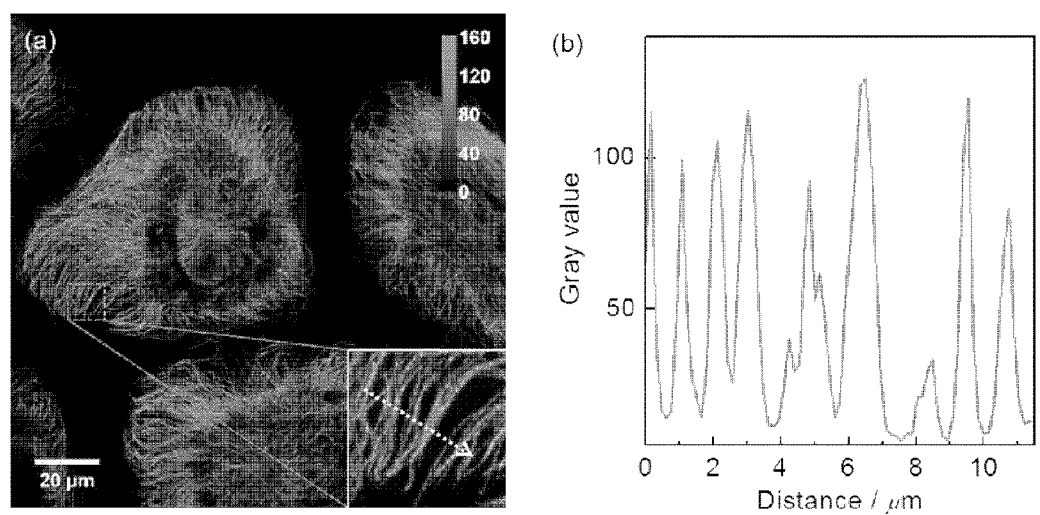
FIG. 12(*a*) is a confocal microscopy image of microtubules immunolabeled with Phox-COOH in a fixed HeLa cell, with an insert of an enlarged view of the selected region.
Figure 13:
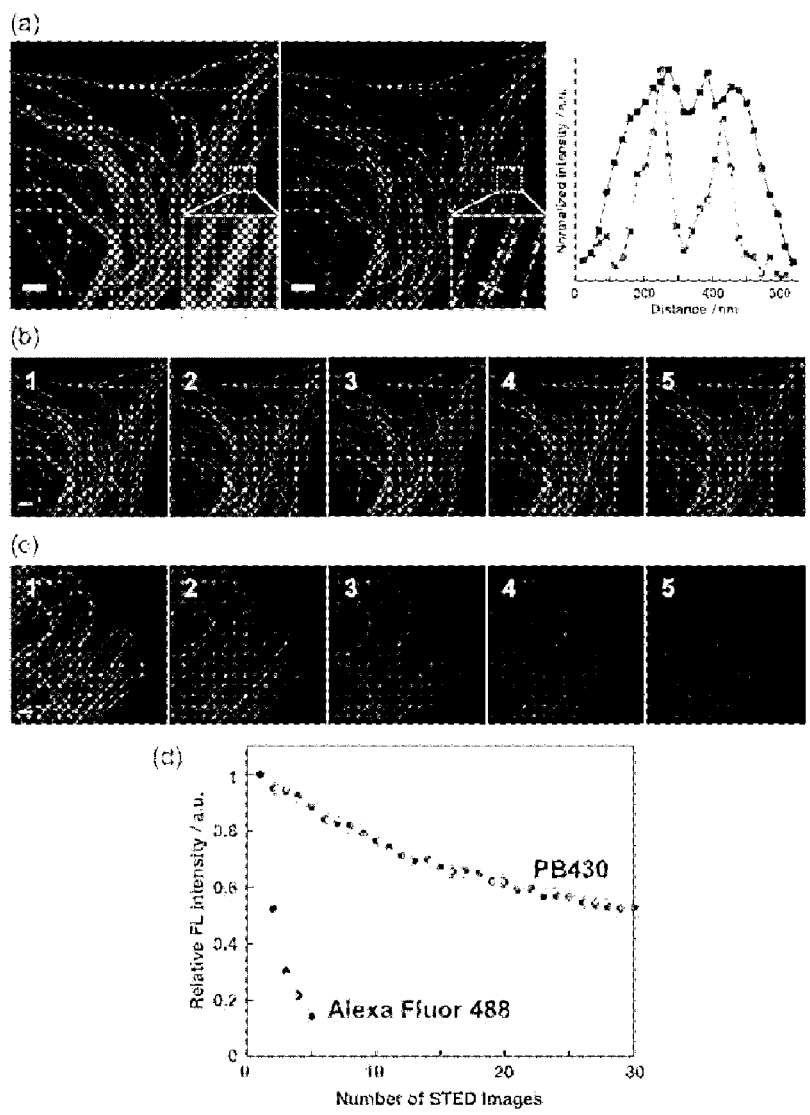
FIG. 13 is fluorescence images of immunolabeled microtubules in a fixed HeLa cell.

In order to obtain high-resolution images in gated CW-STED mode, an excitation wavelength of 470 nm was chosen for Phox-COOH from the pulsed WLL. To confirm practical utility of Phox-COOH as a fluorescent labeling reagent for proteins, α-tubulin in fixed HeLa cells was stained by indirect immunofluorescence with a Phox-COOH-labeled secondary antibody. A confocal image demonstrated that microtubules were successfully stained with negligible nonspecific binding, as is evident from the low background signals (FIG. 12). Under STED conditions ($\lambda_{STED}$=592 nm, STED laser power: about 30 mW, gated detection: 0.5 ns), individual microtubules were well separated from each other (FIG. 13(a)). The full width at half-maximum (FWHM) resolution of the STED image was 76±7 nm (FIG. 14(c)).

Figure 14:
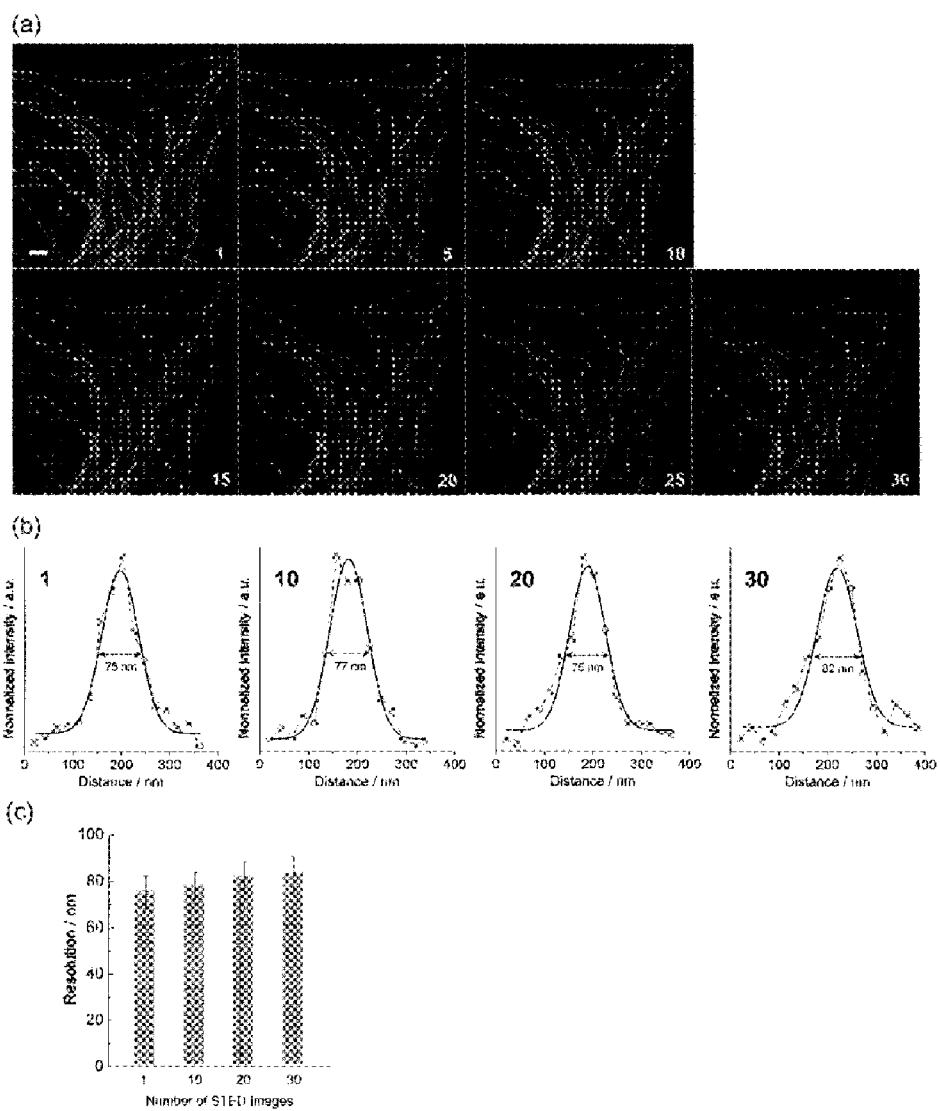
FIG. 14 is photographs of cells in the same region repeatedly captured under STED conditions (scale bar: 2 µm). Fixed HeLa cell microtubules were immunolabeled with Phox-COOH. The images were recorded with excitation at 470 nm (WLL, 5 microwatts), fluorescence depletion at 592 nm (CW-STED, 30 mW), and gated detection at Tg=0.5 ns.

Furthermore, it was possible to repeat STED imaging of the tubulin labeled with the Phox-COOH-conjugated secondary antibody while retaining the high fluorescence brightness. The total fluorescence signal intensity of the stained cells was monitored during repetitive scanning. After recording five images, Phox-COOH retained 80% or more of the initial fluorescence intensity and the microtubules were made clearly visible (FIG. 13(b)). In contrast, when the tubulin was labeled with the Alexa Fluor 488-conjugated secondary antibody, significant photobleaching (with only <15% of the initial intensity remaining) was observed under identical conditions (FIG. 13(c)). Remarkably, even after 30 consecutive scans of the same area, Phox-COOH retained more than 50% of the initial intensity (FIG. 13(d)) with a FWHM resolution of 83±8 nm (FIG. 14).

Figure 15:
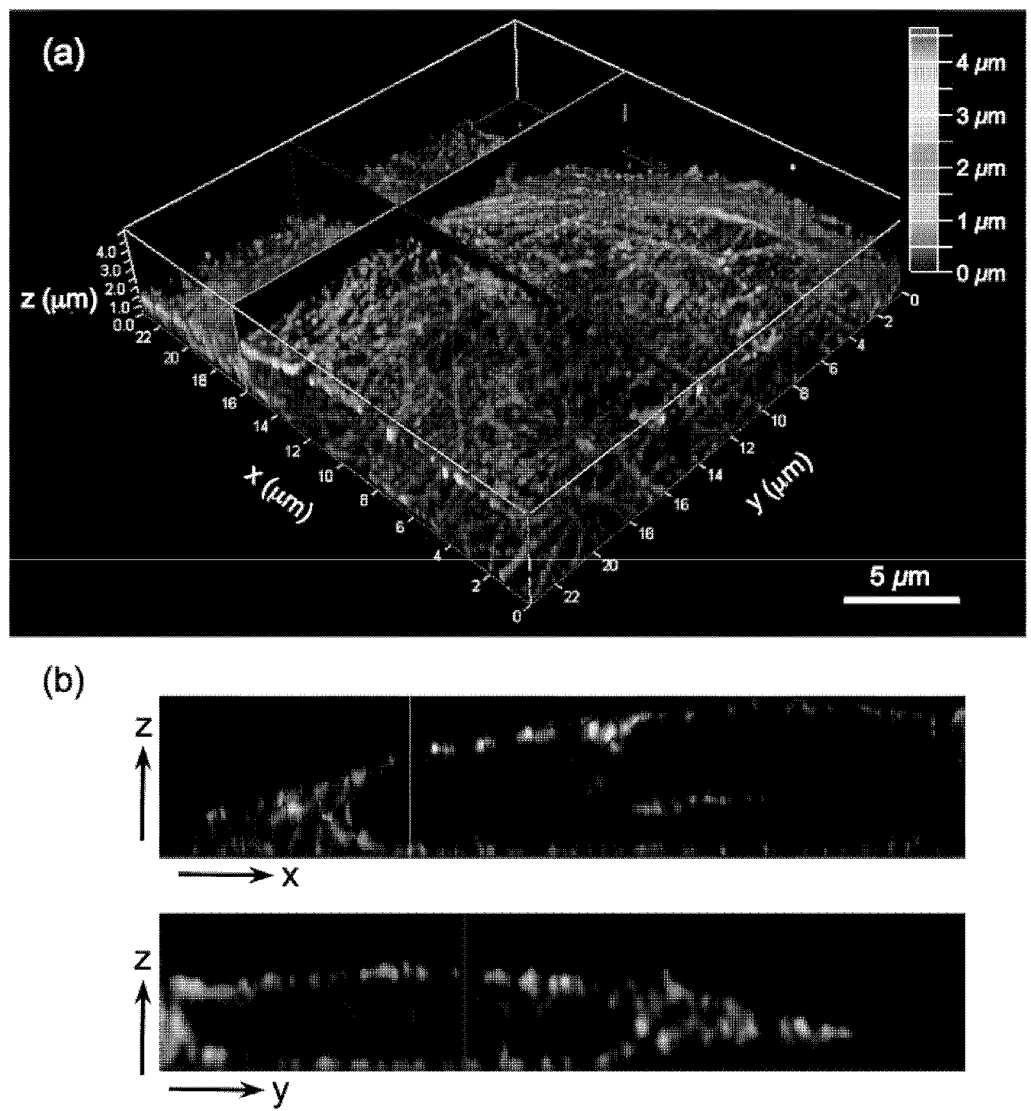
FIG. 15(*a*) is a three-dimensional STED image of HeLa cell microtubules immunolabeled with Phox-COOH, including a color scale corresponding to the height (increments in z-direction: 50 nm, scale bar: 5 µm). The image shows the results of imaging under the following STED conditions: excitation at 470 nm (WLL, 5 µW), fluorescence depletion at 592 nm (CW-STED, 30 mW, STED 3D z donut, 50%), and gated detection at tg=0.5 ns. Each image was deconvoluted using the Huygens Deconvolution Software (signal-to-noise ratio: 7; quality threshold: 0.05) and the z-section images were colored to represent the z-depth.
Figure 16:
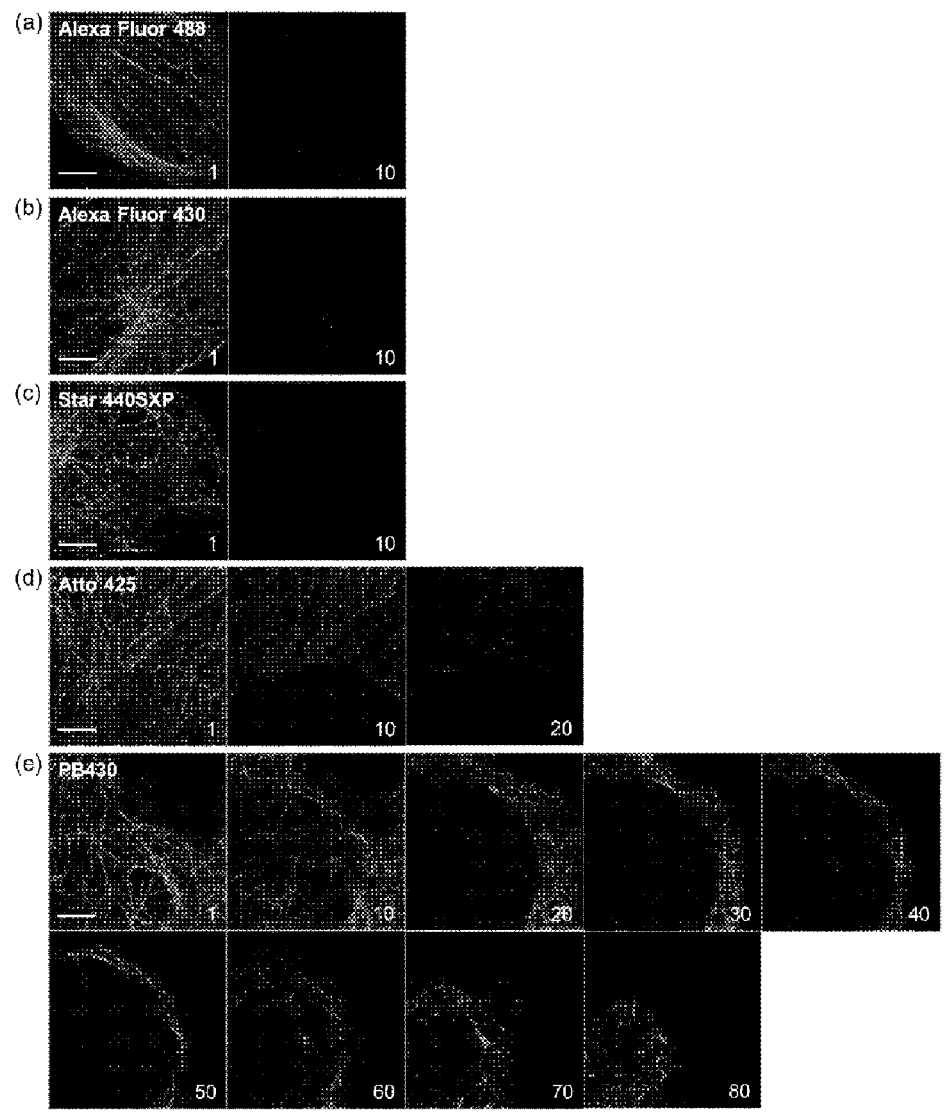
FIG. 16 shows a comparison of z-scan STED images of microtubules immunolabeled with (*a*) Alexa Fluor 488, (*b*) Alexa Fluor 430, (*c*) Star 440SXP, (*d*) Atto 425, and (*e*) Phox-COOH (PB430). Each numeral indicates the number of recorded z-scan images. Z-scan imaging was performed in steps of 50 nm and with excitation at 470 nm and a fluorescence depletion laser of 592 nm (CW-STED, 30 mW; STED 3D z donut, 50%). Scale bars indicate 2 µm.

To further demonstrate the utility of Phox-COOH in STED microscopy, z-scan STED imaging of microtubules was performed. The construction of a three-dimensional (3-D) image from two-dimensional STED images is challenging because rapid photobleaching during sequential xy-scans in usually unavoidable when using conventional dyes. The immunolabeled microtubules around the nucleus of the cell were scanned along the z-axis with a step of 50 nm. In the case of Phox-COOH, sufficient brightness and super-resolution of the microtubules were maintained while recording the STED images from the bottom to the top of the cell (z-depth of 4.0 μm). Thus, from 81 xy-images, the super-resolution 3-D structure of microtubules with z-axis resolution of 160 nm was successfully obtained after deconvolution and reconstruction (FIG. 15). In contrast, under the same STED imaging conditions, fluorescent signals of commercially available dyes, including Alexa Fluor 488, Alexa Fluor 430, and Atar 440SX, rapidly disappeared during the observation (FIG. 16). Although Atto 425 exhibited relatively higher photostability than other dyes (FIG. 16), it was still insufficient for the 3-D reconstruction with super-resolution.

Figure 17:
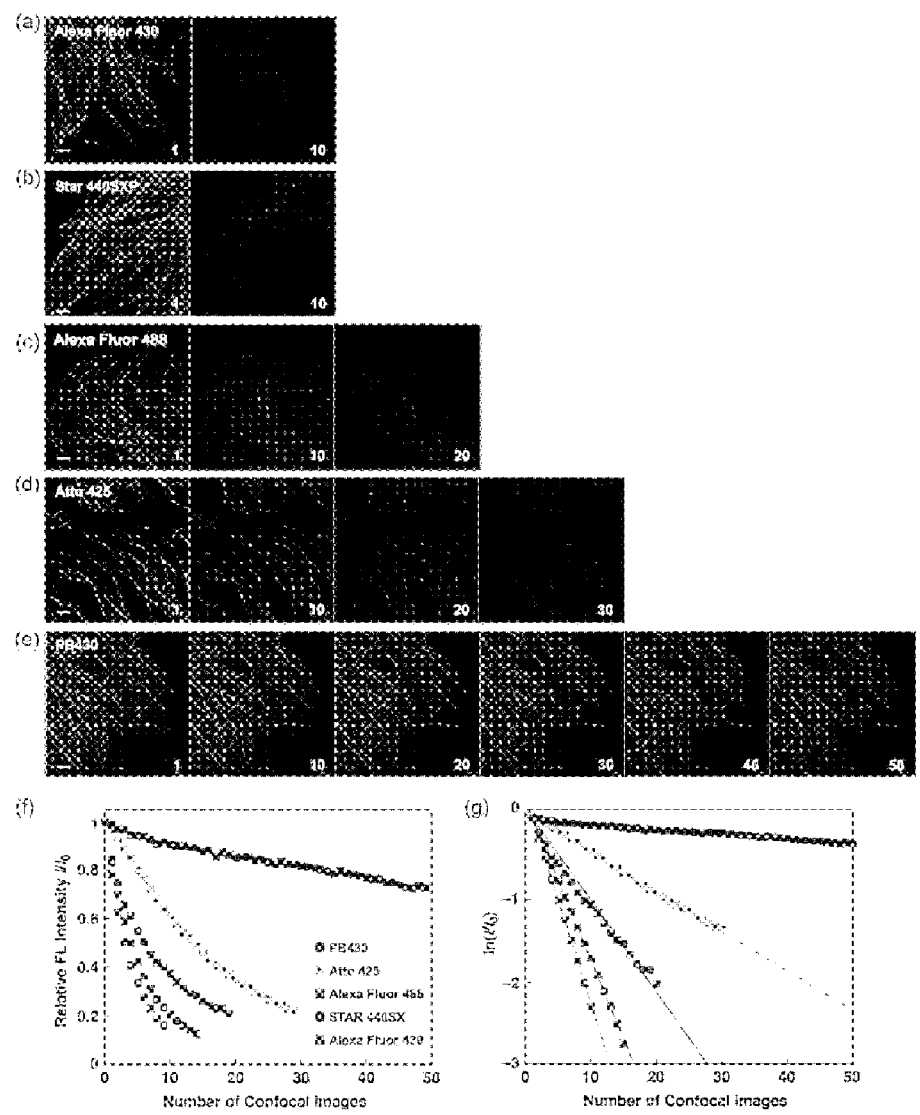
FIG. 17(*a*) to FIG. 17(*e*) show a comparison of fluorescence images of immunolabeled microtubules repeatedly photographed while being irradiated with a 470-nm confocal laser (WLL, 12 µW), the microtubules having been immunolabeled with (*a*) Alexa Fluor 430, (*b*) STAR 440SX, (*c*) Alexa Fluor 488, (*d*) Atto 425, or (*e*) Phox-COOH (PB430). Each numeral indicates the number of recorded confocal images. Scale bar: 2 µm.

To conduct multicolor imaging, we first evaluated the photostability of commercially available fluorescent dyes, such as Alexa Fluor 430, STAR 440SX, and Atto 425, to choose as suitable for comparison with Phox-COOH. As a representative dye with different optical properties, a comparison with Alexa Fluor 488 was also performed. Microtubules were immunolabeled with these dyes, and confocal images were taken repeatedly under irradiation with a confocal laser at 470 nm (WLL, 12 μW). As shown in FIG. 17, 70% or more of the initial intensity of Phox-COOH was retained even after acquisition of 50 confocal images. In contrast, almost no fluorescence signals were retained after 10 images when Alexa Fluor 430 and STAR 440SX were used. On the other hand, Alexa Fluor 488 and Atto 425 have slightly better photostability, and the bleaching rates of these dyes were 2.3 and 5.3 times, respectively, slower than that of Alexa Fluor 430 (Table 2). Because Alexa Fluor 430 showed the largest difference in photostability, Alexa Fluor 430 was decided to be used for comparison with Phox-COOH (PB430).

Figure 18:
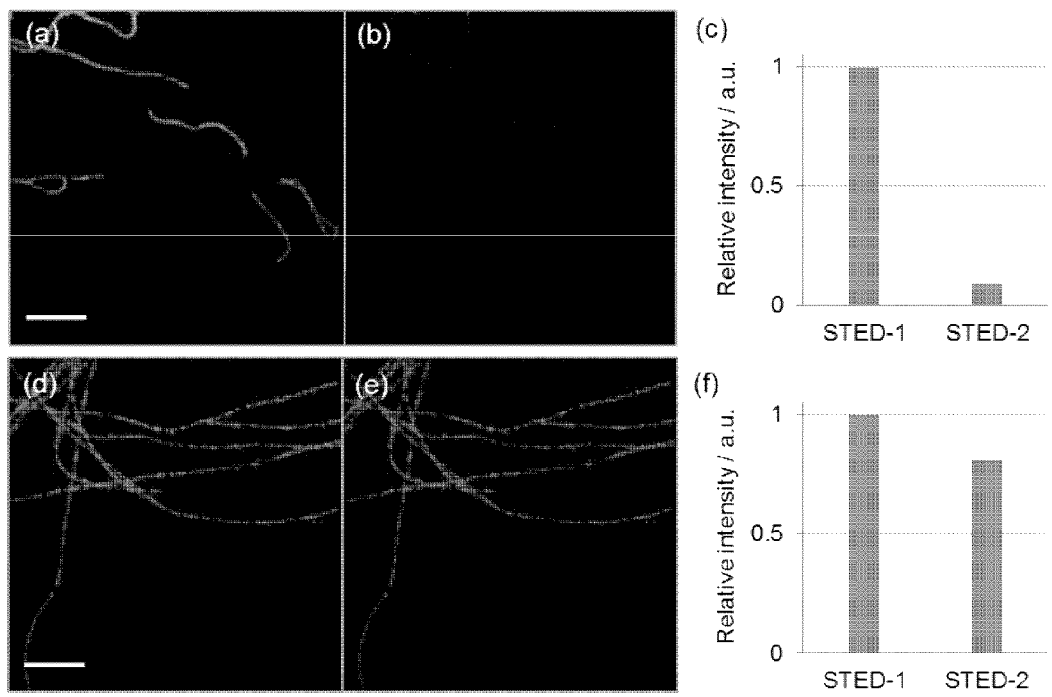
FIG. 18 shows a comparison of photostability between Alexa Fluor 430 ((*a*) to (*c*)) and Phox-COOH (PB430) ((*d*) to (*f*)). First and second STED images of Alexa Fluor 430-labeled vimentin ((*a*), (*b*)) and Phox-COOH (PB430)-labeled tubulin ((*d*), (*e*)) were consecutively photographed (scale bar: 2 µm), and their relative fluorescence intensities were compared ((*c*), (*f*)). The same imaging conditions, i.e., excitation at 470 nm (WLL, 10 µW), fluorescence depletion at 592 nm (CW-STED, 30 mW), and gated detection at Tg=0.5 ns, were applied to both imaging using Alexa Fluor 430 and imaging using Phox-COOH (PB430).

Initially, vimentin filaments of the fixed cells were stained with Alexa Fluor 430-conjugated secondary antibody. The photostability was compared to Phox-COOH (PB430) under identical STED conditions ($\varepsilon$=470 nm, $\lambda$=592 nm) (FIG. 18). No significant decrease in the fluorescence intensity was observed for Phox-COOH (PB430), whereas the fluorescence intensity of Alexa Fluor 430 in the second image decreased drastically (<10%) compared to the first image, in spite of the contribution of Alexa Fluor 430 to fluorescence.

Figure 19:
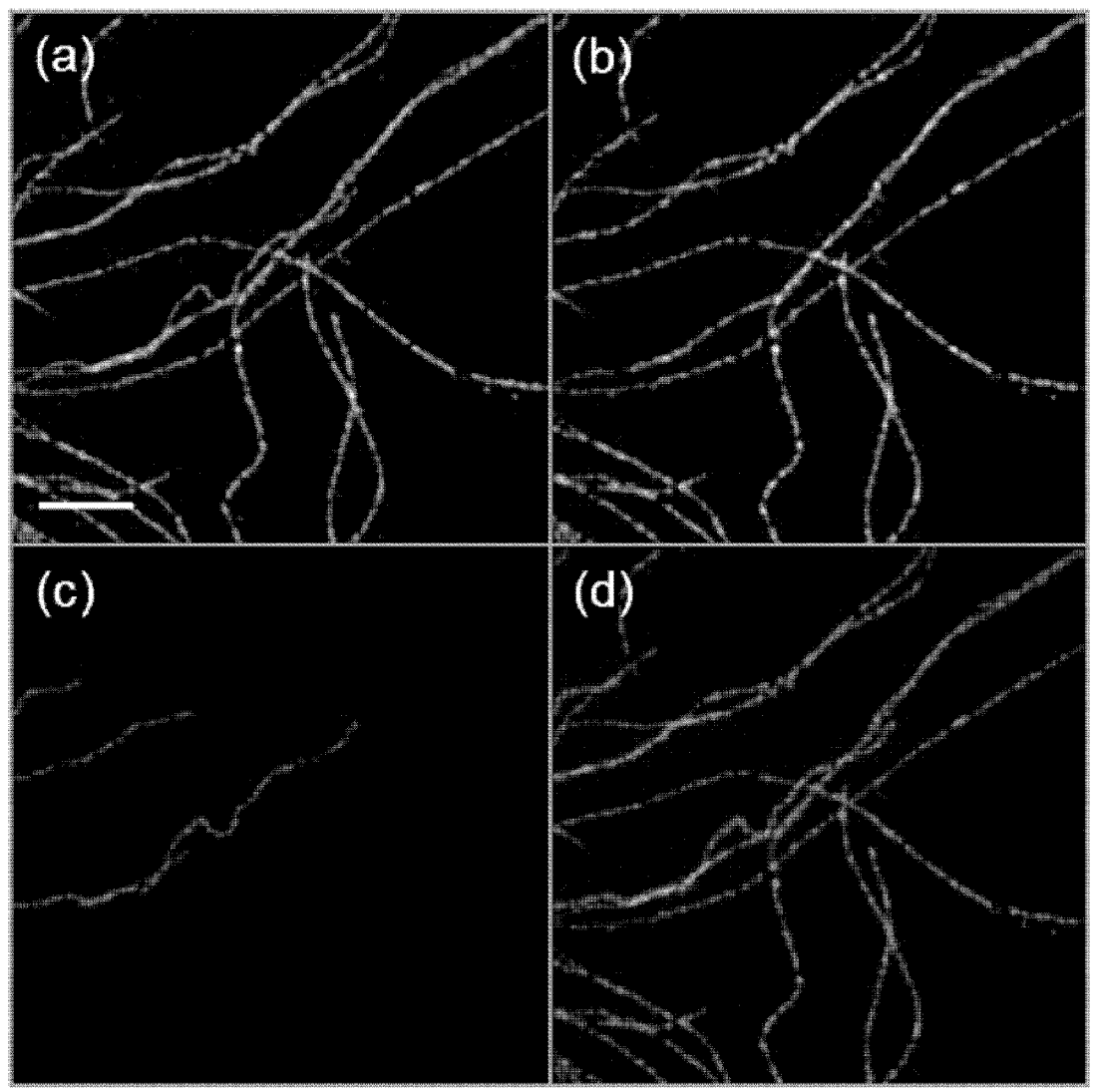
FIG. 19 shows a two-color imaging scheme combined with STED microscopy based on the distinctly different photostability of Phox-COOH (PB430) and Alexa Fluor 430. Microtubules and vimentin filaments were separately immunolabeled with Phox-COOH (PB430) and Alexa Fluor 430, respectively. Two STED microscopy images (deconvoluted data) were recorded consecutively with excitation at 470 nm (WLL, 10 µW) and fluorescence depletion at 592 nm (CW-STED, 30 mW).
Figure 20:
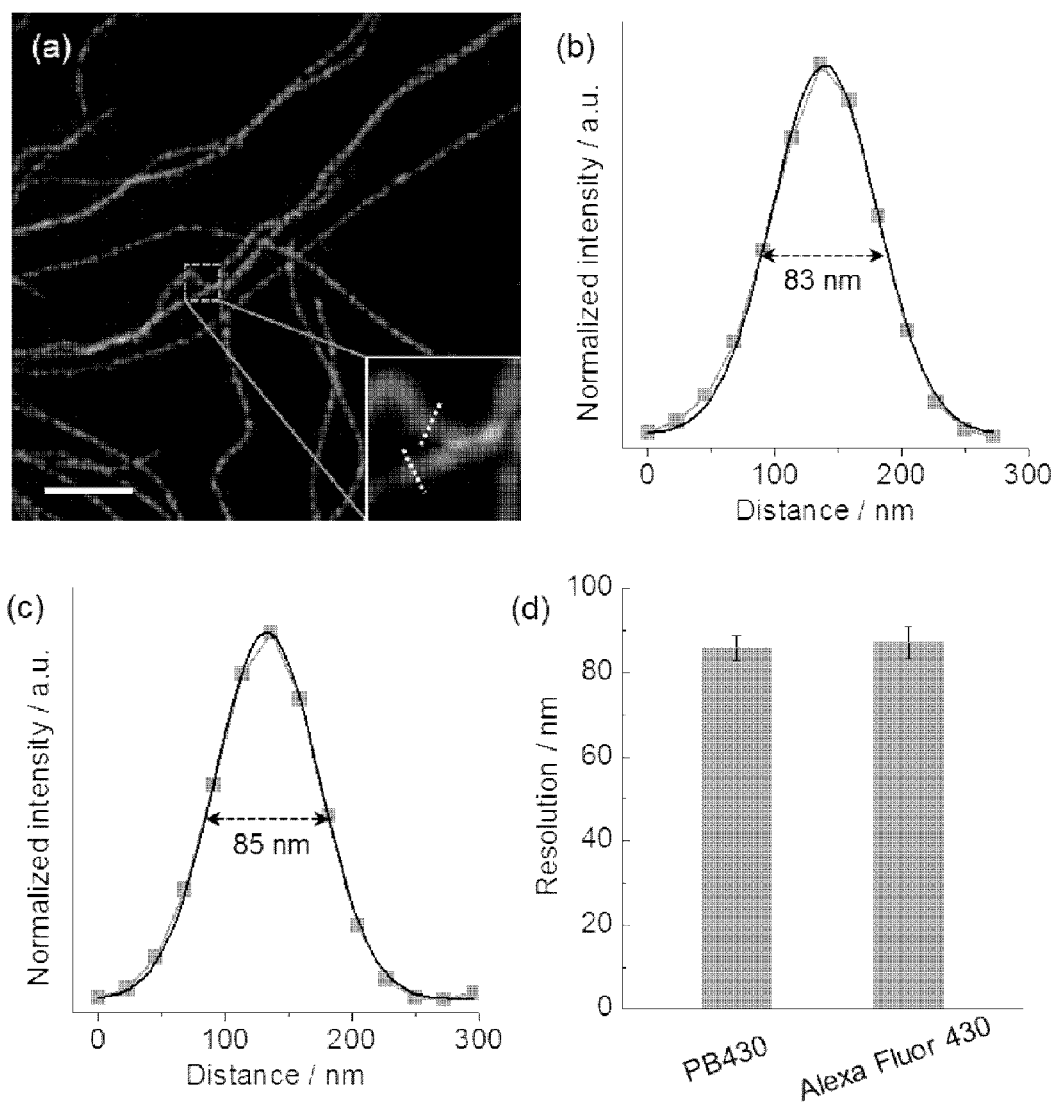
FIG. 20 shows the determination of two-color STED imaging resolution based on different photostability.

Tubulin and vimentin of the fixed cells were then stained with Phox-COOH (PB430)-conjugated secondary antibodies and Alexa Fluor 430-conjugated secondary antibodies, respectively. The first STED image was recorded (FIG. 19(a)), which should include both cytoskeletons. Subsequently, the second image was recorded under identical conditions. This resulted in the disappearance of several filament structures (FIG. 19(b)). Subtracting (removing) the second image (b) from the first image (a) enables obtaining a STED image of the lost filaments, which corresponds to the Alexa Fluor 430-labeled vimentin filaments (FIG. 19(c)). Reconstruction of the thus obtained two images (b) and (c) in different colors successfully provided a two-color STED image (FIG. 19(d)) that clearly shows a partially overlapped network of the two kinds of cytoskeletons shown in FIG. 19(a). Accordingly, these two types of cytoskeletons can be distinguished unambiguously by this method by using Phox-COOH (PB430). On the basis of statistical analysis, the FWHM resolutions of microtubules and vimentin filaments were determined to be 85±3 nm and 87±4 nm, respectively (FIG. 20). These values were comparable to that of the single-color STED image of microtubules immunolabeled with Phox-COOH (PB430). Therefore, the distinct photostability-based, two-color STED imaging was found to be a reliable method for obtaining a super-resolution that surpasses the diffraction limit of light microscopes.

The invention claimed is:

1. A phosphole compound represented by formula (1):

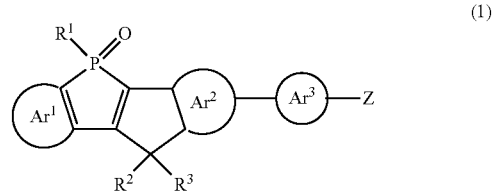

(1)

wherein $Ar^1$ and $Ar^2$ are the same or different, and represent an aromatic hydrocarbon ring or a heteroaromatic ring, and $Ar^1$ and $Ar^2$ are optionally substituted;

$Ar^3$ represents a divalent π-conjugated unit;

$R^1$ represents an alkyl group, a cycloalkyl group, an aryl group, or a heteroaryl group, wherein $R^1$ is optionally substituted;

$R^2$ and $R^3$ are the same or different, and represent a hydrogen atom, an alkyl group, a cycloalkyl group, an aryl group, or a heteroaryl group, wherein the alkyl group, the cycloalkyl group, the aryl group, or the heteroaryl group are optionally substituted; and Z represents carboxy, alkoxycarbonyl, hydroxy, halogenated alkyl, isocyano, isothiacyano, or a group having a structure represented by one of formulas (2A) to (2E) at an end thereof:

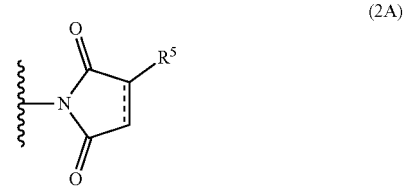

(2A)

-continued (2B)
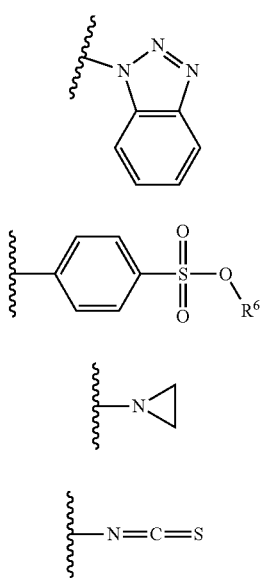

(2C)

(2D)

(2E)
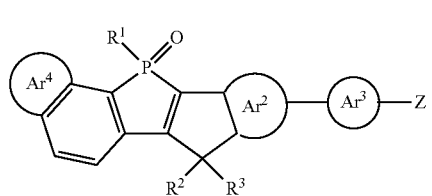

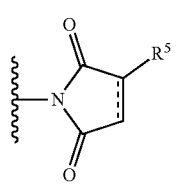

wherein R⁵ represents a hydrogen atom or a sulfo group, R⁶ represents an alkyl group, and the bond indicated by a solid line and a dashed line represents a single bond or a double bond.

2. The phosphole compound according to claim 1, wherein $Ar^3$ represents an alkenylene group, an alkynylene group, an arylene group, or an heteroarylene group, and $Ar^3$ is optionally substituted.

3. The phosphole compound according to claim 1, which is represented by formula (1B):

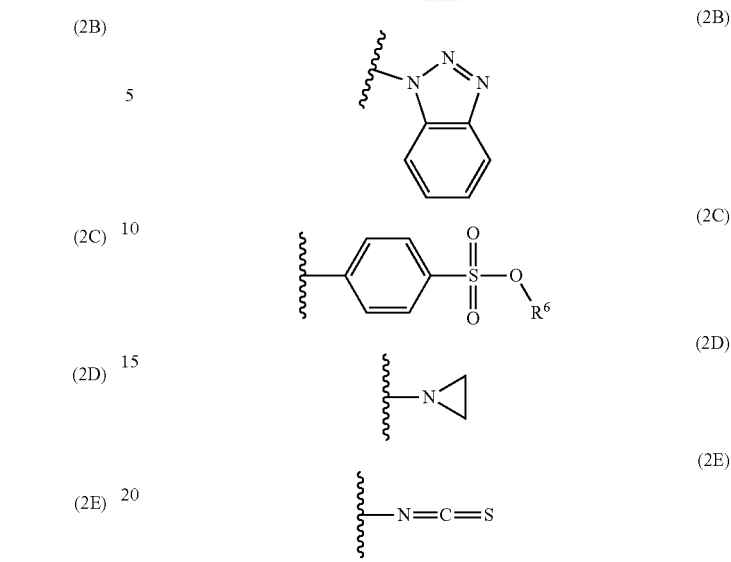
(1B)

wherein $Ar^2$, $Ar^3$, $R^1$, $R^2$, $R^3$, and Z are as defined above, and $Ar^4$ represents an aromatic hydrocarbon ring, and $Ar^4$ is optionally substituted.

4. The phosphole compound according to claim 1, wherein Z is carboxy or alkoxycarbonyl.

5. The phosphole compound according to claim 1, wherein Z is a group having a structure represented by one of formulas (2A) to (2E) at an end thereof:

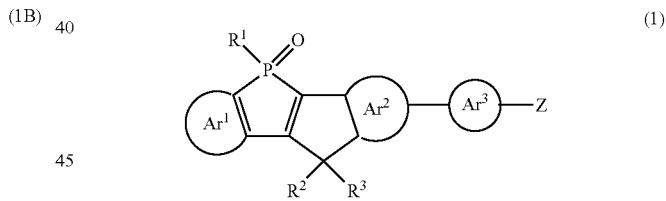
(2A)

-continued (2B)

(2C)

(2D)

(2E)

wherein $R^5$ represents a hydrogen atom or a sulfo group, $R^6$ represents an alkyl group, and the bond indicated by a solid line and a dashed line represents a single bond or a double bond.

6. A fluorescent dye comprising the phosphole compound according to claim 1.

7. The fluorescent dye according to claim 6, which is for stimulated emission depletion (STED) imaging.

8. A protein labeling agent comprising the phosphole compound according to claim 5.

9. A protein labeling agent comprising a phosphole compound represented by formula (1):

(1)

wherein $Ar^1$ and $Ar^2$ are the same or different, and represent an optionally substituted aromatic hydrocarbon ring or an optionally substituted heteroaromatic ring;

$Ar^3$ represents a divalent π-conjugated unit;

$R^1$ represents alkyl group, a cycloalkyl group, an aryl group, or a heteroaryl group wherein $R^1$ is optionally substituted;

$R^2$ and $R^3$ are the same or different, and represent a hydrogen atom, an alkyl group, a cycloalkyl group, an aryl group, or a heteroaryl group, wherein the alkyl group, the cycloalkyl group, the aryl group, or the heteroaryl group are optionally substituted; and Z represents an amine reactive group or a thiol reactive group.

10. The protein labeling agent according to claim 9, wherein $Ar^3$ represents an alkenylene group, an alkynylene group, an arylene group, or a heteroarylene group, and $Ar^3$ is optionally substituted.

11. The protein labeling agent according to claim 9, which is represented by formula (1B):

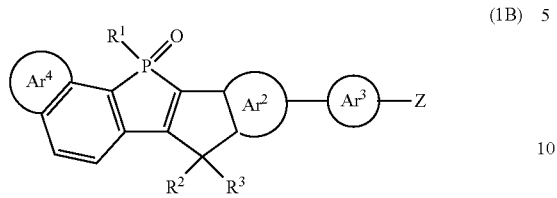

(1B)

wherein $Ar^2$, $Ar^3$, $R^1$, $R^2$, $R^3$, and Z are as defined above, and $Ar^4$ represents an aromatic hydrocarbon ring, and $Ar^4$ is optionally substituted.

12. A stimulated emission depletion (STED) imaging method using the phosphole compound according to claim 1.

13. A protein labeling kit comprising the phosphole compound according to claim 5.

14. A protein labeling method comprising reacting a protein with the phosphole compound according to claim 5.

15. A protein labeling kit comprising the protein labeling agent according to claim 9.

16. A protein labeling method comprising reacting a protein with the protein labeling agent according to claim 9.

* * * * *